(12) United States Patent
Pschirer et al.

(10) Patent No.: US 8,501,046 B2
(45) Date of Patent: *Aug. 6, 2013

(54) USE OF RYLENE DERIVATIVES AS PHOTOSENSITIZERS IN SOLAR CELLS

(75) Inventors: Neil Gregory Pschirer, Mainz (DE); Felix Eickemeyer, Mannheim (DE); Jan Schoenbeboom, Mannheim (DE); Jianqiang Qu, Ludwigshafen (DE); Martin Koenemann, Mannheim (DE); Klaus Muellen, Cologne (DE); Chen Li, Mainz (DE); Andreas Herrmann, Haren (NL); Peter Erk, Frankenthal (DE); Gero Nordmann, Heidelberg (DE); Alfred Kuhn, Dannstadt-Schauernehim (DE); Anders Hagfeldt, Bjorklingen (SE); Tomas Edvinsson, Uppsala (SE)

(73) Assignees: BASF SE, Ludwigshafen (DE); Max-Planck-Gesellschaft zur Foerderung der Wissenschaften E.V., Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,016

(22) Filed: Feb. 27, 2012

(65) Prior Publication Data

US 2012/0283432 A1 Nov. 8, 2012

Related U.S. Application Data

(63) Continuation of application No. 12/093,081, filed as application No. PCT/EP2006/068102 on Nov. 6, 2006, now Pat. No. 8,231,809.

(30) Foreign Application Priority Data

Nov. 10, 2005 (DE) .......................... 10 2005 053995

(51) Int. Cl.
*H01C 13/00* (2006.01)
*H01L 31/00* (2006.01)
*C07D 221/18* (2006.01)

(52) U.S. Cl.
USPC .......................... 252/501.1; 546/38; 136/263

(58) Field of Classification Search
USPC .......................... 252/501.1; 546/38; 136/263
See application file for complete search history.

(56) References Cited

U.S. PATENT DOCUMENTS

| | | | |
|---|---|---|---|
| 4,492,648 | A | 1/1985 | Claussen |
| 4,599,408 | A | 7/1986 | Spietschka et al. |
| 4,927,721 | A | 5/1990 | Gratzel et al. |
| 5,530,644 | A | 6/1996 | Maruta et al. |
| 6,359,211 | B1 | 3/2002 | Spitler et al. |
| 6,878,825 | B2 | 4/2005 | Krieger et al. |
| 7,138,522 | B2 | 11/2006 | Krieger et al. |
| 7,763,727 | B2 | 7/2010 | Fujiyama et al. |
| 7,799,919 | B2 | 9/2010 | Kohl et al. |

FOREIGN PATENT DOCUMENTS

| | | |
|---|---|---|
| DE | 197 57 312 | 6/1999 |
| DE | 198 09 840 | 9/1999 |
| DE | 198 48 555 | 4/2000 |
| EP | 1 176 646 | 1/2002 |
| JP | 10 189065 | 7/1998 |
| JP | 10 334954 | 12/1998 |
| JP | 2000 100484 | 4/2000 |
| JP | 2000 243463 | 9/2000 |
| JP | 2001093589 | 4/2001 |
| WO | 02 066438 | 8/2002 |
| WO | WO 2005089094 A2 * | 9/2005 |
| WO | 2006 117383 | 11/2006 |

OTHER PUBLICATIONS

Ferrere, S. et al., "New Perylenes for Dye Sensitization of TiO2" New Journal of Chemistry, vol. 26, No. 9, pp. 1155-1160, XP008024830, 2002.

Graetzel, M. et al., "A Low-Cost, High-Efficiency Solar Cell Based on Dye-Sensitized Colloidal TiO2 Films", Letter to Nature, vol. 353, pp. 737-740, 1991.

Bach, U. et al., "Solid-State Dye-Sensitized Mesoporous TiO2 Solar Cells With High Photon-Toelectron Conversion Efficiencies", Letter to Nature, vol. 395, pp. 583-585, 1998.

Schmidt-Mende, L. et al., "Organic Dye for Highly Efficient Solid-Sate Dye-Sensitized Solar Cells", Advanced Material, vol. 17, No. 7, pp. 813-815, 2005.

* cited by examiner

Primary Examiner — Mark Kopec
Assistant Examiner — Jaison Thomas
(74) Attorney, Agent, or Firm — Oblon, Spivak, McClelland, Maier & Neustadt, L.L.P.

(57) ABSTRACT

Use of rylene derivatives I

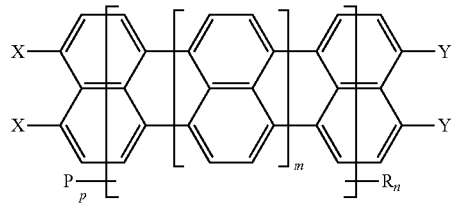

with the following definition of the variables:
X together

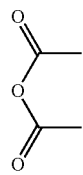 (x1)

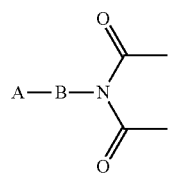

(x2)

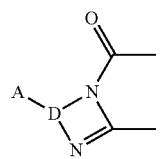

(x3)

both —COOM;

Y a radical

-L-NR$^1$R$^2$ (y1)

-L-Z—R$^3$ (y2)

the other radical hydrogen;
together

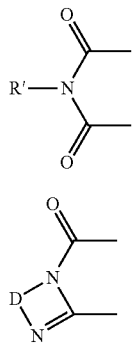

both hydrogen;
R is optionally substituted (het)aryloxy, (het)arylthio;
P is —NR$^1$R$^2$;
B is alkylene; optionally substituted phenylene; combinations thereof;
A is —COOM; —SO$_3$M; —PO$_3$M$_2$;
D is optionally substituted phenylene, naphthylene, pyridylene;
M is hydrogen; alkali metal cation; [NR$^5$]$_4^+$;
L is a chemical bond; optionally indirectly bonded, optionally substituted (het)arylene radical;
R$^1$, R$^2$ are optionally substituted (cyclo)alkyl, (het)aryl; together optionally substituted ring comprising the nitrogen atom;
Z is —O—; —S—;
R$^3$ is optionally substituted alkyl, (het)aryl;
R' is hydrogen; optionally substituted (cyclo)alkyl, (het)aryl;
R$^5$ is hydrogen; optionally substituted alkyl (het)aryl;
m is 0, 1, 2;
n, p m=0: 0, 2, 4 where: n+p=2, 4, if appropriate 0;
   m=1: 0, 2, 4 where: n+p=0, 2, 4;
   m=2: 0, 4, 6 where: n+p=0, 4, 6,
or of mixtures thereof as photosensitizers in solar cells.

22 Claims, 3 Drawing Sheets

USE OF RYLENE DERIVATIVES AS PHOTOSENSITIZERS IN SOLAR CELLS

CROSS REFERENCE TO RELATED APPLICATIONS

This application is a continuation of U.S. application Ser. No. 12/093,081, filed on May 8, 2008, now U.S. Pat. No. 8,231,809 which is a 371 of PCT/EP06/068102, filed no Nov. 6, 2006, and claims priority to German Patent Application No. 10 2005 053 995.5, filed on Nov. 10, 2005.

BACKGROUND OF THE INVENTION

The present invention relates to the use of rylene derivatives of the general formula I

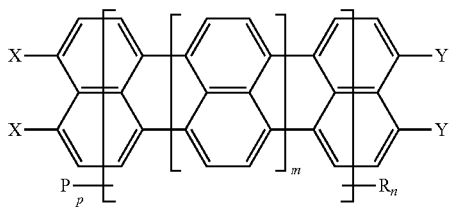

in which the variables are each defined as follows:
X are joined to one another with formation of a six-membered ring to give a radical of the formula (x1), (x2) or (x3)

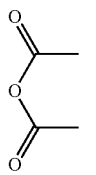

(x1)

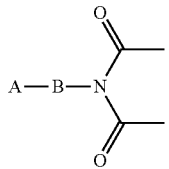

(x2)

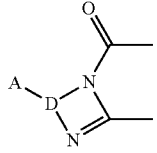

(x3)

both are a —COOM radical;
Y one of the two radicals is a radical of the formula (y1)

$$-L-NR^1R^2 \quad (y1)$$

or a radical of the formula (y2)

$$-L-Z-R^3 \quad (y2)$$

and the other radical in each case is hydrogen; are joined together with formation of a six-membered ring to give a radical of the formula (y3) or (y4)

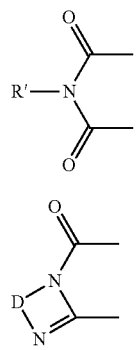

or both are hydrogen;
R are identical or different radicals:
aryloxy, arylthio, hetaryloxy or hetarylthio, to each of which may be fused further saturated or unsaturated 5- to 7-membered rings whose carbon skeleton may be interrupted by one or more —O—, —S—, —NR$^4$—, —N=CR$^4$—, —CO—, —SO— and/or —SO$_2$-moieties, where the entire ring system may be mono- or polysubstituted by the (i), (ii), (iii), (iv) and/or (v) radicals:
(i) C$_1$-C$_{30}$-alkyl whose carbon chain may be interrupted by one or more —O—, —S—, —NR$^4$—, —N=CR$^4$—, —C≡C—, —CR$^4$=CR$^4$—, —CO—, —SO— and/or —SO$_2$— moieties and which may be mono- or polysubstituted by: C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl and/or saturated or unsaturated C$_4$-C$_7$-cycloalkyl whose carbon skeleton may be interrupted by one or more —O—, —S—, —NR$^4$—, —N=CR$^4$—, —CR$^4$=CR$^4$—, —CO—, —SO— and/or —SO$_2$— moieties, where the (het)aryl and cycloalkyl radicals may each be mono- or polysubstituted by C$_1$-C$_{18}$-alkyl and/or the above radicals specified as substituents for alkyl;
(ii) C$_3$-C$_8$-cycloalkyl whose carbon skeleton may be interrupted by one or more —O—, —S—, —NR$^4$—, —N=CR$^4$—, —CR$^4$=CR$^4$—, —CO—, —SO— and/or —SO$_2$— moieties and to which may be fused further saturated or unsaturated 5- to 7-membered rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$ and/or —POR$^7$R$^7$;
(iii) aryl or hetaryl to which may be fused further saturated or unsaturated 5- to 7-membered rings whose carbon skeleton may be interrupted by one or more —O—, —S—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl, (het)aryloxy and/or (het)arylthio, where the (het)aryl radicals may each be mono- or polysubstituted by C$_1$-C$_{18}$-alkyl, C$_1$-C$_{12}$-alkoxy, C$_1$-C$_6$-alkylthio, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7_2$, —POR$^7$R$^7$;

(iv) a —U-aryl radical which may be mono- or polysubstituted by the above radicals specified as substituents for the aryl radicals (iii), where U is a —O—, —S—, —NR$^3$—, —CO—, —SO— or —SO$_2$— moiety;

(v) C$_1$-C$_{12}$-alkoxy, C$_1$-C$_6$-alkylthio, —C≡CR$^4$, —CR$^4$=CR$^4_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7_2$ and/or —POR$^7$R$^7$;

P is an amino radical —N$^1$R$^2$;

B is C$_1$-C$_6$-alkylene, phenylene or combinations of these bridging members, where the phenylene radicals may be mono- or polysubstituted by C$_1$-C$_{12}$-alkyl, nitro, cyano and/or halogen;

A is —COOM, —SO$_3$M or —PO$_3$M;

D is phenylene, naphthylene or pyridylene, each of which may be mono- or polysubstituted by C$_1$-C$_{12}$-alkyl, C$_1$-C$_{12}$-alkoxy, hydroxyl, nitro and/or halogen;

M is hydrogen, monovalent or divalent metal cation, especially alkaline earth metal or alkali metal cation, ammonium salts of cyclic amines, guanidinium salts or [NR$^5$]$_4^+$;

L is a chemical bond or an arylene or hetarylene radical, bonded to the rylene skeleton directly or via ethenylene or ethynylene, of the formulae —Ar— —Ar-E-Ar— in which the (het)arylene radicals Ar may be the same or different, may comprise heteroatoms as ring atoms and/or may have fused saturated or unsaturated 5- to 7-membered rings which may likewise comprise heteroatoms, where the entire ring system may be mono- or polysubstituted by phenyl, C$_1$-C$_{12}$-alkyl, C$_1$-C$_{12}$-alkoxy, C$_1$-C$_{12}$-alkylthio and/or —NR$^5$R$^6$;

E is a chemical bond or an —O—, —S—, —NR$^4$—, —C≡C—, —CR$^4$=CR$^4$— or C$_1$-C$_6$-alkylene moiety;

R$^1$, R$^2$ are each independently one of the alkyl radicals (i), cycloalkyl radicals (ii) or (het)aryl radicals (iii) specified as substituents for the R radicals; joined together to form a saturated or unsaturated, 5- to 7-membered ring which comprises the nitrogen atom and whose carbon chain may be interrupted by one or more —O—, —S— and/or —NR$^4$-moieties, to which may be fused one or two unsaturated or saturated 4- to 8-membered rings whose carbon chain may likewise be interrupted by these moieties and/or —N=, where the entire ring system may be mono- or polysubstituted by: C$_1$-C$_{24}$-alkyl which may be substituted by C$_1$-C$_{18}$-alkoxy, C$_1$-C$_{18}$-alkylthio and/or —NR$^5$R$^6$, (het)aryl which may be mono- or polysubstituted by C$_1$-C$_{18}$-alkyl and/or the aforementioned radicals as substituents for alkyl, C$_1$-C$_{18}$-alkoxy, C$_1$-C$_{18}$-alkylthio and/or —NR$^5$R$^6$;

Z is —O— or —S—;

R$^3$ is one of the alkyl radicals (i) or (het)aryl radicals (iii) specified as substituents for the R radicals;

R' is hydrogen;
C$_1$-C$_{30}$-alkyl whose carbon chain may be interrupted by one or more —O—, —S—, —NR$^4$—, —N=CR$^4$—, —C≡C—, —CR$^4$=CR$^4$—, —CO—, —SO— and/or —SO$_2$— moieties and which may be mono- or polysubstituted by the (ii), (iii), (iv) and/or (v) radicals specified as substituents for the R radicals;

C$_3$-C$_8$-cycloalkyl to which may be fused further saturated or unsaturated 5- to 7-membered rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by the (i), (ii), (iii), (iv) and/or (v) radicals specified as substituents for the R radicals;

aryl or hetaryl to which may be fused further saturated or unsaturated 5- to 7-membered rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by the (i), (ii), (iii), (iv), (v) radicals specified as substituents for the R radicals, and/or aryl- and/or hetarylazo, each of which may be substituted by C$_1$-C$_{10}$-alkyl, C$_1$-C$_6$-alkoxy and/or cyano;

R$^4$ is hydrogen or C$_1$-C$_{18}$-alkyl, where the R$^4$ radicals may be the same or different when they occur more than once;

R$^5$, R$^6$ are each independently:
hydrogen;
C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^8$;
aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;
where the R$^5$ radicals may be the same or different when they occur more than once;

R$^7$ is C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^8$; aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl,
where the R$^7$ radicals may be the same or different when they occur more than once;

R$^8$ is C$_1$-C$_{18}$-alkyl;

R$^9$, R$^{10}$ are each C$_1$-C$_{30}$-alkyl whose carbon chain may be interrupted by one or more —O—, —S—, —NR$^4$—, —N=CR$^4$—, —C≡C—, —CR$^4$=CR$^4$—, —CO—, —SO— and/or —SO$_2$— moieties and which may be mono- or polysubstituted by: C$_1$-C$_{12}$-alkoxy, C$_1$-C$_6$-alkylthio, —C≡CR$^4$, —CR$^4$=CR$^4_2$, hydroxyl, —NR$^5$R$^6$, —NR$^5$COR$^6$, (het)aryl and/or saturated or unsaturated C$_4$-C$_7$-cycloalkyl whose carbon skeleton may be interrupted by one or more —O—, —S—, —NR$^4$—, —N=CR$^4$— and/or —CR$^4$=CR$^4$ moieties, where the (het)aryl and cycloalkyl radicals may each be mono- or polysubstituted by C$_1$-C$_{18}$-alkyl and/or the above radicals specified as substituents for alkyl;
aryl or hetaryl to which may be fused further saturated or unsaturated 5- to 7-membered rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, —NR$^5$R$^6$, —NR$^5$COR$^6$, (het)aryl, (het)aryloxy and/or (het)arylthio, where the (het)aryl radicals may in each case be mono- or polysubstituted by C$_1$-C$_{18}$-alkyl, C$_1$-C$_{12}$-alkoxy, hydroxyl, —NR$^5$R$^6$ and/or —NR$^5$COR$^6$; joined to the nitrogen atom to form a saturated or unsaturated, 5- to 7-membered ring whose carbon chain may be interrupted by one or more —O—, —S— and/or —NR$^4$— moieties, to which may be fused one or two unsaturated or saturated 4- to 8-membered rings whose carbon chain may likewise be interrupted by these moieties and/or —N=, where the entire ring system may be mono- or polysubstituted by C$_1$-C$_{24}$-alkyl which may be substituted by C$_1$-C$_{18}$-alkoxy, C$_1$-C$_{18}$-alkylthio and/or —NR$^5$R$^6$, (het)aryl which may be mono- or polysubstituted by C$_1$-C$_{18}$-alkyl and/or the above radicals specified as substituents for alkyl, C$_1$-C$_{18}$-alkoxy, C$_1$-C$_{18}$-alkylthio and/or —NR$^5$R$^6$;

m is 0, 1 or 2;

n is 0, 2 or 4 when m=0 or 1;

is 0, 4 or 6 when m=2;

p is 0, 2 or 4 when m=0, where n+p=2 or 4 or may also be 0 when the two X radicals are joined together with formation of a six-membered ring to give a radical of the formula (x1) or (x2) or both are a —COOM radical and one of the two Y radicals is a radical of the formula (y1) or (y2) and the other radical is hydrogen, where at least one of the two R$^1$ or R$^2$ radicals in the (y1) radical is one of the (het)aryl radicals (iii) specified as substituents for the R radicals when L is a chemical bond;

is 0, 2 or 4 when m=1, where n+p=0, 2 or 4;

is 0, 4 or 6 when m=2, where n+p=0, 4 or 6, or of mixtures of the rylene derivatives as photosensitizers in solar cells.

The invention also relates to novel dye-sensitized solar cells which comprise the rylene derivatives I, and also to novel rylene derivatives Ia and Ib.

DESCRIPTION OF RELATED ART

The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. The photovoltage thus generated can bring about a photocurrent in an external circuit through which the solar cell delivers its power.

The semiconductor can absorb only those photons which have an energy which is greater than its band gap. The size of the semiconductor band gap thus determines the fraction of sunlight which can be converted to electrical energy.

Thin layers or films of metal oxides are known to constitute inexpensive solid semiconductor materials (n-semiconductors), but their absorption, owing to large band gaps, is typically not within the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the conduction band of the semiconductor. With the aid of a redox system which is used additionally in the cell and is reduced at the counterelectrode, electrons are recycled to the sensitizer which is thus regenerated.

Of particular interest for use in solar cells are the semiconductors zinc oxide, tin dioxide and especially titanium dioxide, which are used in the form of nanocrystalline porous layers. These layers have a large surface area which is coated with the sensitizer, so that high absorption of sunlight is achieved.

Dye-sensitized solar cells which are based on titanium dioxide as the semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. These solar cells comprise monomolecular films of transition metal complexes, especially ruthenium complexes which are bonded to the titanium dioxide layer via acid groups, as sensitizers and iodine/iodide redox systems present in dissolved form or amorphous organic p-conductors based on spirobifluorenes.

Also proposed repeatedly as sensitizers, not least for reasons of cost, have been metal-free organic dyes.

For instance, U.S. Pat. No. 6,359,211 describes, for this purpose, cyanine, oxazine, thiazine and acridine dyes which have carboxyl groups bonded via an alkylene radical for securing to the titanium dioxide semiconductor.

JP-A-10-189065, 2000-243463, 2001-093589, 2000-100484 and 10-334954 describe various perylene-3,4:9,10-tetracarboxylic acid derivatives unsubstituted in the perylene skeleton for use in semiconductor solar cells. They are specifically: perylenetetra-carboximides which bear carboxyalkyl, carboxyaryl, carboxyarylalkyl or carboxyalkylaryl radicals on the imide nitrogen atoms and/or have been imidized with p-diaminobenzene derivatives in which the nitrogen atom of the amino group has been substituted in the p-position by two further phenyl radicals or is a constituent of a heteroaromatic tricyclic system; perylene-3,4:9,10-tetracarboxylic monoanhydride monoimides which bear the aforementioned radicals or alkyl or aryl radicals without further functionalization on the imide nitrogen atom, or semi-condensates of perylene-3,4:9,10-tetracarboxylic dianhydride with 1,2-diaminobenzenes or 1,8-diaminonaphthalenes which are converted by further reaction with primary amine to the corresponding diimides or double condensates; condensates of perylene-3,4:9,10-tetracarboxylic dianhydride with 1,2-diaminobenzenes which have been functionalized by carboxyl or amino radicals; and perylene-3,4:9,10-tetracarboximides which have been imidized with aliphatic or aromatic diamines.

New J. Chem. 26, p. 1155-1160 (2002) examines the sensitization of titanium dioxide with perylene derivatives which are unsubstituted in the perylene skeleton (bay positions). Specific mention is made of 9-dialkylaminoperylene-3,4-dicarboxylic anhydrides, perylene-3,4-dicarboximides which are substituted in the 9-position by dialkylamino or carboxymethylamino and bear a carboxymethyl or a 2,5-di(tert-butyl)phenyl radical on the imide nitrogen atom, and N-dodecylaminoperylene-3,4:9,10-tetracarboxylic monoanhydride monoimide. However, the liquid electrolyte solar cells based on these perylene derivatives exhibited substantially lower efficiencies than a solar cell sensitized with a ruthenium complex for comparison.

The inventive perylene derivatives I differ from the perylene derivatives described in the literature by the type of end groups and/or the substituents in the perylene skeleton.

Finally, Adv. Mater. 17, p. 813-815 (2005) proposes an indoline dye for solar cells with spirobifluorenes as an amorphous organic p-conductor.

BRIEF SUMMARY OF THE INVENTION

It was an object of the invention to provide organic dyes which feature advantageous performance properties, especially strong light absorption and high stability, and give rise to solar cells with good efficiencies. In particular, the absorption spectrum should be as wide as possible, and should in particular comprise the NIR region.

DETAILED DESCRIPTION OF THE INVENTION

Figure 1:
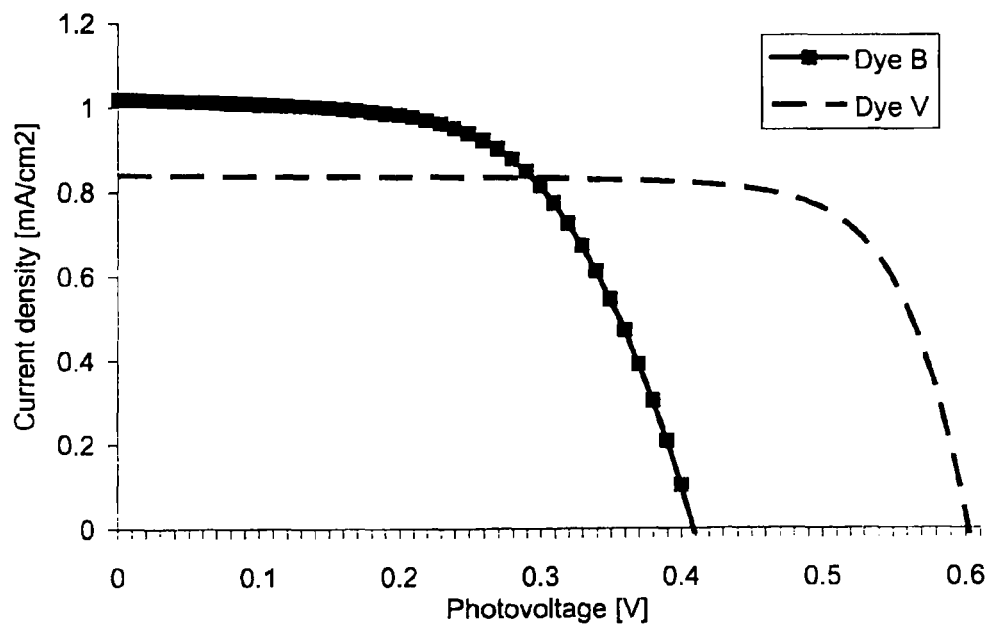
FIG. 1 depicts current/voltage curves for the solar cells of Example 1.

Accordingly, we have found the use of rylene derivatives of the formula I defined at the outset

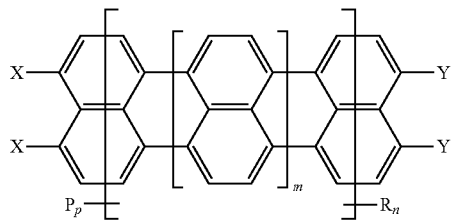

and mixtures thereof as photosensitizers in solar cells.

We have also found dye-sensitized solar cells which comprise the rylene derivatives I as photosensitizers.

We have additionally rylene derivatives of the general formula Ia

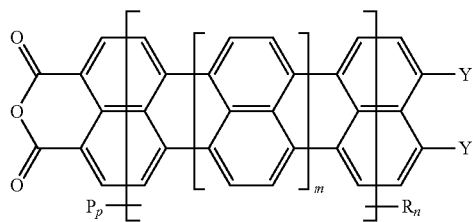

in which the dicarboxylic anhydride radical may also represent two carboxyl radicals —COOM and the variables are each defined as follows:

Y one of the two radicals is a radical of the formula (y1)

 -L-NR'R²  (y1)

or a radical of the formula (y2)

 -L-Z—R³  (y2)

and the other radical in each case is hydrogen;
are joined together with formation of a six-membered ring to give a radical of the formula (y3) or (y4)

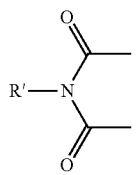

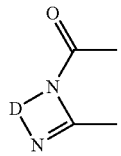

R are identical or different radicals:
aryloxy, arylthio, hetaryloxy or hetarylthio, to each of which may be fused further saturated or unsaturated 5- to 7-membered rings whose carbon skeleton may be interrupted by one or more —O—, —S—, —NR⁴—, —N═CR⁴—, —CO—, —SO— and/or —SO₂—moieties, where the entire ring system may be mono- or polysubstituted by the (i), (ii), (iii), (iv) and/or (v) radicals:
(i) $C_1$-$C_{30}$-alkyl whose carbon chain may be interrupted by one or more —O—, —S—, —NR⁴—, —N═CR⁴—, —C≡C—, —CR⁴═CR⁴—, —CO—, —SO— and/or —SO₂— moieties and which may be mono- or polysubstituted by: $C_1$-$C_{12}$-alkoxy, $C_1$-$C_6$-alkylthio, —C≡CR⁴, —CR⁴═CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂, —POR⁷R⁷, (het)aryl and/or saturated or unsaturated $C_4$-$C_7$-cycloalkyl whose carbon skeleton may be interrupted by one or more —O—, —S—, —NR⁴—, —N═CR⁴—, —CR⁴═CR⁴—, —CO—, —SO— and/or —SO₂— moieties, where the (het)aryl and cycloalkyl radicals may each be mono- or polysubstituted by $C_1$-$C_{18}$-alkyl and/or the above radicals specified as substituents for alkyl;
(ii) $C_3$-$C_8$-cycloalkyl whose carbon skeleton may be interrupted by one or more —O—, —S—, —NR⁴—, —N═CR⁴—, —CR⁴═CR⁴—, —CO—, —SO— and/or —SO₂— moieties and to which may be fused further saturated or unsaturated 5- to 7-membered rings whose carbon skeleton may be interrupted by one or more —O—, —S—, —NR⁴—, —N═CR⁴—, —CR⁴═CR⁴—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴═CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂ and/or —POR⁷R⁷;
(iii) aryl or hetaryl to which may be fused further saturated or unsaturated 5- to 7-membered rings whose carbon skeleton may be interrupted by one or more —O—, —S—, —N═CR⁴—, —CR⁴═CR⁴—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴═CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂, —POR⁷R⁷, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, $C_1$-$C_6$-alkylthio, hydroxyl, mercapto, halogen, cyano, nitro, —$NR^9R^{10}$, —$NR^5COR^6$, —$CONR^5R^6$, —$SO_2NR^5R^6$, —$COOR^7$, —$SO_3R^7$, —$PR^7_2$, —$POR^7R^7$;

(iv) a —U-aryl radical which may be mono- or polysubstituted by the above radicals specified as substituents for the aryl radicals (iii), where U is a —O—, —S—, —$NR^3$—, —CO—, —SO— or —$SO_2$— moiety;

(v) $C_1$-$C_{12}$-alkoxy, $C_1$-$C_6$-alkylthio, —C≡$CR^4$, —$CR^4$=$CR^4_2$, hydroxyl, mercapto, halogen, cyano, nitro, —$NR^9R^{10}$, —$NR^5COR^6$, —$CONR^5R^6$, —$SO_2NR^5R^6$, —$COOR^7$, —$SO_3R^7$, —$PR^7_2$ and/or —$POR^7R^7$;

P is an amino radical —$NR^1R^2$;

M is hydrogen, monovalent or divalent metal cation, especially alkaline earth metal or alkali metal cation, ammonium salts of cyclic amines, guanidinium salts or $[NR^5]_4^+$;

L is a chemical bond or an arylene or hetarylene radical, bonded to the rylene skeleton directly or via ethenylene or ethynylene, of the formulae —Ar—  —Ar-E-Ar— in which the (het)arylene radicals Ar may be the same or different, may comprise heteroatoms as ring atoms and/or may have fused saturated or unsaturated 5- to 7-membered rings which may likewise comprise heteroatoms, where the entire ring system may be mono- or polysubstituted by phenyl, $C_1$-$C_{12}$-alkyl, $C_1$-$C_{12}$-alkoxy, $C_1$-$C_{12}$-alkylthio and/or —$NR^5R^6$;

E is a chemical bond or an —O—, —S—, —C≡C—, —$CR^4$=$CR^4$— or $C_1$-$C_6$-alkylene moiety;

$R^1$, $R^2$ are each independently one of the alkyl radicals (i), cycloalkyl radicals (ii) or (het)aryl radicals (iii) specified as substituents for the R radicals;

joined together to form a saturated or unsaturated, 5- to 7-membered ring which comprises the nitrogen atom and whose carbon chain may be interrupted by one or more —O—, —S— and/or —$NR^4$— moieties, to which may be fused one or two unsaturated or saturated 4- to 8-membered rings whose carbon chain may likewise be interrupted by these moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the aforementioned radicals as substituents for alkyl, $C_1$-$C_{18}$-alkoxy, $C_1$-$C_{18}$-alkylthio and/or —$NR^5R^6$;

Z is —O— or —S—;

$R^3$ is one of the alkyl radicals (i) or (het)aryl radicals (iii) specified as substituents for the R radicals;

R' is $C_1$-$C_{30}$-alkyl whose carbon chain may be interrupted by one or more —O—, —S— and/or —$NR^4$— moieties and which may be mono- or polysubstituted by: $C_1$-$C_{12}$-alkoxy, $C_1$-$C_6$-alkylthio, —$NR^9R^{10}$, (het)aryl and/or $C_4$-$C_7$-cycloalkyl whose carbon skeleton may be interrupted by one or more —O—, —S— and/or —$NR^4$-moieties, where the cycloalkyl and (het)aryl radicals may be mono- or polysubstituted by $C_1$-$C_{18}$-alkyl and/or the above radicals specified as substituents for alkyl; aryl or hetaryl, to each of which may be fused further saturated or unsaturated 5- to 7-membered rings whose carbon skeleton may be interrupted by one or more —O—, —S— and/or —$NR^4$— moieties, where the entire ring system is mono- or polysubstituted by —$NR^9R^{10}$;

$R^4$ is hydrogen or $C_1$-$C_{18}$-alkyl, where the $R^4$ radicals may be the same or different when they occur more than once;

$R^5$, $R^6$ are each independently:

hydrogen;

$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^8$;

aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;

where the $R^5$ radicals may be the same or different when they occur more than once;

$R^7$ is $C_1$-$C_{18}$-alkyl whose carbon chain may be interrupted by one or more —O—, —S—, —CO—, —SO— and/or —$SO_2$— moieties and which may be mono- or polysubstituted by $C_r$ $C_{1-2}$-alkoxy, $C_1$-$C_6$-alkylthio, hydroxyl, mercapto, halogen, cyano, nitro and/or —$COOR^8$;

aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl, where the $R^7$ radicals may be the same or different when they occur more than once;

$R^8$ is $C_1$-$C_{18}$-alkyl;

$R^9$, $R^{10}$ are each $C_1$-$C_{30}$-alkyl whose carbon chain may be interrupted by one or more —O—, —S—, —$NR^4$—, —N=$CR^4$—, —C≡C—, —$CR^4$=$CR^4$—, —CO—, —SO— and/or —$SO_2$— moieties and which may be mono- or polysubstituted by: $C_1$-$C_{12}$-alkoxy, $C_1$-$C_6$-alkylthio, —C≡$CR^4$, —$CR^4$=$CR^4_2$, hydroxyl, —$NR^5R^6$, —$NR^5COR^6$, (het)aryl and/or saturated or unsaturated $C_4$-$C_7$-cycloalkyl whose carbon skeleton may be interrupted by one or more —O—, —S—, —$NR^4$—, —N=$CR^4$— and/or —$CR^4$=$CR^4$ moieties, where the (het)aryl and cycloalkyl radicals may each be mono- or polysubstituted by $C_1$-$C_{18}$-alkyl and/or the above radicals specified as substituents for alkyl;

aryl or hetaryl to which may be fused further saturated or unsaturated 5- to 7-membered rings whose carbon skeleton may be interrupted by one or more —O—, —S—, —$NR^4$—, —N=$CR^4$—, —$CR^4$=$CR^4$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^4$, —$CR^4$=$CR^4_2$, hydroxyl, —$NR^5R^6$, —$NR^5COR^6$, (het)aryl, (het)aryloxy and/or (het)arylthio, where the (het)aryl radicals may in each case be mono- or polysubstituted by $C_1$-$C_{18}$-alkyl, $C_1$-$C_{12}$-alkoxy, hydroxyl, —$NR^5R^6$ and/or —$NR^5COR^6$;

joined to the nitrogen atom to form a saturated or unsaturated, 5- to 7-membered ring whose carbon chain may be interrupted by one or more —O—, —S— and/or —$NR^4$-moieties, to which may be fused one or two unsaturated or saturated 4- to 8-membered rings whose carbon chain may likewise be interrupted by these moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/ or —NR⁵R⁶, (het)aryl which may be mono- or polysubstituted by $C_1$-$C_{18}$-alkyl and/or the above radicals specified as substituents for alkyl, $C_1$-$C_{18}$-alkoxy, $C_1$-$C_{18}$-alkylthio and/or —NR⁵R⁶;

m is 0, 1 or 2;

n is 0, 2 or 4 when m=0 or 1;
  is 0, 4 or 6 when m=2;

p is 0, 2 or 4 when m=0, where n+p=2 or 4;
  is 0, 2 or 4 when m=1, where n+p 0, 2 or 4, where, in the case that n+p=0 and one of the two Y radicals is a radical of the formula (y1) and the other radical is hydrogen, at least one of the two R¹ or R² radicals is one of the (het)aryl radicals (iii) specified as substituents for the R radicals when L is a chemical bond;
  is 0, 4 or 6 when m=2, where n+p=0, 4 or 6.

We have also rylene derivatives of the general formula Ib

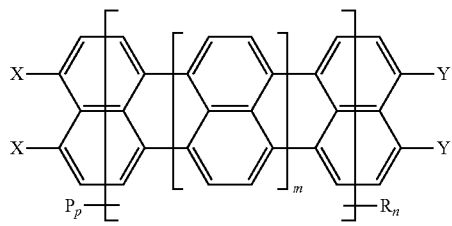

in which the variables are each defined as follows:

X are joined to one another with formation of a six-membered ring to give a radical of the formula (x2) or (x3)

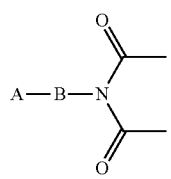

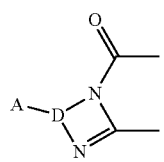

Y one of the two radicals is a radical of the formula (y1)

-L-NR¹R²    (y1)

or a radical of the formula (y2)

-L-Z—R³    (y2)

the other radical in each case is hydrogen;
are joined together with formation of a six-membered ring to give a radical of the formula (y3) or (y4)

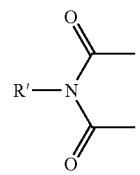

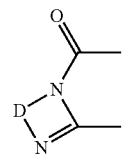

or both are hydrogen;

R are identical or different radicals:
  aryloxy, arylthio, hetaryloxy or hetarylthio, to each of which may be fused further saturated or unsaturated 5- to 7-membered rings whose carbon skeleton may be interrupted by one or more —O—, —S—, —NR⁴—, —N=CR⁴—, —CO—, —SO— and/or —SO₂— moieties, where the entire ring system may be mono- or polysubstituted by the (i), (ii), (iii), (iv) and/or (v) radicals:
  (i) $C_1$-$C_{30}$-alkyl whose carbon chain may be interrupted by one or more —O—, —S—, —NR⁴—, —N=CR⁴—, —C≡C—, —CR⁴=CR⁴—, —CO—, —SO— and/or —SO₂— moieties and which may be mono- or polysubstituted by: $C_1$-$C_{12}$-alkoxy, $C_1$-$C_6$-alkylthio, —C≡CR⁴, —CR⁴=CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂, —POR⁷R⁷, (het)aryl and/or saturated or unsaturated $C_4$-$C_7$-cycloalkyl whose carbon skeleton may be interrupted by one or more —O—, —S—, —CR⁴=CR⁴—, —CO—, —SO— and/or —SO₂— moieties, where the (het)aryl and cycloalkyl radicals may each be mono- or polysubstituted by $C_1$-$C_{18}$-alkyl and/or the above radicals specified as substituents for alkyl;
  (ii) $C_3$-$C_8$-cycloalkyl whose carbon skeleton may be interrupted by one or more —O—, —S—, —N=CR⁴—, —CR⁴=CR⁴—, —CO—, —SO— and/or —SO₂— moieties and to which may be fused further saturated or unsaturated 5- to 7-membered rings whose carbon skeleton may be interrupted by one or more —O—, —S—, —N=CR⁴—, —CR⁴=CR⁴—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴=CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂ and/or —POR⁷R⁷;
  (iii) aryl or hetaryl to which may be fused further saturated or unsaturated 5- to 7-membered rings whose carbon skeleton may be interrupted by one or more —O—, —S—, —N=CR⁴—, —CR⁴=CR⁴—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴=CR⁴₂, hydroxyl, mercapto, halogen, cyano, nitro, —NR⁹R¹⁰, —NR⁵COR⁶, —CONR⁵R⁶, —SO₂NR⁵R⁶, —COOR⁷, —SO₃R⁷, —PR⁷₂, —POR⁷R⁷, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, $C_1$-$C_6$-alkylthio, hydroxyl, mercapto, halogen, cyano, nitro, —$NR^9R^{10}$, —$NR^5COR^6$, —$CONR^5R^6$, —$SO_2NR^5R^6$, —$COOR^7$, —$SO_3R^7$, —$PR^7{}_2$ and/or —$POR^7R^7$;

(iv) a —U-aryl radical which may be mono- or polysubstituted by the above radicals specified as substituents for the aryl radicals (iii), where U is an —O—, —S—, —CO—, —SO— or —$SO_2$— moiety;

(v) $C_1$-$C_{12}$-alkoxy, $C_1$-$C_6$-alkylthio, —C≡$CR^4$, —$CR^4$=$CR^4{}_2$, hydroxyl, mercapto, halogen, cyano, nitro, —$NR^9R^{10}$, —$NR^5COR^6$, —$CONR^5R^6$, —$SO_2NR^5R^6$, —$COOR^7$, —$SO_3R^7$, —$PR^7{}_2$ and/or —$POR^7R^7$;

P is an amino radical —N'$R^2$;

B is $C_1$-$C_6$-alkylene, phenylene or combinations of these bridging members, where the phenylene radicals may be mono- or polysubstituted by $C_1$-$C_{12}$-alkyl, nitro, cyano and/or halogen;

A is —COOM, —$SO_3M$ or —$PO_3M$;

D is phenylene, naphthylene or pyridylene, each of which may be mono- or polysubstituted by $C_1$-$C_{12}$-alkyl, $C_1$-$C_{12}$-alkoxy, hydroxyl, nitro and/or halogen;

M is hydrogen, monovalent or divalent metal cation, especially alkaline earth metal or alkali metal cation, ammonium salts of cyclic amines, guanidinium salts or $[NR^5]_4^+$;

L is a chemical bond or an arylene or hetarylene radical, bonded to the rylene skeleton directly or via ethenylene or ethynylene, of the formulae —Ar—   —Ar-E-Ar— in which the (het)arylene radicals Ar may be the same or different, may comprise heteroatoms as ring atoms and/or may have fused saturated or unsaturated 5- to 7-membered rings which may likewise comprise heteroatoms, where the entire ring system may be mono- or polysubstituted by phenyl, $C_1$-$C_{12}$-alkyl, $C_1$-$C_{12}$-alkoxy, $C_1$-$C_{12}$-alkylthio and/or —$NR^5R^6$;

E is a chemical bond or an —O—, —S—, —$NR^4$—, —C≡C—, —$CR^4$=$CR^4$— or $C_1$-$C_6$-alkylene moiety;

$R^1$, $R^2$ are each independently one of the alkyl radicals (i), cycloalkyl radicals (ii) or (het)aryl radicals (iii) specified as substituents for the R radicals;

joined together to form a saturated or unsaturated, 5- to 7-membered ring which comprises the nitrogen atom and whose carbon chain may be interrupted by one or more —O—, —S— and/or —$NR^4$— moieties, to which may be fused one or two unsaturated or saturated 4- to 8-membered rings whose carbon chain may likewise be interrupted by these moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the aforementioned radicals as substituents for alkyl, $C_1$-$C_{18}$-alkoxy, $C_1$-$C_{18}$-alkylthio and/or —$NR^5R^6$;

Z is —O— or —S—;

$R^3$ is one of the alkyl radicals (i) or (het)aryl radicals (iii) specified as substituents for the R radicals;

R' is hydrogen;

$C_1$-$C_{30}$-alkyl whose carbon chain may be interrupted by one or more —O—, —S—, —$NR^4$—, —N=$CR^4$—, —C≡C—, —$CR^4$=$CR^4$—, —CO—, —SO— and/or —$SO_2$— moieties and which may be mono- or polysubstituted by the (ii), (iii), (iv) and/or (v) radicals specified as substituents for the R radicals;

$C_3$-$C_8$-cycloalkyl to which may be fused further saturated or unsaturated 5- to 7-membered rings whose carbon skeleton may be interrupted by one or more —O—, —S—, —$NR^4$—, —N=$CR^4$—, —$CR^4$=$CR^4$—, —CO—, —SO— and/or —$SO_2$— moieties, where the entire ring system may be mono- or polysubstituted by the (i), (ii), (iii), (iv) and/or (v) radicals specified as substituents for the R radicals; aryl or hetaryl to which may be fused further saturated or unsaturated 5- to 7-membered rings whose carbon skeleton may be interrupted by one or more —O—, —S—, —$NR^4$—, —N=$CR^4$—, —$CR^4$=$CR^4$—, —CO—, —SO— and/or —$SO_2$— moieties, where the entire ring system may be mono- or polysubstituted by the (i), (ii), (iii), (iv), (v) radicals specified as substituents for the R radicals, and/or aryl- and/or hetarylazo, each of which may be substituted by $C_1$-$C_{10}$-alkyl, $C_1$-$C_6$-alkoxy and/or cyano;

$R^4$ is hydrogen or $C_1$-$C_{18}$-alkyl, where the $R^4$ radicals may be the same or different when they occur more than once;

$R^5$, $R^6$ are each independently:

hydrogen;

$C_1$-$C_{18}$-alkyl whose carbon chain may be interrupted by one or more —O—, —S—, —CO—, —SO— and/or —$SO_2$— moieties and which may be mono- or polysubstituted by C alkoxy, $C_1$-$C_6$-alkylthio, hydroxyl, mercapto, halogen, cyano, nitro and/or —$COOR^8$; aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;

where the $R^5$ radicals may be the same or different when they occur more than once;

$R^7$ is $C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^8$;

aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;

where the $R^7$ radicals may be the same or different when they occur more than once;

$R^8$ is $C_1$-$C_{18}$-alkyl;

$R^7$, $R^8$ are each $C_1$-$C_{30}$-alkyl whose carbon chain may be interrupted by one or more —O—, —S—, —$NR^4$—, —N=$CR^4$—, —C≡C—, —$CR^4$=$CR^4$—, —CO—, —SO— and/or —$SO_2$— moieties and which may be mono- or polysubstituted by: $C_1$-$C_{12}$-alkoxy, $C_1$-$C_6$-alkylthio, —C≡$CR^4$, —$CR^4$=$CR^4{}_2$, hydroxyl, —$NR^5R^6$, —$NR^5COR^6$, (het)aryl and/or saturated or unsaturated $C_4$-$C_7$-cycloalkyl whose carbon skeleton may be interrupted by one or more —O—, —S—, —$NR^4$—, —N=$CR^4$— and/or —$CR^4$=$CR^4$ moieties, where the (het)aryl and cycloalkyl radicals may each be mono- or polysubstituted by $C_1$-$C_{18}$-alkyl and/or the above radicals specified as substituents for alkyl; aryl or hetaryl to which may be fused further saturated or unsaturated 5- to 7-membered rings whose carbon skeleton may be interrupted by one or more —O—, —S—, —$NR^4$—, —N=$CR^4$—, —CR⁴=CR⁴—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡CR⁴, —CR⁴=CR⁴₂, hydroxyl, —NR⁵R⁶, —NR⁵COR⁶, (het)aryl, (het)aryloxy and/or (het)arylthio, where the (het)aryl radicals may in each case be mono- or polysubstituted by $C_1$-$C_{18}$-alkyl, $C_1$-$C_{12}$-alkoxy, hydroxyl, —NR⁵R⁶ and/or —NR⁵COR⁶;

joined to the nitrogen atom to form a saturated or unsaturated, 5- to 7-membered ring whose carbon chain may be interrupted by one or more —O—, —S— and/or —NR⁴-moieties, to which may be fused one or two unsaturated or saturated 4- to 8-membered rings whose carbon chain may likewise be interrupted by these moieties and/or —N=, where the entire ring system may be mono- or polysubstituted by: $C_1$-$C_{24}$-alkyl which may be substituted by $C_1$-$C_{18}$-alkoxy, $C_1$-$C_{18}$-alkylthio and/or —NR⁵R⁶, (het)aryl which may be mono- or polysubstituted by $C_1$-$C_{18}$-alkyl and/or the above radicals specified as substituents for alkyl, $C_1$-$C_{18}$-alkoxy, $C_1$-$C_{18}$-alkylthio and/or —NR⁵R⁶;

m is 0, 1 or 2;

n is 0, 2 or 4 when m=0 or 1;
  is 0, 4 or 6 when m=2;

p is 0, 2 or 4 when m=0, where n+p=2 or 4 or may also be 0 when one of the two Y radicals is a radical of the formula (y1) or (y2) and the other radical is hydrogen, where at least one of the two $R^1$ or $R^2$ radicals in the (y1) radical is one of the (het)aryl radicals (iii) specified as substituents for the R radicals when L is a chemical bond;
  is 0, 2 or 4 when m=1, where n+p=0, 2 or 4;
  is 0, 4 or 6 when m=2, where n+p=0, 4 or 6.

The rylene derivatives I are unsymmetrical perylene-, terrylene- and quaterrylenetetra- and -dicarboxylic acid derivatives. Particular preference is given to the perylene and terrylene derivatives.

The rylene derivatives I are acid-functionalized at one end of the molecule (3,4-position). The X radicals are joined together with formation of a six-membered ring to give a radical of the formula (x1), (x2) or (x3)

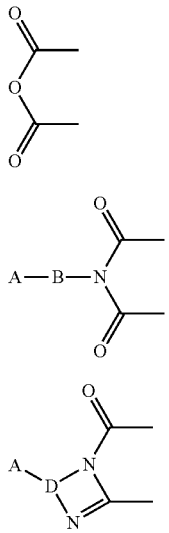

The rylene derivatives I may be present not only in anhydride form (x1) but also as free acids or as salts (both X radicals a —COOM radical). Suitable salts are salts derived from mono- or divalent metal ions and complexes thereof, especially, as well as the guanidinium salts, the heterocyclic ammonium salts, ammonium salts (both $NH_4^+$ and tetraalkyl/arylammonium $[NR^5]_4^+$ with identical or different $R^5$ radicals), in particular the alkali metal salts and alkaline earth metal salts.

In the imide radicals (x2), acid groups A are bonded to the imide nitrogen atom via a bridging member B.

Suitable bridging members B are $C_1$-$C_6$-alkylene radicals and phenylene radicals and combinations of these radicals, for example alkylenephenylene, phenylenealkylene and alkylenephenylenealkylene radicals. The phenylene radicals may be mono- or polysubstituted by $C_1$-$C_{12}$-alkyl, $C_1$-$C_6$-alkoxy, hydroxyl, nitro, cyano and/or halogen, but they are preferably unsubstituted.

The acid groups A are carboxyl, sulfo or phosphonic acid groups which may likewise be present as the free acid or in salt form.

In the condensate radicals (x3) which are formed by condensation of the dicarboxylic anhydride with an acid-containing o-phenylenediamine, 1,8-diaminonaphthalene or else 3,4-diaminopyridine, the acid group A, which may again be present in salt form, is bonded to the aromatic ring system D. The ring system D is otherwise preferably unsubstituted, but may also bear $C_1$-$C_{12}$-alkyl, $C_1$-$C_6$-alkoxy, hydroxyl, nitro and/or halogen as substituents.

Particularly preferred rylene derivatives I have an anhydride radical (x1) or the corresponding dicarboxylic acid salt in the 3,4-position.

The rylene derivatives I may be unsubstituted at the other end of the molecule (both Y radicals hydrogen) or be substituted in the peri-position by an amino radical (y1)

or a (thio)ether radical (y2)

(the second Y radical is accordingly hydrogen) or be present as the imide (y3) or condensate (y4)

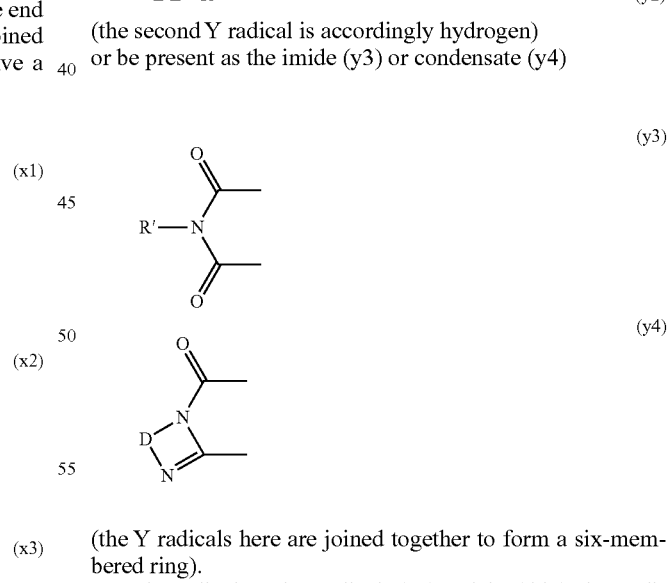

(the Y radicals here are joined together to form a six-membered ring).

In the radicals amino radicals (y1) and the (thio)ether radicals (y2), the amine function or the (thio)ether function is bonded to the rylene skeleton via a bridging member L.

The bridging member L may be a chemical bond, i.e. the amino group is bonded directly to the rylene skeleton, or a (het)arylene radical, bonded to the rylene skeleton directly or via ethenylene or ethynylene, of the formulae

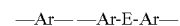

The (het)arylene radicals Ar may comprise heteroatoms as ring atoms and/or fused saturated or unsaturated 5- to 7-membered rings which may likewise comprise heteroatoms. When they are fused ring systems Ar, the bonds to the rylene skeleton and to the functional group may both start from the same ring or from different rings. The whole ring system may additionally be mono- or polysubstituted by phenyl, $C_1$-$C_{12}$-alkyl, $C_1$-$C_{12}$-alkoxy, $C_1$-$C_{12}$-alkylthio and/or —$NR^5R^6$, preference being given to $C_1$-$C_{12}$-alkyl, $C_1$-$C_{12}$-alkoxy and/or —$NR^5R^6$ as substituents.

When the bridging member L comprises two (het)arylene radicals Ar, they are preferably the same, but may also be different. The two Ar radicals may be bonded directly to one another or joined together via an —O—, —S—, —$NR^4$—, —C≡C—, —$CR^4$=$CR^4$— or $C_1$-$C_6$-alkylene moiety. The bonding member E is preferably a chemical bond or an —O—, —S—, —$NR^4$— or —C moiety.

Examples of suitable bridging members L include:

1,4-, 1,3- and 1,2-phenylene, 1,4- and 1,8-naphthylene, 1,4- and 2,3-pyrrylene, 2,5-, 2,4- and 2,3-thienylene, 2,5-, 2,4- and 2,3-furanylene, 2,3-, 2,4-, 2,5-, 2,6-, 3,4- and 3,5-pyridinylene, 2,3-, 2,5-, 2,6-, 3,7-, 4,8-, 5,8- and 6,7-quinolinylene, 2,7-, 3,6-, 4,5-, 2,6-, 3,7-, 4,7- and 4,8-isoquinolinylene, 4,4'-, 3,3'- and 2,2'-biphenylene, 3,3'- and 2,2'-bithienylene, 1,4-[2,5-di(tert-butyl)]phenylene, 1,4-(2,5-dihexyl)phenylene, 1,4-[2,5-di(tert-octyl)]phenylene, 1,4-(2,5-didodecyl)phenylene, 1,4-[2,5-di(2-dodecyl)]-phenylene, 4,4'-di(2,2',6,6'-tetramethyl)phenylene, 4,4'-di(2,2',6,6'-tetraethyl)phenylene, 4,4'-di(2,2',6,6'-tetraisopropyl)phenylene, 4,4'-di(2,2',6,6'-tetrahexyl)phenylene, 4,4'-di[2,2',6,6'-tetra(2-hexyl)]phenylene, 4,4'-di[2,2',6,6'-tetra(tert-octyl)]phenylene, 4,4'-di(2,2',6,6'-tetradodecyl)phenylene and 4,4'-di[2,2',6,6'-tetra(2-dodecyl)]phenylene, and also

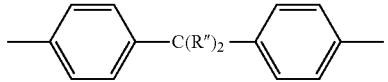

where R" is hydrogen, methyl, ethyl or phenyl.

Very particularly preferred bridging members L are a chemical bond, 1,4-phenylene, 2,3-thienylene and 4,4'-di(2,2',6,6'-tetramethyl)phenylene.

The $R^1$ and $R^2$ radicals in the amino radical (y1) may each independently be one of the alkyl radicals (i), cycloalkyl radicals (ii) or (het)aryl radicals (iii) mentioned at the outset as substituents in the definition of the variable $R^1$. The $R^1$ and $R^2$ radicals are preferably in particular identical phenyl radicals which may bear, as substituents, $C_1$-$C_{18}$-alkyl, $C_1$-$C_{12}$-alkoxy, $C_1$-$C_6$-alkylthio, —$NR^5R^6$, and/or phenoxy and/or phenylthio, each of which may be mono- or polysubstituted by $C_1$-$C_{18}$-alkyl, $C_1$-$C_{12}$-alkoxy, $C_1$-$C_6$-alkylthio, —$NR^5R^6$. They are preferably substituted in the para-position by $C_4$-$C_{18}$-alkyl, especially branched $C_4$-$C_{18}$-alkyl, for example tert-octyl, $C_1$-$C_{18}$-alkoxy, for example methoxy, or di($C_1$-$C_{18}$-alkyl)amino, for example dimethylamino, or are unsubstituted.

The $R^1$ and $R^2$ radicals may also be joined together to give a saturated or unsaturated, 5- to 7-membered ring which comprises the nitrogen atom of the amino radical (y1) and whose carbon skeleton may be interrupted by one or more —O—, —S— and/or —$NR^4$-moieties ($R^4$: H or $C_1$-$C_{18}$-alkyl, preferably H or $C_1$-$C_6$-alkyl), to which may be fused one or two unsaturated or saturated, 4- to 8-membered rings whose carbon chain may likewise be interrupted by these moieties and/or —N=, where the entire ring system may be mono- or polysubstituted by: $C_1$-$C_{24}$-alkyl, which may be substituted by $C_1$-$C_{18}$-alkoxy, $C_1$-$C_{18}$-alkylthio and/or —$NR^5R^6$, (het)aryl which may be mono- or polysubstituted by $C_1$-$C_{18}$-alkyl and/or the aforementioned radicals mentioned as substituents for alkyl, $C_1$-$C_{18}$-alkoxy, $C_1$-$C_{18}$-alkylthio and/or —$NR^5R^6$, preference being given to $C_4$-$C_{18}$-alkyl, $C_1$-$C_{18}$-alkoxy and —$NR^5R^6$ as substituents.

Examples of preferred unsubstituted cyclic amino radicals include piperidyl, pyrrolidyl, piperazyl, morpholinyl, thiomorpholinyl, pyrryl, dibenzopyrryl (carbazyl), dibenzo-1,4-oxiranyl (phenoxazinyl), dibenzo-1,4-thiazinyl (phenothiazinyl), dibenzo-1,4-pyrazyl (phenazinyl) and dibenzopiperidyl, particular preference being given to piperidyl, pyrrolidinyl, dibenzopyrryl, dibenzo-1,4-oxiranyl, dibenzo-1,4-thiazinyl, dibenzo-1,4-pyrazyl and dibenzopiperidyl and very particular preference to phenothiazinyl, piperidyl and pyrrolidyl.

The reactants used for these cyclic amino radicals are the corresponding cyclic amines or salts thereof. Examples of suitable substituted and unsubstituted amines include:

piperidine, 2- or 3-methylpiperidine, 6-ethylpiperidine, 2,6- or 3,5-dimethylpiperidine, 2,2,6,6-tetramethylpiperidine, 4-benzylpiperidine, 4-phenylpiperidine, piperidin-4-ol, 2,2,6,6-tetramethylpiperidin-4-ylamine, decahydroquinoline and decahydroisoquinoline;

pyrrolidine, 2-methylpyrrolidine, 2,5-dimethylpyrrolidin, 2,5-diethylpyrrolidine, tropanol, pyrrolidin-3-ylamine, (2,6-dimethylphenyl)pyrrolidin-2-ylmethylamine, (2,6-diisopropylphenyl)pyrrolidin-2-ylmethylamine and dodecahydrocarbazole;

piperazine, diketopiperazine, 1-benzylpiperazine, 1-phenethylpiperazine, 1-cyclohexylpiperazine, 1-phenylpiperazine, 1-(2,4-dimethylphenyl)piperazine, 1-(2-, 3- or 4-methoxyphenyl)piperazine, 1-(2-, 3- or 4-ethoxyphenyl)piperazine, 1-(2-, 3- or 4-fluorophenyl)piperazine, 1-(2-, 3- or 4-chlorophenyl)piperazine, 1-(2-, 3- or 4-bromophenyl)piperazine, 1-, 2- or 3-pyridin-2-ylpiperazine and 1-benzo[1,3]dioxol-4-ylmethylpiperazine;

morpholine, 2,6-dimethylmorpholine, 3,3,5,5-tetramethylmorpholine, morpholine-2- or -3-ylmethanol, 3-benzylmorpholine, 3-methyl-2-phenylmorpholine, 2- or 3-phenylmorpholine, 2-(4-methoxyphenyl)morpholine, 2-(4-trifluoromethylphenyl)morpholine, 2-(4-chlorophenyl)morpholine, 2-(3,5-dichlorophenyl)morpholine, 3-pyridin-3-yl-morpholine, 5-phenylmorpholin-2-one, 2-morpholin-2-ylethylamine and phenoxazine;

thiomorpholine, 2- or 3-phenylthiomorpholine, 2- or 3-(4-methoxyphenyl)thiomorpholine, 2- or 3-(4-fluorophenyl)thiomorpholine, 2- or 3-(4-trifluoromethylphenyl)thiomorpholine, 2- or 3-(2-chlorophenyl)thiomorpholine, 4-(2-aminoethyl)thiomorpholine, 3-pyridin-3-ylthiomorpholine, 3-thiomorpholinone and 2-phenylthiomorpholin-3-one, and also the thiomorpholine oxides and dioxides.

Examples of particularly preferred (y1) radicals are:

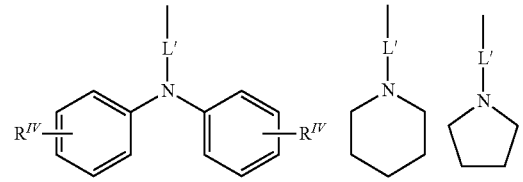

-continued

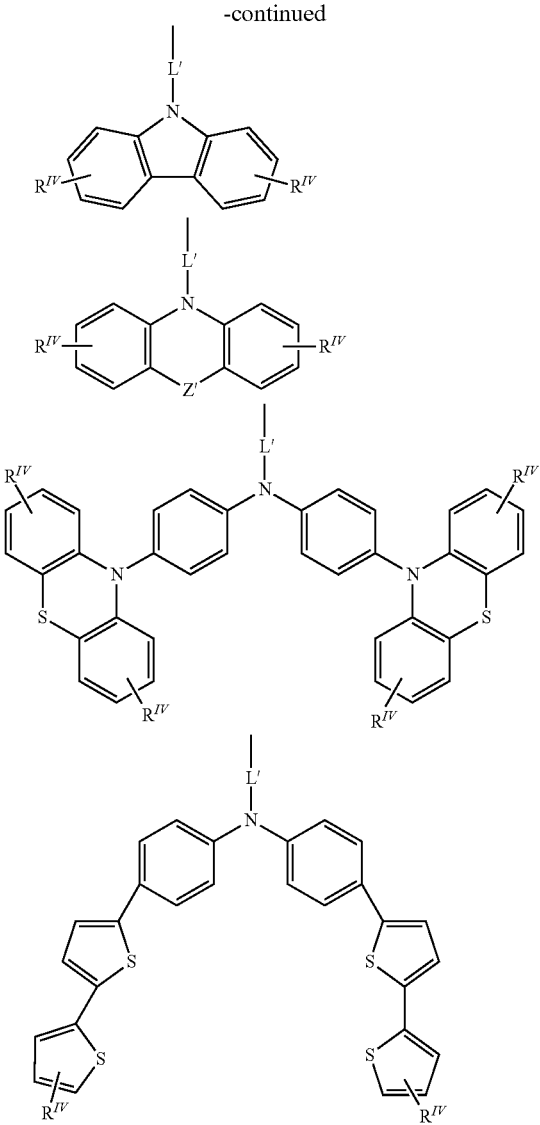

where the variables are defined as follows:
L' is a chemical bond or 1,4-phenylene;
Z' is —O—, —S—, —NR$^{8'}$ or —CH$_2$—, where R$^{8'}$ is C$_1$-C$_{18}$-alkyl;
R$^{IV}$ is C$_4$-C$_{18}$-alkyl, C$_1$-C$_{18}$-alkoxy, (hetero)aryl or —NR$^5$R$^6$.

Very particularly preferred amino radicals (y1) are the diphenylaminophenylene and especially the diphenylamino radicals detailed above.

For the (thio)ether radical (y2), particularly preferred bridging members L are a chemical bond, 1,4-phenylene and 2,5-thienylene. A very particularly preferred bridging member L is the chemical bond.

The R$^3$ radical in the (thio)ether radical (y2) may be one of the alkyl radicals (i) or (het)aryl radicals (iii) mentioned at the outset as substituents in the definition of the variables R.

R$^3$ is preferably:
C$_1$-C$_{30}$-alkyl whose carbon chain may be interrupted by one or more —O—, —S— and/or —NR$^4$— moieties and which may be mono- or polysubstituted by: C$_1$-C$_{12}$-alkoxy, hydroxyl and/or aryl which may be mono- or polysubstituted by C$_1$-C$_{18}$-alkyl or C$_1$-C$_6$-alkoxy; phenyl which may be mono- or polysubstituted by: C$_1$-C$_{18}$-alkyl, C$_1$-C$_{12}$-alkoxy, C$_1$-C$_6$-alkylthio, —NR$^5$R$^6$ and/or phenoxy and/or phenylthio, each of which may be mono- or polysubstituted by C$_1$-C$_{18}$-alkyl, C$_1$-C$_{12}$-alkoxy, C$_1$-C$_6$-alkylthio and/or —NR$^5$R$^6$.

Examples of particularly preferred (y2) radicals are:
phenoxy, phenylthio, naphthyloxy and/or naphthylthio, each of which may be mono- or polysubstituted by C$_4$-C$_{18}$-alkyl, C$_1$-C$_{18}$-alkoxy and/or —NR$^5$R$^6$.

In the imide radicals (y3), R', in addition to hydrogen, may be the alkyl radicals (i), cycloalkyl radicals (ii) or (het)aryl radicals (iii) defined at the outset.

R' is preferably defined as follows:
C$_6$-C$_{30}$-alkyl whose carbon chain may be interrupted by one or more —O—, —S— and/or —NR$^4$— moieties and which may be mono- or polysubstituted by: C$_1$-C$_6$-alkoxy, C$_1$-C$_6$-alkylthio, —NR$^9$R$^{10}$ and/or aryl which may be mono- or polysubstituted by C$_1$-C$_{18}$-alkyl or C$_1$-C$_6$-alkoxy, particular preference being given to C$_6$-C$_{30}$-alkyl which is substituted in the ω-position by —NR$^9$R$^{10}$;

(het)aryl, especially phenyl, naphthyl, pyridyl or pyrimidyl, in particular phenyl, each of which may be mono- or polysubstituted by: C$_1$-C$_{18}$-alkyl, C$_1$-C$_6$-alkoxy, halogen, cyano, nitro, —NR$^9$R$^{10}$, —CONR$^5$R$^6$, —SO$_2$NR$^5$R$^6$ and/or phenoxy, phenylthio, phenylazo and/or naphthylazo, each of which may be substituted by C$_1$-C$_{10}$-alkyl, C$_1$-C$_6$-alkoxy and/or cyano.

Most preferably, R' is a phenyl radical which is mono- or polysubstituted by C$_1$-C$_{18}$-alkyl or —NR$^9$R$^{10}$.

The R$^5$ and R$^5$ radicals are each as defined at the outset. They are preferably each independently:
hydrogen;
C$_1$-C$_{18}$-alkyl which may be mono- or polysubstituted by C$_1$-C$_6$-alkoxy, hydroxyl, halogen and/or cyano;
aryl or hetaryl, each of which may be mono- or polysubstituted by C$_1$-C$_6$-alkyl and/or the above radicals mentioned as substituents for alkyl.

Particularly suitable substituents are the alkyl radicals and in particular the amino groups —NR$^9$R$^{10}$.

The definition of the R$^9$ and R$^{10}$ radicals is likewise given at the outset. They are preferably each independently:
C$_1$-C$_{30}$-alkyl whose carbon chain may be interrupted by one or more —O—, —S—, —N=CR$^4$—, —C and/or —CR$^4$=CR$^4$— moieties and which may be mono- or polysubstituted by: C$_1$-C$_{12}$-alkoxy, C$_1$-C$_6$-alkylthio, —C≡CR$^4$, —CR$^4$=CR$^4{}_2$, hydroxyl, —NR$^5$R$^6$, —NR$^5$COR$^6$ and/or (het)aryl which may be mono- or polysubstituted by C$_1$-C$_{18}$-alkyl and/or the above radicals mentioned as substituents for alkyl; aryl or hetaryl, to which may be fused further saturated or unsaturated 5- to 7-membered rings whose carbon skeleton may be interrupted by one or more —O—, —S—, —NR$^4$—, —N=CR$^4$—, —CR$^4$=CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^4$, —CR$^4$=CR$^4{}_2$, hydroxyl, —NR$^5$R$^6$, —NR$^5$COR$^6$, (het)aryl, (het)aryloxy and/or (het)arylthio, where the (het)aryl radicals may each be mono- or polysubstituted by C$_1$-C$_{18}$-alkyl, C$_1$-C$_{12}$-alkoxy, hydroxyl, —NR$^5$R$^6$ and/or —NR$^5$COR$^6$;

joined to the nitrogen atom to give a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by C$_1$-C$_{24}$-alkyl which may be substituted by C$_1$-C$_{18}$-alkoxy, C$_1$-C$_{18}$-alkylthio and/or —NR$^5$R$^6$.

The amino groups —NR$^9$R$^{10}$ are preferably di(het)arylamino groups or cyclic amino groups. Particular preference is given to diphenylamino groups in which the phenyl radicals may be unsubstituted or may have the above substituents, especially the alkyl radicals, preferably in the p-position.

Preferred substitution patterns for the phenyl radicals R' are ortho,ortho'-disubstitution (for example alkyl radicals with a secondary carbon atom in the 1-position) and para-substitution (for example alkyl radicals having a tertiary carbon atom in the 1-position and at least 5 carbon atoms or amino groups —NR$^9$R$^{10}$).

Examples of particularly preferred R' radicals are:

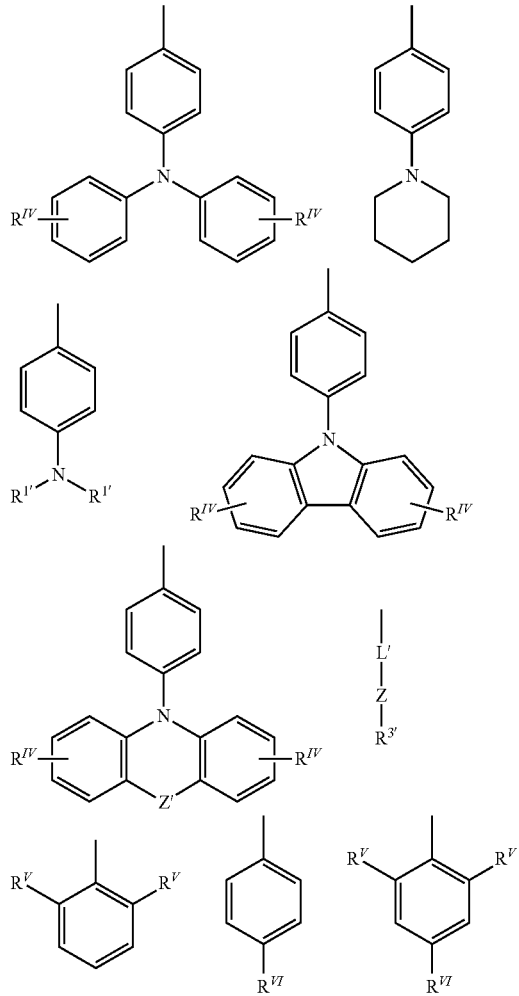

where the variables are each defined as follows:

R$^{IV}$ is C$_4$-C$_{18}$-alkyl or C$_1$-C$_{18}$-alkoxy;
R$^V$ is C$_3$-C$_8$-alkyl with a secondary carbon atom in the 1-position;
R$^{VI}$ is C$_4$-C$_{18}$-alkyl with a tertiary carbon atom in the 1-position or —NR$^9$R$^{10}$;
R$^{1'}$ is C$_1$-C$_{18}$-alkyl;
R$^{3'}$ is phenyl when L' is a chemical bond;
C$_4$-C$_{18}$-alkyl when L' is 1,4-phenylene;
L' is a chemical bond, 1,4-phenylene or 2,5-thienylene;
Z' is —O—, —S—, —NR$^8$— or —CH$_2$—, where R$^8$ is C$_1$-C$_{18}$-alkyl;
Z is —O— or —S—.

Very particularly preferred R' radicals are the diphenylaminophenylene radicals.

The condensate radicals (y4) are formed by condensation of the anhydride with aromatic diamines, substituted if desired, especially with o-phenylenediamine or 1,8-diaminonaphthalene or else 3,4-diaminopyridine.

Preference is given to rylene derivatives I in which one of the two Y radicals is a (y1) or (y2) radical and the other radical is hydrogen or both Y radicals are an imide radical (y3), the abovementioned further preferences applying.

Particular preference is given to rylene derivatives I in which one of the two Y radicals is a (y1) or (y2) radical and the other radical is hydrogen.

The rylene derivatives I are preferably additionally substituted in the rylene skeleton. Preference is given to tetrasubstitution in the 1,6,7,12-position in the perylene derivatives, 1,6,9,14-position in the terrylene derivatives and 1,6,11,16-position in the quaterrylene derivatives. In the perylene and terrylene derivatives, disubstitution in the 1,6- and/or 1,7-position and 1,6- or 9,14-position respectively is also possible, as is hexasubstitution in the 1,6,8,11,16,18,19-position in the quaterrylene derivatives. The counting here always begins at the end of the molecule with the X radicals.

In general, the rylene derivatives I are present in the form of mixtures of products with a different degree of substitution, in which the tetrasubstituted, or di- or hexasubstituted, products make up the main constituent. Since the substituents are typically introduced into the rylene skeleton by nucleophilic substitution of halogenated, especially brominated, rylene derivatives I or correspondingly halogenated precursors, the rylene derivatives I may still comprise traces of halogen which, if desired, can be removed by transition metal-catalyzed reductive or base-induced dehalogenation.

Suitable substituents are especially the (het)aryloxy and (het)arylthio radicals R defined at the outset. Particularly suitable substituents are phenoxy, thiophenoxy, pyridyloxy, primidylthio, pyridylthio and pyrimidylthio radicals. The R radicals may correspond to radicals of the formula (y2).

Preferred R radicals are phenoxy or thiophenoxy radicals, each of which may be mono- or polysubstituted by identical or different (i), (ii), (iii), (iv) and/or (v) radicals:

(i) C$_1$-C$_{30}$-alkyl whose carbon chain may be interrupted by one or more —O—, —S—, —NR$^4$—, —C≡C—, —CR$^4$═CR$^4$— and/or —CO— and/or —SO$_2$— moieties and which may be mono- or polysubstituted by: C$_1$-C$_{12}$-alkoxy, hydroxyl, halogen, cyano, and/or aryl which may be mono- or polysubstituted by C$_1$-C$_{18}$-alkyl or C$_1$-C$_6$-alkoxy;

(ii) C$_3$-C$_8$-cycloalkyl whose carbon skeleton may be interrupted by one or more —O—, —S—, —NR$^4$—, —N═CR$^4$—, —CR$^4$═CR$^4$— and/or —CO— moieties and which may be mono- or polysubstituted by: C$_1$-C$_{18}$-alkyl, C$_1$-C$_{12}$-alkoxy and/or C$_1$-C$_6$-alkylthio;

(iii) aryl or hetaryl, to which may be fused further saturated or unsaturated 5- to 7-membered rings whose carbon skeleton may be interrupted by one or more —O—, —S—, —NR$^4$—, —N═CR$^4$—, —CR$^4$═CR$^4$—, —CO—, —SO— and/or —SO$_2$— moieties, where the entire ring system may be mono- or polysubstituted by: C$_1$-C$_{18}$-alkyl, C$_1$-C$_{12}$-alkoxy, —C☐CR$^4$$_2$, —CR$^4$═CR$^4$$_2$, hydroxyl, halogen, cyano, —NR$^9$R$^{10}$, —NR$^5$COR$^6$, —CONR$^5$R$^6$, —SO$_2$NR$^5$R$^6$, —COOR$^7$ and/or —SO$_3$R$^7$, (het)aryl, (het)aryloxy and/or (het)arylthio, where the (het)aryl radicals may each be mono- or polysubstituted by C$_1$-C$_{18}$-alkyl, C$_1$-C$_{18}$-alkoxy and/or cyano;

(iv) a —U-aryl radical which may be mono- or polysubstituted by the above radicals specified as substituents for the aryl radicals (iii), where U is an —O—, —S—, —NR$^4$—, —CO—, —SO— or —SO$_2$— moiety;

(v) $C_1$-$C_{12}$-alkoxy, $C_1$-$C_6$-alkylthio, —C≡CR$^4$, —CR$^4$=CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$ or —SO$_3$R$^7$.

The (thio)phenoxy radicals R may be unsubstituted or monosubstituted in the ortho-, meta- or preferably para-position. They may also be di-, tri-, tetra- or pentasubstituted, all substitution patterns being conceivable.

In addition, the rylene skeleton of the rylene derivatives I may also be substituted by P radicals. These are amino radicals —NR$^1$R$^2$. The P radicals therefore correspond to (y1) radicals in which L is a chemical bond.

The rylene derivatives I may simultaneously be substituted by (het)aryloxy or -thio radicals R and cyclic amino groups P, or either by R radicals or by P radicals. However, they are preferably substituted only by R radicals.

The above-described preferred definitions for the variables occurring in formula I apply equally to the novel rylene derivatives Ia and Ib.

Specific examples of the R, R' to R$^{VI}$ and R$^1$ to R$^{10}$ radicals occurring in the inventive formulae and their substituents include:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 1- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl; 2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butyl-phenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine; phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2-, 3- and 4-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 544-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Some of the inventive rylene derivatives I which have one anhydride radical (x1) and one imide radical (y3) or one condensate radical (y4) are known (WO-A-02/66438, Chem. Eur. J. 11, p. 1-9 (2005) and the prior German patent applications 10 2005 021 362.6 and 10 2005 032 583.1).

The preparation of the novel rylene derivatives Ia and Ib can advantageously be undertaken by the processes described below.

The assistants used, such as solvents, bases, catalysts, etc., can of course, even without any explicit reference thereto, always also be used in the form of mixtures.

The crude products obtained in each case can, if desired, be subjected to an additional purification by column filtration or column chromatography on silica gel with nonpolar organic solvents such as hexane or pentane, or polar organic solvents, especially halogenated hydrocarbons such as methylene chloride and chloroform, or in particular with mixtures of nonpolar and polar solvents.

A. Preparation of Rylene Derivatives Ia

To prepare the rylene derivatives Ia in which one Y radical is an amino radical (y1) or a (thio)ether radical (y2) and the other Y radical is hydrogen, it is possible to react peri-halorylenedicarboxylic anhydrides of the formula IIa

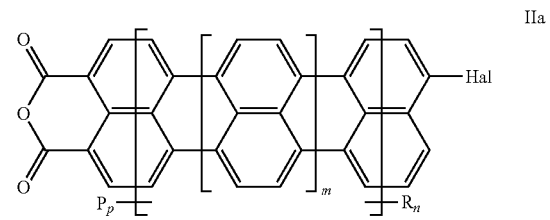

or peri-halorylenedicarboximides of the formula IIb

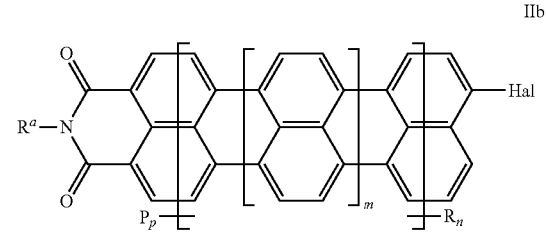

in which $R^a$ is one of the alkyl radicals (i) or cycloalkyl radicals (ii) mentioned at the outset as substituents for the R radicals, and Hal is iodine, preferably chlorine and more preferably bromine, with the reactants (III) comprising the particular (y1) or (y2) radical.

The reaction conditions depend upon the bridging member L present in each case in the (y1) and (y2) radicals and are described below separately.

When peri-halorylenedicarboximides IIb are used for the reaction with the reactant (III), which can ease the reaction owing to their better solubility, the peri-substituted rylenedicarboximides of the formula IIb'

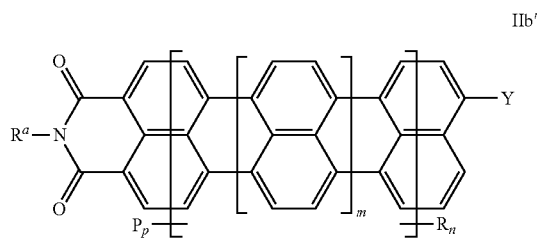

IIb' obtained in each case still have to be hydrolyzed to the rylenedicarboxylic anhydride Ia.

The alkaline hydrolysis can be carried out in polar organic solvents under comparable conditions for all rylenedicarboximides IIb'.

Suitable reaction media are especially protic polar organic solvents. Particularly suitable solvents are aliphatic alcohols which have from 3 to 8 carbon atoms and may be unbranched, but are preferably branched. Examples include, in addition to n-propanol and n-butanol, especially isopropanol, sec- and tert-butanol and 2-methyl-2-butanol.

In general, from 5 to 500 ml, preferably from 20 to 100 ml of solvent are used per g of IIb'.

Suitable bases are alkali metal and alkaline earth metal bases, preference being given to the alkali metal bases and particular preference to the sodium and potassium bases. Suitable bases are both inorganic bases, in particular the hydroxides such as sodium hydroxide and potassium hydroxide, and organic bases, in particular the alkoxides such as sodium methoxide, potassium methoxide, potassium isopropoxide and potassium tert-butoxide, which are typically used in anhydrous form. Very particular preference is given to potassium hydroxide.

In general, from 10 to 200 mol, preferably from 30 to 70 mol of base are required per mole of IIb'.

Especially in the hydrolysis of the terrylenedicarboximides IIb', it has been found to be advantageous to additionally use a metal fluoride, especially an alkali metal fluoride, for example potassium fluoride, sodium fluoride or lithium fluoride, as an assistant.

Suitable amounts of assistant are generally from 0.1 to 2 mol, in particular from 0.7 to 1.3 mol per mole of base.

The reaction temperature is generally from 50 to 120° C., preferably from 60 to 100° C.

Typical reaction times are from 0.5 to 24 h, in particular from 2 to 10 h.

In process technology terms, the procedure is appropriately as follows:

A mixture of base, if appropriate assistant and solvent is heated to the reaction temperature with vigorous stirring and the rylenedicarboximide IIb' is then added. After the desired reaction time, an acid, for example an inorganic acid such as hydrochloric acid or preferably an organic acid such as acetic acid, is added dropwise until a pH of from about 1 to 4 has been attained, and the mixture is stirred at the reaction temperature for a further 1 to 4 h. The reaction product precipitated by diluting with water after cooling to room temperature is filtered off, washed with hot water and dried at about 100° C. under reduced pressure.

When, instead of the particular anhydride, the corresponding carboxylic acid salt is to be isolated, the procedure is appropriately not to acidify the reaction mixture after the hydrolysis but rather just to cool it to room temperature, filter off the precipitated product, wash with a lower aliphatic alcohol such as isopropanol and dry at about 100° C. under reduced pressure.

A.1 Preparation of Rylene Derivatives of the Formula Ia1

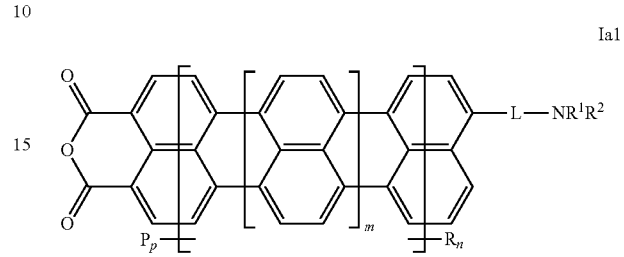

Ia1

The preparation of the rylene derivatives Ia1 is described in sections below as a function of the particular bridging member L.

A.1.1. Preparation of Rylene Derivatives of the Formula Ia11 (L=Chemical Bond)

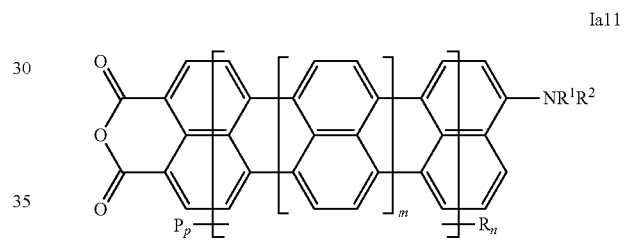

Ia11

To prepare the rylene derivatives Ia11, it is possible to react a) the peri-halorylenedicarboxylic anhydride IIa or b) the peri-halorylenedicarboximide IIb, in the presence of an aprotic organic solvent and, if desired, of a base or of a combination of a transition metal catalyst and of a base, with an amine of the formula IIIa

IIIa, which should be followed by the above-described hydrolysis in case b). The hydrolysis and the nucleophilic substitution can also be performed in a one-pot reaction.

When the reaction is undertaken in the presence of the transition metal catalyst, it is generally possible to work at lower reaction temperatures and with smaller amounts of amine reactant IIIa.

Suitable organic solvents are in principle all aprotic solvents which are stable under the reaction conditions and have a boiling point above the selected reaction temperature, in which the rylene reactants IIa or IIb and the amine IIIa dissolve fully and the catalysts and bases used if appropriate at least partially, so that substantially homogeneous reaction conditions are present. It is possible to use either polar or nonpolar aprotic solvents, preference being given to polar solvents especially when no transition metal catalyst is used. When the amine IIIa used is liquid at the reaction temperature, it may even itself serve as the reaction medium, and the use of a solvent can be omitted.

Examples of suitable polar aprotic solvents are in particular N,N-disubstituted aliphatic carboxamides (especially N,N-di-$C_1$-$C_4$-alkyl-$C_1$-$C_4$-carboxamides), nitrogen heterocycles without NH functions, dimethyl sulfoxide and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of particularly suitable solvents include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; dimethyl sulfoxide; tetrahydrofuran, di- and tetramethyltetrahydrofuran, dioxane, diphenyl ether, the dimethyl, diethyl, dipropyl, diisopropyl, di-n-butyl, di-sec-butyl and di-tert-butyl ethers of diethylene glycol, diethylene glycol methyl ethyl ether, the dimethyl and diethyl ethers of triethylene glycol, and triethylene glycol methyl ethyl ether, preference being given to dimethylformamide and tetrahydrofuran.

Examples of suitable nonpolar aprotic solvents are solvents having a boiling point of >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having form 10 to 18 carbon atoms), alkyl- and cycloalkyl-substituted aromatics (especially benzene which is substituted by from one to three $C_1$-$C_6$-alkyl groups or a $C_5$-$C_8$-cycloalkyl radical) and fused aromatics which may be alkyl-substituted and/or part-hydrogenated (especially naphthalene which is substituted by from one to four $C_1$-$C_6$-alkyl groups), and also mixtures of these solvents.

Specific examples of particularly preferred solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

In general, from 10 to 1000 ml, preferably from 10 to 500 ml of solvent are used per g of rylene reactant IIa or IIb.

Suitable bases are alkali metal and alkaline earth metal bases, preference being given to the alkali metal bases and particular preference to the sodium and potassium bases. Suitable bases are both inorganic bases, in particular the hydroxides such as sodium hydroxide and potassium hydroxide, and the salts of weak inorganic acids, in particular the carbonates and hydrogencarbonates, and organic bases, in particular the alkoxides such as sodium methoxide, sodium tert-butoxide, potassium methoxide, potassium isopropoxide and potassium tert-butoxide, and the salts of weak organic acids, in particular the acetates, the bases typically being used in anhydrous form.

In the case of reaction in the presence of a transition metal catalyst, preference is given to strong bases, especially the alkoxides such as sodium tert-butoxide and potassium tert-butoxide, while, in the absence of the catalyst, weak non-nucleophilic bases, in particular the salts of weak acids, preferably the carbonates such as sodium carbonate, are particularly suitable.

In general, from 0.1 to 10 mol, preferably from 0.5 to 3 mol of base are used per mole of rylene reactant Ia or IIb.

Suitable transition metal catalysts are in particular palladium complexes which can be used in combination with free ligand molecules, such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, preference being given to [1,1'-bis(diphenylphosphino)ferrocene]palladium(II) chloride, tetrakis(triphenylphosphine)palladium(0) and tris(dibenzylideneacetone)dipalladium(0).

Typically, the transition metal catalyst is used in an amount of from 1 to 20 mol %, in particular from 2 to 10 mol %, based on IIa or IIb.

In general, the simultaneous presence of free ligand molecules is advisable, for example of tri(tert-butyl)phosphine, triphenylphosphine and tris(o-tolyl)phosphine and 1,1'-(2,2'-diphenylphosphino)binaphthalene (BINAP). Typical amounts are from 80 to 500 mol %, preferably from 100 to 300 mol %, based on the transition metal catalyst.

The molar ratio of amine reactant Ma to rylene reactant IIa or IIb is, in the presence of a transition metal catalyst, generally from 5:1 to 1:1, in particular from 3:1 to 2:1, and, in its absence, generally from 200:1 to 1:1, in particular from 50:1 to 20:1. When the amine reactant serves simultaneously as the reaction medium, this quantitative restriction does not apply.

The reaction temperature is, in the presence of the catalyst, typically from 25 to 100° C., preferably from 70 to 90° C., and, in its absence, from 25 to 200° C., preferably from 70 to 170° C.

Especially in the case of use of the transition catalyst, it is recommended to undertake the reaction under protective gas.

The reaction times are, in the presence of the catalyst, typically from 1 to 48 h, in particular from 10 to 20 h, and, in the absence of the catalyst, generally from 0.5 to 24 h, in particular from 1 to 3 h.

A.1.2. Preparation of Rylene Derivatives of the Formula Ia12 (L=—Ar— or —Ar-E-Ar—)

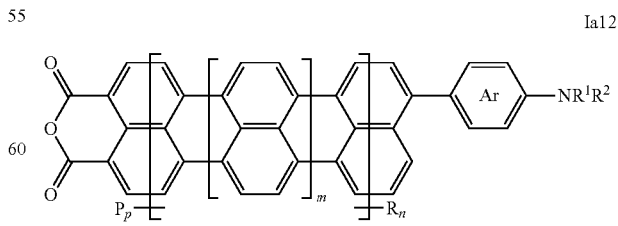

Ia12

In the structure, the phenylene ring Ar represents the placeholder for the (het)arylene radicals —Ar— and —Ar-E-Ar—.

To prepare the rylene derivatives Ia12, it is possible to react a) the peri-halorylenedicarboxylic anhydride IIa or b) the peri-halorylenedicarboximide IIb, in the presence of an organic solvent, if desired in a mixture with water, and also of a transition metal catalyst and of a base, to a Suzuki coupling reaction with a dioxaborolanyl-substituted amine of the formula IIIb

IIIb in which the $R^1 1$ radicals are the same or different and are each independently hydrogen, $C_1$-$C_{30}$-alkyl, $C_5$-$C_8$-cycloalkyl or (het)aryl, where the $R^1 1$ radicals present on one boron atom in each case may also be joined together with formation of a five- or six-membered ring which comprises the two oxygen atoms and the boron atom and may be substituted on the carbon atoms by up to 4 $C_1$-$C_{30}$-alkyl, $C_5$-$C_8$-cycloalkyl or (het)aryl groups, which should be followed by the above-described hydrolysis in case b).

The dioxaborolanyl-substituted amines IIIb used here as the amine reactant are obtainable by reacting the corresponding brominated amines IIIc

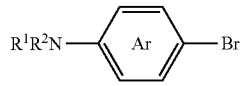

IIIc with diboranes of the formula IV

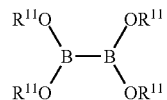

IV in the presence of an aprotic organic solvent, of a transition metal catalyst and of a base.

However, it is also possible to convert the peri-halorylenedicarboximide IIb by analogous reaction with the diborane IV to the peri-dioxaborolanyl derivative IIb″

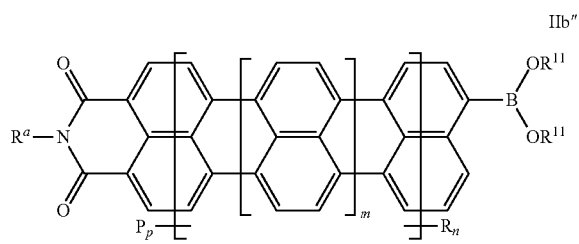

IIb″ and then to subject the latter to the Suzuki coupling with the brominated amine IIIc.

For the preparation of the dioxaboranyl derivatives IIIb or IIb′, suitable diboranes IV are especially bis(1,2- and 1,3-diolato)diboranes, tetraalkoxydiboranes, tetracycloalkoxydiboranes and tetra(het)aryloxydiboranes and their mixed forms. Examples of these compounds include: bis(pinacolato)diborane, bis(1,2-benzenediolato)diborane, bis(2,2-dimethyl-1,3-propanediolato)diborane, bis(1,1,3,3-tetramethyl-1,3-propanediolato)diborane, bis(4,5-pinanediolato)diborane, bis(tetramethoxy)diborane, bis(tetracyclopentoxy)diborane, bis(tetraphenoxy)diborane and bis(4-pyridiyloxy)diborane.

Preference is given to diboranes IV in which the two $R^1 1$ radicals present on one boron atom are joined together with formation of a five-membered or six-membered ring comprising the two oxygen atoms and the boron atom. Aromatic or saturated, even bicyclic, rings having from 5 to 7 carbon atoms as ring members may be fused to the five- or six-membered rings formed. All rings and ring systems may be substituted by up to 4 $C_1$-$C_{30}$-alkyl, $C_5$-$C_8$-cycloalkyl, aryl and/or hetaryl radicals; they are preferably substituted by up to 4 $C_1$-$C_4$-alkyl radicals. Examples of these preferred diboranes are the bis(1,2- and 1,3-diolato)diboranes already mentioned above, particular preference being given to bis(pinacolato)diborane.

The molar ratio of diborane IV to the reactant IIIc or IIb is generally from 0.8:1 to 3:1, in particular from 1.5:1 to 2:1.

Suitable solvents are in principle all aprotic solvents which are stable toward bases under the reaction conditions and have a boiling point above the selected reaction temperature, in which the reactants dissolve fully at reaction temperature and the catalysts and bases used at least partly, so that substantially homogeneous reaction conditions are present. It is possible to use either nonpolar aprotic or polar aprotic solvents, preference being given to the nonpolar aprotic solvents, especially toluene.

Examples of further particularly suitable nonpolar and polar aprotic solvents are the solvents listed in section A.1.1.

The amount of solvent is generally from 10 to 1000 ml, preferably from 20 to 300 ml per g of IIIc or IIb.

Suitable transition metal catalysts are in particular the palladium complexes mentioned in section A.1.1, which are in turn generally used in amounts of from 1 to 20 mol %, in particular from 2 to 10 mol %, based on IIIc or IIb. The additional presence of free ligand molecules is typically not required.

The bases used are preferably the alkali metal salts, especially the sodium and in particular the potassium salts, of weak organic and inorganic acids, such as sodium acetate, potassium acetate, sodium carbonate, sodium hydrogencarbonate, potassium carbonate and potassium hydrogencarbonate. Preferred bases are the acetates, in particular potassium acetate.

In general, from 1 to 5 mol, preferably from 2 to 4 mol of base are used per mole of IIIc or IIb.

The reaction temperature is typically from 20 to 180° C., in particular from 60 to 120° C.

The reaction time is generally from 0.5 to 30 h, in particular from 1 to 20 h.

In process technology terms, the procedure in the preparation of the dioxaboranyl derivatives is appropriately as follows:

Reactant IIIc or IIb and solvent are initially charged, diborane IV, the transition metal catalyst and the base are added in succession and the mixture is heated to the desired reaction temperature under protective gas for from 0.5 to 30 h. After cooling to room temperature, the solid constituents are filtered out of the reaction mixture and the solvent is distilled off under reduced pressure.

The Suzuki coupling between the peri-halorylenedicarboxylic acid derivative IIa or IIb and the dioxaborolanyl-substituted amine IIIb, or between the dioxaborolanyl rylene derivative IIb' and the p-bromophenylamine IIIc, is carried out in the presence of an organic solvent, if appropriate in a mixture with water, and of a transition metal catalyst and of a base.

The molar ratio of IIb to IIa or IIb is generally from 0.8:1 to 3:1, preferably from 0.9:1 to 2:1. The molar ratio of IIb' to IIIc is generally from 0.8:1 to 3:1, preferably from 1.5:1 to 2.5:1.

Suitable solvents for the Suzuki coupling are all solvents in which the reactants dissolve fully at reaction temperature and the catalysts and bases used at least partially, so that substantially homogeneous reaction conditions are present. Especially suitable are the solvents mentioned above for the preparation of the dioxaborolanyl derivatives, preference being given here too to the alkyl-substituted benzenes. The amount of solvent is typically from 10 to 1000 ml, preferably from 20 to 100 ml per g of rylene derivative.

Preference is given to using water as an additional solvent. In this case, generally from 10 to 1000 ml, in particular from 250 to 500 ml of water are used per l of organic solvent.

The transition metal catalysts used are in turn preferably palladium complexes, in which case the same preferences apply. The amount of catalyst used is typically from 1 to 20 mol %, in particular from 1.5 to 5 mol %, based on the rylene derivative.

Preferred bases are in turn the alkali metal salts of weak acids, particular preference being given to the carbonates such as sodium carbonate and in particular potassium carbonate. In general, the amount of base is from 0.1 to 10 mol, in particular from 0.2 to 5 mol per mole of rylene derivative.

The reaction temperature is generally from 20 to 180° C., preferably from 60 to 120° C. When water is used in step b), it is recommended not to undertake the reaction at temperatures above 100° C., since it would otherwise be necessary to work under pressure.

The reaction has typically ended within from 0.5 to 48 h, in particular within from 5 to 20 h.

In process technology terms, the procedure in the Suzuki coupling is appropriately as follows:

The reactants and solvents are initially charged, transition metal catalysts and the base, preferably dissolved in water or a water/alcohol mixture, are added and the mixture is heated to the desired reaction temperature under protective gas for from 0.5 to 48 h. After cooling to room temperature, the organic phase is removed from the reaction mixture and the solvent is distilled off under reduced pressure.

A.1.3. Preparation of Rylene Derivatives of the Formula Ia13 (L=(het)arylene radical —Ar— or —Ar-E-Ar— joined via ethenylene)

and, if desired, of a cocatalyst, in a Heck reaction with a vinylamine of the formula IIId

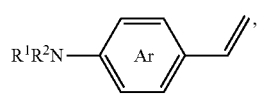

IIId which should be followed by the above-described hydrolysis in case b).

Suitable solvents for this reaction are especially polar, but also nonpolar aprotic organic solvents. In addition to the solvents listed in section A.1.1, for example, halogenated hydrocarbons and aliphatic amines are also suitable as solvents. Specific examples of particularly suitable solvents include: diethylamine, piperidine, tetrahydrofuran, dimethylformamide, N-methylpyrrolidone, methylene chloride, dimethyl sulfoxide and toluene.

Suitable transition metal catalysts are the palladium compounds likewise listed in section A.1.1, which may also be prepared in situ from palladium salts such as palladium(II) acetate and ligand molecules. Generally, the simultaneous presence of free ligand molecules is also advisable in the case of direct use of palladium complexes. Examples of particularly preferred transition catalyst systems are tetrakis(triphenylphosphine)palladium(0), tris(dibenzylideneacetone)dipalladium(0) and palladium(II) acetate, and also triphenylphosphine and tris(o-tolyl)phosphine.

The cocatalysts used may be alkali metal halides and quaternary ammonium salts. Examples include lithium chloride, tetrabutylammonium chloride, tetrabutylammonium bromide and tetrabutylammonium hydrogensulfate.

Suitable bases in addition to the alkali metal salts, especially the sodium and potassium salts, of weak inorganic and organic acids, are also tertiary amines. Examples of particularly suitable bases are sodium hydrogencarbonate, sodium carbonate, potassium carbonate, sodium acetate, potassium acetate and tri($C_2$-$C_4$-alkyl)amines such as triethylamine.

The reaction temperatures are typically from 0 to 150° C., preferably from 25 to 80° C.

It is recommended to work under protective gas.

The reaction is generally complete within from 1 to 24 h.

Further details of this reaction can be taken from Chem. Rev. 100, p. 3009-3066 (2000).

A.1.4. Preparation of Rylene Derivatives of the Formula Ia14 (L=(Het)Arylene Radical —Ar— or —Ar-E-Ar— Joined Via Ethynylene)

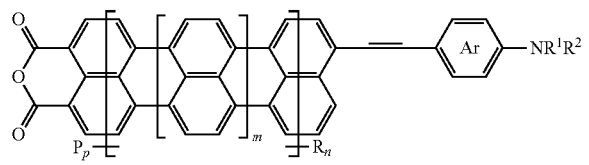

Ia13

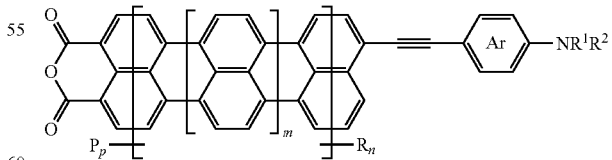

Ia14

In the structure, the phenylene ring Ar again represents the placeholder for the (het)arylene radicals —Ar— and —Ar-E-Ar—.

To prepare the rylene derivatives Ia13, it is possible to react a) the peri-halorylenedicarboxylic anhydride IIa or b) the peri-halorylenedicarboximide IIb, in the presence of an aprotic organic solvent, of a transition metal catalyst, of a base In the structure, the phenylene ring Ar again represents the placeholder for the (het)arylene radicals —Ar— and —Ar-E-Ar—.

To prepare the rylene derivatives Ia14, it is possible to react a) the peri-halorylenedicarboxylic anhydride IIa or b) the peri-halorylenedicarboximide IIb, in the presence of an aprotic organic solvent, of a transition metal catalyst, of a base and, if desired, of a copper cocatalyst, with an ethynylamine of the formula IIIe

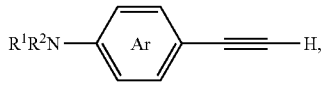

IIIe which should be followed by the above-described hydrolysis in case b).

Suitable solvents for this reaction are especially polar, but also nonpolar organic solvents. In addition to the solvents listed in section A.1.1, for example, halogenated hydrocarbons and amines are also suitable as solvents. Specific examples of particularly suitable solvents include: diethylamine, piperidine, tetrahydrofuran, dimethylformamide, methylene chloride and toluene.

Suitable transition metal catalysts are the palladium complexes likewise listed in section A.1.1, preference being given to tetrakis(triphenylphosphine)palladium(0) and bis(triphenylphosphine)palladium(II) chloride.

The cocatalysts used may be copper(I) and copper(II) compounds. In addition to the oxides, suitable cocatalysts are copper salts of organic and especially inorganic acids, in particular copper(I) iodide.

Suitable bases are, in addition to the alkali metal salts, especially the cesium salts, of weak inorganic and organic acids, also secondary and tertiary amines. Examples of particularly suitable bases are cesium carbonate, di($C_2$-$C_4$-alkyl) amines such as diethylamine and diisopropylamine, tri($C_2$-$C_4$-alkyl)amines such as triethylamine, and cyclic amines such as piperidine.

The reaction temperatures are typically from 0 to 150° C., preferably from 25 to 80° C.

It is advisable to work under protective gas.

The reaction has generally ended within from 1 to 24 h.

Further details of this reaction can be taken from Chem. Rev. 103, p. 1979-2017 (2003).

A.2 Preparation of Rylene Derivatives of the Formula Ia2

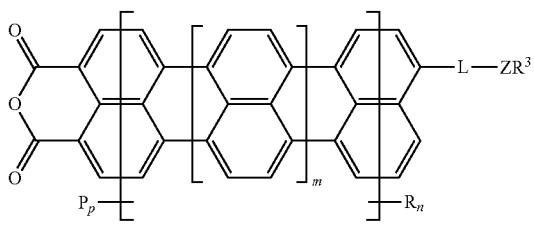

Ia2

The preparation of the rylene derivatives Ia2 will be described below in sections as a function of the particular bridging member L.

A.2.1. Preparation of Rylene Derivatives of the Formula Ia21 (L=Chemical Bond)

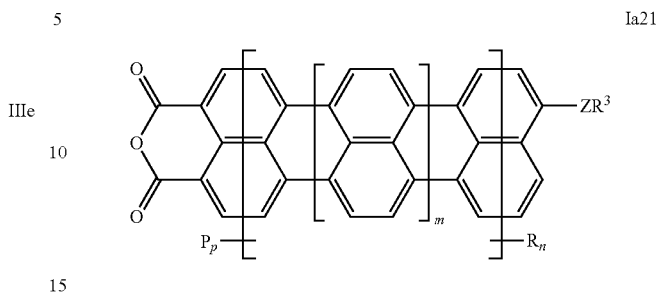

Ia21

To prepare the rylene derivatives Ia21, it is possible to react a) the peri-halorylenedicarboxylic anhydride IIa or b) the peri-halorylenedicarboximide IIb, in the presence of a non-nucleophilic solvent and of a base, with a (thio)alcohol of the formula Va

$H-ZR^3$   Va, which should be followed by the above-described hydrolysis in case b).

Suitable non-nucleophilic solvents for this reaction are in particular polar aprotic solvents, especially aliphatic carboxamides (preferably N,N-di-$C_1$-$C_4$-alkyl-$C_1$-$C_4$-carboxamides) and lactams, such as dimethylformamide, diethylformamide, dimethylacetamide, dimethylbutyramide and N-methylpyrrolidone.

The non-nucleophilic solvents used may also be nonpolar aprotic solvents, but these solvents are not preferred. Examples include aromatic hydrocarbons such as benzene, toluene and xylene.

The amount of solvent depends on the solubility of the halogenated rylene derivative. In general, from 2 to 200 ml, in particular from 3 to 150 ml of solvent per g of rylene reactant IIa or IIb are required.

Suitable bases are in particular inorganic and organic alkali metal or alkaline earth metal bases, the alkali metal bases being particularly suitable. Examples of inorganic bases are alkali metal and alkaline earth metal carbonates and hydrogencarbonates, hydroxides, hydrides and amides; examples of organic bases are alkali metal and alkaline earth metal alkoxides (especially the $C_1$-$C_{10}$-alkoxides, in particular tert-$C_4$-$C_6$-alkoxides), (phenyl)alkylamides (especially the bis ($C_1$-$C_4$-alkyl)amides) and triphenylmethyl metallates. Preferred bases are the carbonates and hydrogen-carbonates, particular preference being given to the carbonates. Preferred alkali metals are lithium, sodium, potassium and cesium; particularly suitable alkaline earth metals are magnesium and calcium.

Specific examples of the metal bases include: lithium carbonate, sodium carbonate, potassium carbonate and cesium carbonate; sodium hydrogencarbonate and potassium hydrogencarbonate; lithium hydroxide, sodium hydroxide, potassium hydroxide and cesium hydroxide; lithium hydride, sodium hydride and potassium hydride; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide, potassium tert-butoxide, lithium (1,1-dimethyl)octoxide, sodium (1,1-dimethyl)octoxide and potassium (1,1-dimethyl)octoxide; lithium dimethylamide, lithium diethylamide, lithium diisopropylamide, sodium diisopropylamide, lithium hexamethyldisilazide, sodium hexamethyldisilazide, potassium hexamethyldisilazide, triphenylmethyllithium, triphenylmethylsodium and triphenylmethylpotassium.

In addition to these metal bases, purely organic nitrogen bases are also suitable.

Suitable examples of these are alkylamines, especially tri($C_2$-$C_6$-alkyl)amines such as triethylamine, tripropylamine and tributylamine, alcoholamines, especially mono-, di- and tri($C_2$-$C_4$-alcohol)amines such as mono-, di- and triethanolamine, and heterocyclic bases such as pyridine, 4-(N,N-dimethylamino)pyridine, (4-pyrrolidino)pyridine, N-methylpiperidine, N-methylpiperidone, N-methylmorpholine, N-methyl-2-pyrrolidone, pyrimidine, quinoline, isoquinoline, quinaldine, diazabicyclooctane (DABCO), diazabicyclononene (DBN) and diazabicycloundecene (DBU).

Very particularly preferred bases are lithium carbonate, sodium carbonate, potassium carbonate and cesium carbonate.

In general at least 0.4 equivalent of base is required per mole of (thio)alcohol Va. Particularly suitable use amounts for the metal bases are from 0.4 to 3 equivalents, in particular from 0.4 to 1.2 equivalents per mole of Va. In the case of the purely organic bases, the use amount is preferably from 0.4 to 10 equivalents, more preferably from 0.4 to 3 equivalents per mole of Va. When the organic base is used simultaneously as the solvent, which may be the case especially for the heterocyclic bases, a quantitative restriction is of course superfluous.

The reaction may be undertaken in the presence of phase transfer catalysts.

Suitable phase transfer catalysts are in particular quaternary ammonium salts and phosphonium salts, such as tetra($C_1$-$C_{18}$-alkyl)ammonium halides and tetrafluoroborates, benzyl tri($C_1$-$C_{18}$-alkyl)ammonium halides and tetrafluoroborates, and tetra($C_1$-$C_{18}$-alkyl)- and tetraphenylphosphonium halides, and crown ethers. The halides are generally the fluorides, chlorides, bromides and iodides, preference being given to the chlorides and bromides. Specific particularly suitable examples are: tetraethylammonium chloride, tetrabutylammonium bromide, tetrabutylammonium iodide, tetrabutylammonium tetrafluoroborate and benzyltriethylammonium chloride; tetrabutylphosphonium bromide and tetraphenylphosphonium chloride and bromide; 18-crown-6, 12-crown-4 and 15-crown-5.

When a phase transfer catalyst is used, its use amount is typically from 0.4 to 10 equivalents, in particular from 0.4 to 3 equivalents per mole of (thio)alcohol Va. In general, from 1 to 10 mol, preferably from 1 to 5 mol of (thio)alcohol Va are used per mole of rylene reactant IIa or IIb.

The reaction temperature depends upon the reactivity of the substrate and is generally in the range from 30 to 150° C.

The reaction time is typically from 0.5 to 96 h, in particular from 2 to 72 h.

A.2.2. Preparation of Rylene Derivatives of the Formula Ia22 (L=—Ar— or —Ar-E-Ar—)

The phenylene ring Ar represents the placeholder for the (het)arylene radicals —Ar— and —Ar-E-Ar—.

The preparation of the rylene derivatives Ia22 can be undertaken analogously to the preparation of the rylene derivatives Ia12 described in section A.1.2.

Accordingly, a) the peri-halorylenedicarboxylic anhydride IIa or b) the peri-halorylenedicarboximide IIb can be reacted, in the presence of an organic solvent, if desired in a mixture with water, and also of a transition metal catalyst and of a base to a Suzuki coupling reaction with a dioxaborolanyl-substituted (thio)alcohol of the formula Vb

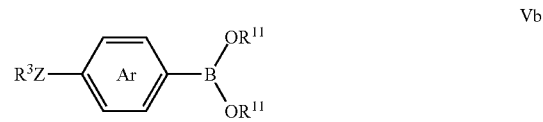

Vb in which the $R^{11}$ radicals are the same or different and are each independently hydrogen, $C_1$-$C_{30}$-alkyl, $C_5$-$C_8$-cycloalkyl or (het)aryl, where the $R^{11}$ radicals present on one boron atom in each case may also be joined together with formation of a five- or six-membered ring which comprises the two oxygen atoms and the boron atom and which may be substituted on the carbon atoms by up to 4 $C_1$-$C_{30}$-alkyl, $C_5$-$C_8$-cycloalkyl or (het)aryl groups, which should be followed in case b) by the above-described hydrolysis.

The dioxaborolanyl-substituted (thio)alcohols Vb used here as the amine reactant are obtainable analogously to the dioxaborolanyl-substituted amines IIIc by reacting the corresponding brominated (thio)alcohols Vc

Vc with diboranes of the formula IV

IV in the presence of an aprotic organic solvent, of a transition metal catalyst and of a base.

However, it is also possible here to convert the peri-halorylenedicarboximide IIb by analogous reaction with the diborane IV to the peri-dioxaborolanyl derivative IIb″

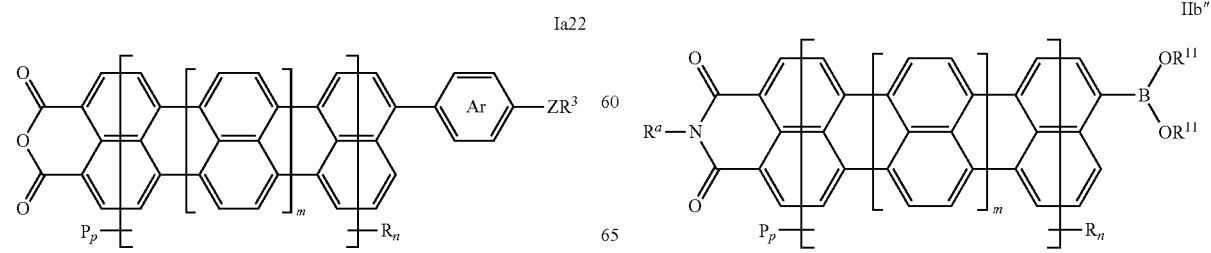

Ia22

IIb″ and then to subject the latter to the Suzuki coupling with the brominated (thio)alcohol Vc.

Further details of these reactions can be taken from the description of the analogous reactions in section A.1.2.

A.2.3. Preparation of Rylene Derivatives of the Formula Ia23 (L=(Het)Arylene Radical —Ar— or —Ar-E-Ar— Joined Via Ethenylene)

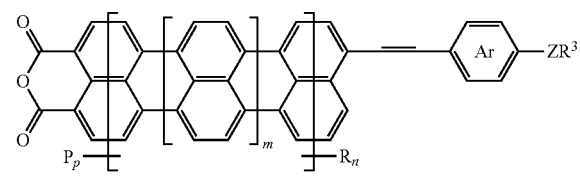

Ia23

The phenylene ring Ar here again represents the placeholder for the (het)arylene radicals —Ar— and —Ar-E-Ar—.

The preparation of the rylene derivatives Ia23 can be undertaken analogously to the preparation of the rylene derivatives Ia13 described in section A.1.3. Accordingly, a) the peri-halorylenedicarboxylic anhydride IIa or b) the peri-halorylenedicarboximide IIb, in the presence of an aprotic organic solvent, of a transition metal catalyst, of a base and, if desired, of a cocatalyst, can be reacted in a Heck reaction with a vinyl (thio)alcohol of the formula Vd

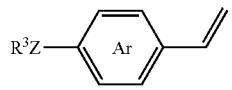

Vd which should be followed in case b) by the above-described hydrolysis.

Further details of this reaction can be taken from section A.1.3.

A.2.4. Preparation of Rylene Derivatives Ia24 (L=(Het)Arylene Radical —Ar— or —Ar-E-Ar— Joined Via Ethynylene)

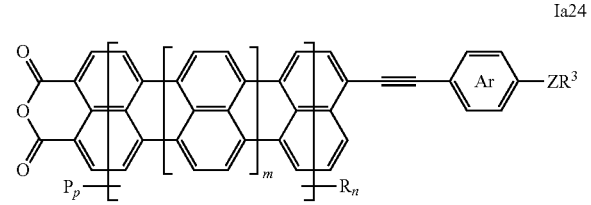

Ia24

The phenylene ring Ar here again represents the placeholder for the (het)arylene radicals —Ar— and —Ar-E-Ar—.

The preparation of the rylene derivatives Ia24 can again be undertaken analogously to the preparation of the rylene derivatives Ia14 described in section A.1.4.

Accordingly, a) the peri-halorylenedicarboxylic anhydride IIa or b) the peri-halorylene-dicarboximide IIb, in the presence of an aprotic organic solvent, of a transition metal catalyst, of a base and, if desired, of a copper cocatalyst, can be reacted with an ethynyl (thio)alcohol of the formula Ve

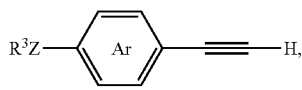

Ve which should be followed in case b) by the above-described hydrolysis.

Further details of this reaction can be taken from section A.1.4.

A.3. Preparation of Rylene Derivatives of the Formula Ia3

To prepare the rylenetetracarboxylic monoimide monoanhydrides Ia3

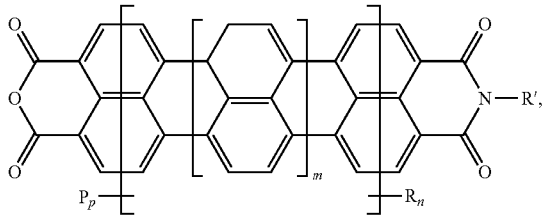

Ia3 a rylenetetracarboxylic dianhydride of the formula IIc

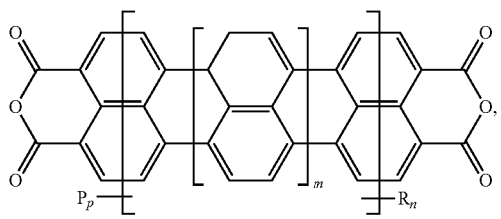

IIc in the presence of a polar aprotic solvent and of an imidation catalyst, can be reacted with a primary amine of the formula VI

    VI.

Suitable polar aprotic solvents are in particular aprotic nitrogen heterocycles such as pyridine, pyrimidine, imidazole, quinoline, isoquinoline, quinaldine, N-methylpiperidine, N-methylpiperidone and N-methylpyrrolidone, carboxamides such as dimethylformamide and dimethylacetamide, and tetraalkylureas such as tetramethylurea, particular preference being given to N-methylpyrrolidone.

In general, from 2 to 500 ml, preferably from 2 to 50 ml of solvent are used per g of IIc.

Suitable imidation catalysts are in particular Lewis-acidic salts of organic and inorganic acids with metals such as zinc, iron, copper and magnesium, and also the oxides of these metals, for example zinc acetate, zinc propionate, zinc oxide, iron(II) acetate, iron(II) chloride, iron(II) sulfate, copper(II) acetate, copper(II) oxide and magnesium acetate, particular preference being given to zinc acetate. The salts are preferably used in anhydrous form.

Typically, from 20 to 500 mol %, in particular from 80 to 120 mol % of catalyst, based on IIc, are used.

It is also possible to use the acids themselves, i.e., for example, organic acids, in particular $C_1$-$C_3$-carboxylic acids such as formic acid, acetic acid and propionic acid, and inorganic acids such as phosphoric acid, in each case preferably in highly concentrated form, as imidation catalysts. In this case, the acids serve simultaneously as a solvent or as a cosolvent and are therefore typically used in excess.

Typically, the molar ratio of primary amine VI to rylenetetracarboxylic dianhydride IIc is from about 0.1:1.5 to 0.5:1.2, in particular from 0.8:1.5 to 0.8:1.2. The reaction temperature is generally from 60 to 250° C., preferably from 100 to 230° C., more preferably from 90 to 170° C.

It is recommended to carry out the reaction under protective gas.

The reaction is typically complete within from 1 to 4 h.

B. Preparation of Rylene Derivatives Ib

In the preparation of the rylene derivatives Ib in which the two X radicals are joined to form an acid-containing imide radical (x2) or condensate radical (x3), it is advantageously possible to use the rylene derivatives Ia which have the Y radicals desired in each case as the reactant.

B.1. Preparation of Rylene Derivatives of the Formula Ib1

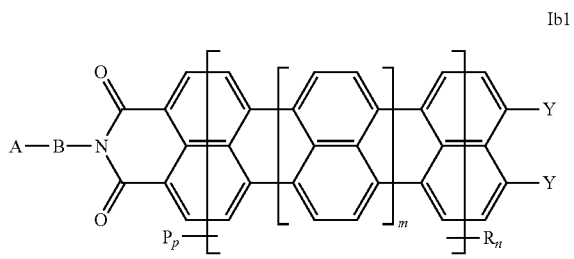

Ib1

The preparation of the rylene derivatives Ib1 is described below in sections depending on the substituents Y.

B.1.1. Preparation of Rylene Derivatives Ib11

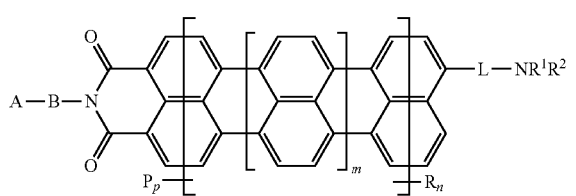

Ib11

The preparation of the rylene derivatives Ib11 can be effected by reacting the corresponding rylene derivatives Ia1

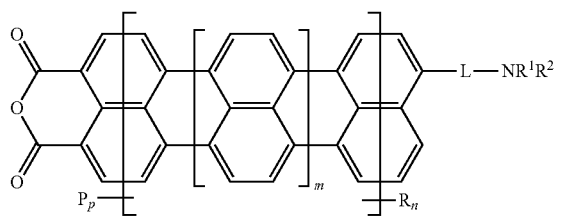

Ia1 with a primary amine of the formula VII

  VII in the presence of a polar aprotic solvent and of an imidation catalyst.

This imidation reaction can be undertaken analogously to the imidation reaction described in section A.3 to prepare the rylenetetracarboxylic monoimide monoanhydrides Ia3.

Alternatively, the imidation can also be carried out with larger amounts of primary amine VI (generally from 1 to 10 mol, preferably from 2 to 6 mol per mole of Ia1) in the presence of the polar aprotic solvent and of an alkali metal or alkaline earth metal base.

Preference is given here to the alkali metal bases, especially to the sodium and potassium bases. Suitable bases are both inorganic bases, in particular the hydroxides such as sodium hydroxide and potassium hydroxide, and organic bases, in particular the alkoxides such as sodium methoxide, potassium methoxide, potassium isopropoxide and potassium tert-butoxide, which are typically used in anhydrous form. Very particular preference is given to potassium hydroxide.

In general, from 1 to 10 mol, preferably from 2 to 4 mol of base are required per mole of Ia1.

The reaction temperature is generally from 50 to 200° C., preferably from 60 to 150° C. Typical reaction times are from 0.5 to 24 h, in particular from 2 to 10 h.

B.1.2. Preparation of Rylene Derivatives of the Formula Ib12

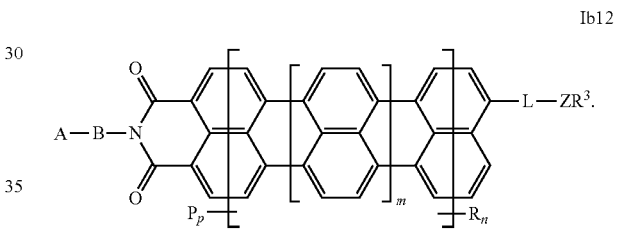

Ib12

The preparation of the rylene derivatives Ib12 can be effected analogously by reacting the corresponding rylene derivatives Ia2

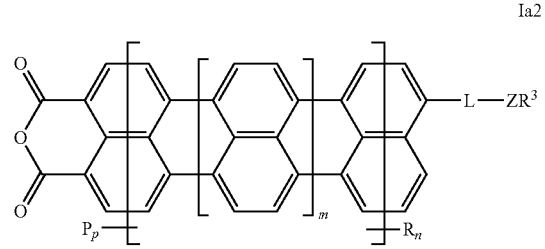

Ia2 with a primary amine of the formula VII

  VII in the presence of a polar aprotic solvent and of an imidation catalyst.

Further details of the performance of this imidation reaction can again be taken from section A.3.

Alternatively, the imidation may also, as described in section B.1.1, be undertaken with larger amounts of amine VII in the presence of the polar aprotic solvent and of an alkali metal/alkaline earth metal base.

B.1.3. Preparation of Rylene Derivatives of the Formula Ib13

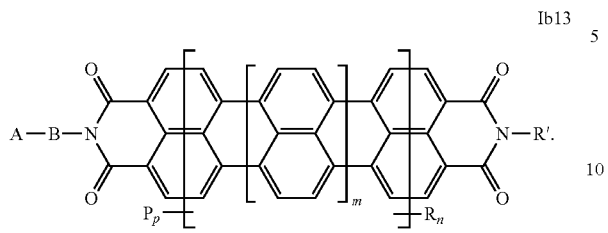

The rylene derivatives Ib13 too are obtainable analogously by reacting the corresponding rylene derivatives Ia3

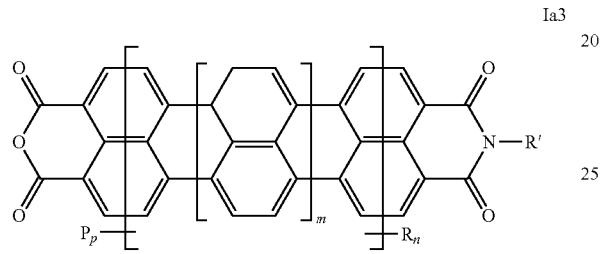

with a primary amine of the formula VII

     VII in the presence of a polar aprotic solvent and of an imidation catalyst.

Further details on the performance of this imidation reaction can again be taken from section A.3.

The imidation may also, as described in section B.1.1, be undertaken with larger amounts of amine VII in the presence of the polar aprotic solvent and of an alkali metal/alkaline earth metal base.

Alternatively, the terrylene and quaterrylene derivatives Ib13 (m=1 and 2 respectively) can also be prepared by a) reacting naphthalene- or perylenedicarboxylic anhydride VIII

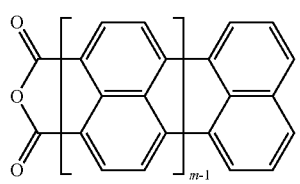

first in the presence of a polar aprotic solvent and of an imidation catalyst with a primary amine of the formula VII

     VII, b) then reacting the naphthalene- or perylenedicarboximide of the formula VIIIa

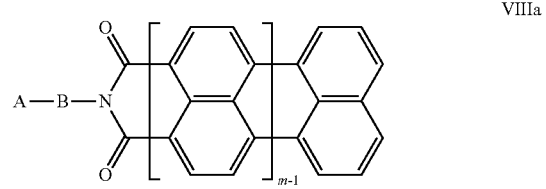

obtained in this reaction, in the presence of a base-stable high-boiling organic solvent and of an alkali metal or alkaline earth metal base and of a nitrogen-containing auxiliary base, with a perylenedicarboximide of the formula VIIIb

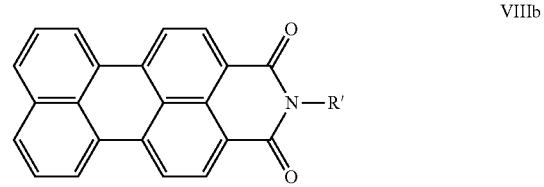

and c) if desired, reacting the resulting terrylene- or quaterrylenetetracarboxylic monoimide monoanhydride Ib13 (n=p=0) unsubstituted in the rylene skeleton,
c1) in the presence of an inert diluent, with elemental bromine and
c2) then reacting the brominated terrylene or quaterrylene derivative Ib13'

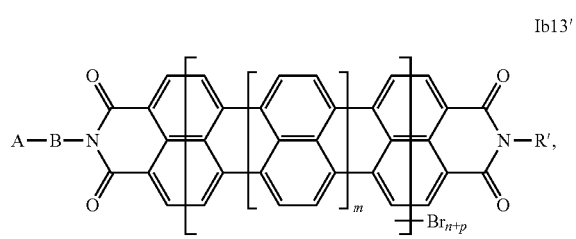

in the presence of a non-nucleophilic solvent and of a base, with a (thio)alcohol of the formula IX

     IX and/or an amine of the formula IIIa

     IIIa to give the substituted rylene derivative Ib13 (n and/or p≠0).

In the imidation step a), it is again possible to proceed analogously to the imidation described in section A.3.

In step b), reaction of the acid-functionalized naphthalene- or perylenedicarboximide VIIIa with the perylenedicarboximide VIIIb forms the terrylene or quaterrylene derivative Ib13 unsubstituted in the rylene skeleton.

Suitable solvents for step b) are in principle all high-boiling (boiling point>100° C. and above the reaction temperature) solvents which are stable toward bases under the reaction conditions and in which the reactants VIIIa and VIIIb dissolve fully at reaction temperature and the bases used at least partially, so that substantially homogeneous reaction conditions are present.

Particularly suitable solvents are aprotic solvents which may be nonpolar or polar, but are preferably polar.

Examples of these solvents are the solvents mentioned in section A.1.1, and the polar aprotic solvent used may additionally also be trialkylamines, especially tri($C_3$-$C_6$-alkyl) amines such as tripropyl- and tributylamine.

Particularly preferred solvents are diphenyl ethers and in particular dialkyl ethers of diethylene glycol, in particular diethylene glycol dimethyl and diethyl ether.

In addition, it is also possible to use protic solvents, in particular those which have amino and hydroxyl functions, for example alcoholamines, in particular mono-, di- and tri-$C_2$-$C_4$-alcoholamines such as mono-, di- and triethanolamine.

In general, from 10 to 50 ml of polar aprotic solvent, from 50 to 250 ml of nonpolar aprotic solvent or from 3 to 50 ml of protic solvent are used per g of perylene-based reactant.

Suitable bases are strong inorganic or organic alkali metal or alkaline earth metal bases, the alkali metal bases being particularly suitable.

Examples of these bases are those mentioned in section A.2.1. Particular preference is given to lithium propylamide, sodium hydroxide, potassium hydroxide, sodium methoxide, sodium tert-butoxide, potassium methoxide and potassium tert-butoxide, very particular preference being given to the tert-butoxides.

To facilitate the reaction, it is advisable to add a nitrogen-containing auxiliary base with low nucleophilic action. Suitable bases are alkylamines liquid at the reaction temperatures, in particular tri-$C_3$-$C_6$-alkylamines such as tripropylamine and tributylamine, alcoholamines, especially mono-, di- and tri-$C_2$-$C_4$-alcoholamines such as mono-, di- and triethanolamine, and in particular heterocyclic bases such as pyridine, N-methylpiperidine, N-methylpiperidone, N-methylmorpholine, N-methyl-2-pyrolidone, pyrimidine, quinoline, isoquinoline, quinaldine and In particular diazabicyclononene (DBN) and diazabicycloundecene (DBU).

For the metal base, suitable use amounts are from 2 to 20 mol, preferably from 8 to mol, per mole of perylene reactant, and, for the auxiliary base, from 1 to 60 g, preferably from 5 to 30 g, per g of perylene reactant.

The metal base may be used in solid or in dissolved form. When the metal base is used in combination with a nonpolar aprotic reaction solvent in which it is not sufficiently soluble, it can be dissolved in an alcohol which has a higher base strength than the alkali metal base. Suitable alcohols are in particular tertiary aliphatic alcohols which may comprise aryl substituents and have a total of from four to twelve carbon atoms, for example tert-butanol, 2-methyl-2-butanol (tert-amyl alcohol), 3-methyl-3-pentanol, 3-ethyl-3-pentanol, 2-phenyl-2-pentanol, 2,3-dimethyl-3-pentanol, 2,4,4-trimethyl-2-pentanol and 2,2,3,4,4-pentamethyl-3-pentanol.

The reaction temperature is typically from 50 to 210° C., preferably from 70 to 180° C.

The reaction is generally complete within from 2 to 12 h.

It is also possible to use a peri-halo derivative, especially a peri-chloro derivative and in particular a peri-bromo derivative of one of the two reactants VIIIa or VIIIb and thus to ease the reaction.

In this case, it is possible, for example, in the preparation of the terrylene derivatives Ib3, to use a molar ratio of halogenated naphthalene reactant VIIIa to perylene reactant VIIIb of from 4:1 to 1:1, in particular from 2:1 to 1:1, while the molar ratio in the case of the unhalogenated naphthalene reactant VIIIa is generally from 8:1 to 1:1, in particular from 6:1 to 2:1.

When a halogenated reactant is used, particularly suitable reaction media are not only the polar aprotic solvents based on ethers but also nonpolar aprotic solvents, preferably xylenes, mesitylene and in particular toluene and decalin.

The amount of base can likewise be reduced and the presence of the nitrogen-containing auxiliary base is advisable in particular only in the case of use of the alkoxides and of the hydroxides. Thus, the use amount for the metal base is generally from 5 to 20 mol, in particular from 5 to 10 mol, per mole of perylene reactant, and, for the auxiliary base, generally from 1 to 15 g, in particular from 1 to 5 g, per g of perylene reactant.

The reaction times too are lowered in the case of use of a halogenated reactant, typically to from 1 to 3 h.

The bromination in the optional step c2) can be undertaken in a commonly known manner.

Suitable inert diluents are not only halogenated aromatics such as chlorobenzene and di- and trichlorobenzenes, but also especially aliphatic halohydrocarbons, in particular methanes and ethanes such as tribromo-, tetrachloro- and tetrabromomethane, 1,2-dichloro-, 1,1-dibromo- and 1,2-dibromoethane, 1,1,1-trichloro-, 1,1,2-trichloro-, 1,1,1-tribromo- and 1,1,2-tribromoethane, and 1,1,1,2-tetrachloro-, 1,1,2,2-tetrachloro-, 1,1,1,2-tetrabromo- and 1,1,2,2-tetrabromoethane, preference being given to dichloromethane (methylene chloride) and trichloromethane (chloroform).

In general, from 30 to 200 g, preferably from 100 to 150 g, of solvent are used per g of rylene reactant.

The molar ratio of bromine to rylene reactant is generally from 10:1 to 100:1, in particular from 40:1 to 60:1.

The reaction temperature is typically from 40 to 140° C., in particular from 40 to 90° C.

When the reaction temperature is above the boiling point of the solvent used, it is advisable to undertake the bromination under pressure.

The subsequent nucleophilic substitution of the bromine atoms by (het)aryloxy or -thio radicals —ZR or amino radicals —NR'$R^2$ in the optional step c2) can finally be effected analogously to the preparation, described in section A.2.1, of the rylene derivatives Ia21.

B.1.4. Preparation of Rylene Derivatives of the Formula Ib14

The reactants used for the preparation of the rylene derivatives Ib14

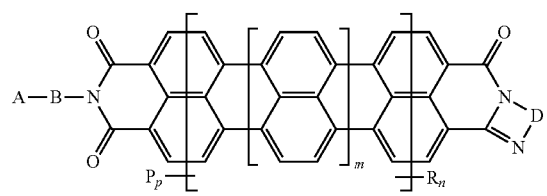

Ib14 may be the corresponding rylene derivatives I'

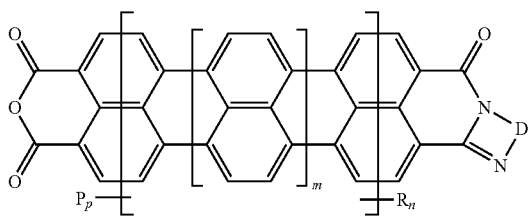

I' which can be reacted in turn, in the presence of a polar aprotic solvent and of an imidation catalyst, with a primary amine of the formula VII

A-B—NH$_2$     VII.

Further details on the performance of this imidation reaction here too can be taken from section A.3.

Alternatively, the imidation here too, as described in section B.1.1, can be performed with larger amounts of amine VII in the presence of the polar aprotic solvent and of an alkali metal/alkaline earth metal base.

The preparation of the semicondensate I' serving as the reactant can be performed in a customary manner by reacting the rylenetetracarboxylic dianhydride IIc

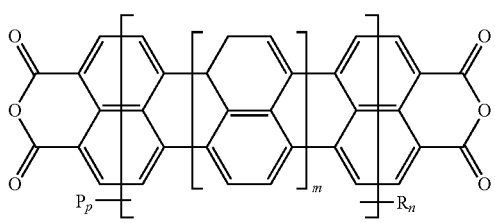

IIc with an aromatic diamine of the formula X

H$_2$N-D—NH$_2$     X in the presence of a nitrogen-basic compound or of phenol as the solvent, and of a Lewis acid or of piperidine as a catalyst.

The molar ratio of aromatic diamine X to rylenetetracarboxylic dianhydride IIc is typically from 1.5:1 to 1:1, in particular from 1.2:1 to 1.05:1.

Suitable nitrogen-basic compounds are in particular nitrogen heterocycles which preferably do not have further functionalization, such as quinoline, isoquinoline, quinaldine, pyrimidine, N-methylpiperidine, pyridine, pyrrole, pyrazole, triazole, tetrazole, imidazole and methylimidazole. Preference is given to tertiary nitrogen-basic compounds, in particular quinoline.

In general, from 5 to 200 ml, preferably from 10 to 50 ml, of solvent are used per g of rylene reactant IIc.

Suitable catalysts are Lewis acids, for example zinc compounds, in particular zinc salts such as zinc acetate and zinc chloride, and zinc oxide, inorganic and organic acids such as hydrochloric acid, acetic acid and p-toluenesulfonic acid, preference being given to zinc acetate.

Likewise suitable as a catalyst is piperazine which is preferably used in combination with phenol as the solvent.

Typically, from 0.25 to 5.0 mol, in particular from 1.0 to 2.0 mol, of catalyst are used per mole of IIc.

The reaction temperature is generally from 100 to 240° C., preferably from 160 to 240° C.

It is advisable to work under protective gas, for example nitrogen or argon.

In general, the condensation is complete within from 0.5 to 24 h, in particular from 2 to 6 h.

B.2. Preparation of Rylene Derivatives of the Formula Ib2

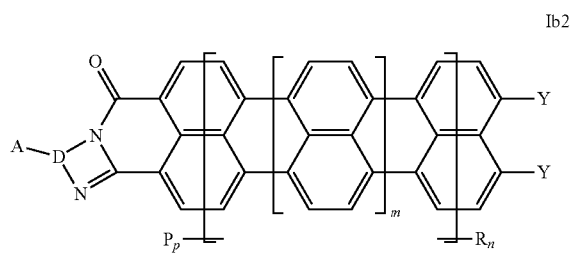

The preparation of the rylene derivatives Ib2 is described in sections below, likewise depending on the substituents Y.

B.2.1. Preparation of Rylene Derivatives Ib21

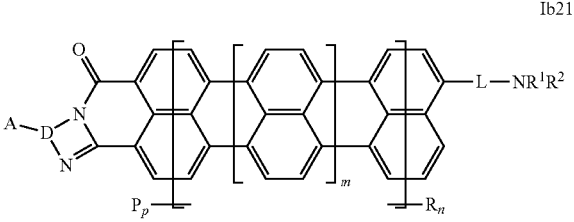

The preparation of the rylene derivatives Ib21 can be effected by reacting the corresponding rylene derivatives Ia1

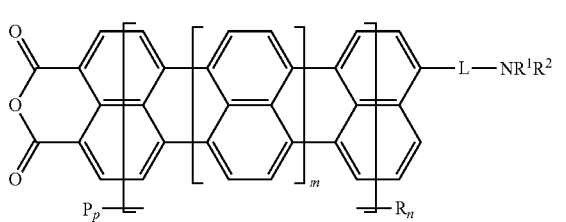

with an aromatic diamine of the formula XI

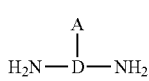

in the presence of a nitrogen-basic compound or of phenol as a solvent, and of a Lewis acid or of piperidine as a catalyst.

This condensation reaction can be undertaken analogously to the condensation reaction described in section B.1.4 for preparing the rylene reactants 1'.

B.2.2. Preparation of Rylene Derivatives of the Formula Ib22

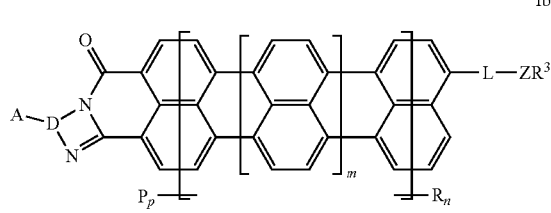

Ib22

The preparation of the rylene derivatives Ib22 can be effected analogously by reacting the corresponding rylene derivatives Ia2

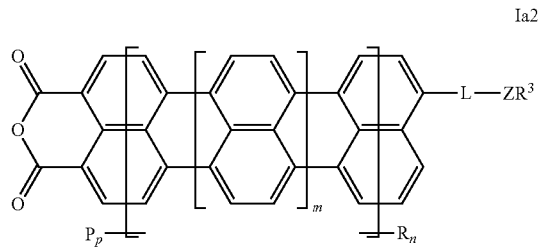

Ia2 with an aromatic diamine of the formula XI

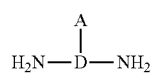

XI in the presence of a nitrogen-basic compound or of phenol as a solvent, and of a Lewis acid or of piperidine as a catalyst.

Further details on the performance of this condensation reaction can again be taken from section B.1.4.

B.2.3. Preparation of Rylene Derivatives of the Formula Ib23

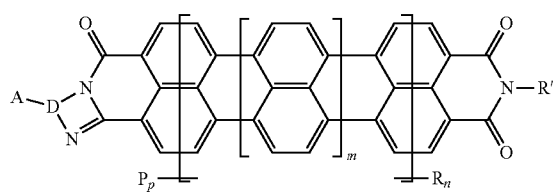

Ib23

The rylene derivatives Ib23 too are obtainable analogously by reacting the corresponding rylene derivatives Ia3

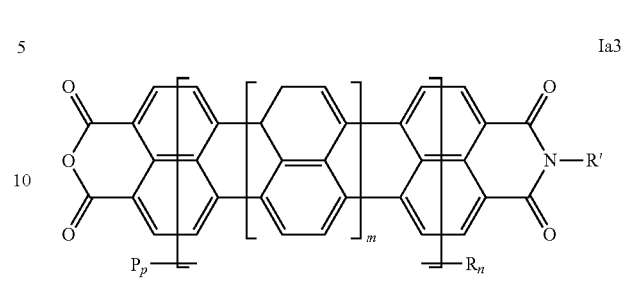

Ia3 with an aromatic diamine of the formula XI

XI in the presence of a nitrogen-basic compound or of phenol as a solvent, and of a Lewis acid or of piperidine as a catalyst.

Further details on the performance of this condensation reaction here too can be taken from section B.1.4.

B.2.4. Preparation of Rylene Derivatives of the Formula Ib24

The reactants used for the preparation of the rylene derivatives Ib24

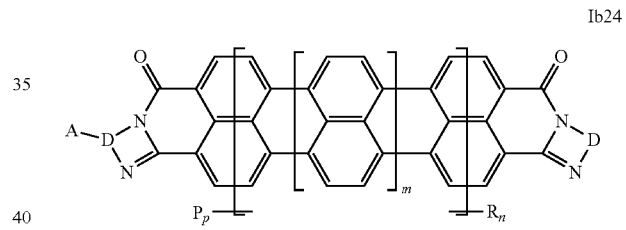

Ib24 may be the corresponding rylene derivatives I' already described in section B.1.4

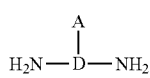

I' which may be subjected to a further condensation reaction with an aromatic diamine of the formula XI

XI $H_2N-\overset{A}{\underset{|}{D}}-NH_2$ in the presence of a nitrogen-basic compound or of phenol as a solvent, and of a Lewis acid or of piperidine as a catalyst.

This condensation reaction can again be undertaken analogously to the preparation of the rylene derivatives I'.

The inventive rylene derivatives I are outstandingly suitable for use in dye-sensitized solar cells.

They exhibit strong absorption in the wavelength range of sunlight and can, depending on the length of the conjugated system, cover a range from about 400 nm (perylene derivatives I) up to about 900 nm (quaterrylene derivatives I). Depending on their composition, rylene derivatives I based on terrylene, in solid state adsorbed on titanium dioxide, absorb in a range from about 400 to 800 nm. In order to achieve very substantial utilization of the incident sunlight from the visible up to within the near infrared region, it is advantageous to use mixtures of different rylene derivatives I. Occasionally, it may even be advisable also to use different rylene homologs.

It is also possible advantageously to combine the rylene derivatives with all n-semiconductors which typically find use in these solar cells. Preferred examples include metal oxides used in ceramics, such as titanium dioxide, zinc oxide, tin(IV) oxide, tungsten(VI) oxide, tantalum(V) oxide, niobium(V) oxide, cesium oxide, strontium titanate, zinc stannate, complex oxides of the perovskite type, for example barium titanate, and binary and ternary iron oxides which may be present in nanocrystalline or amorphous form.

Particularly preferred semiconductors are zinc oxide and titanium dioxide in the anatase modification, which are preferably used in nanocrystalline form.

The metal oxide semiconductors may be used alone or in the form of mixtures. It is also possible to coat a metal oxide with one or more other metal oxides. Moreover, the metal oxides may also be applied as a coating on another semiconductor, for example GaP, ZnP or ZnS.

The nanoparticulate titanium dioxide is typically pressed on or applied to a conductive substrate by a sintering process as a thin porous film with large surface area. Suitable substrates are not only metal foils but also in particular plastics plaques or foils and in particular glass plaques, which are covered with a conductive material, for example transparent conductive oxides (TCOs) such as fluorine- or indium-doped tin oxide (FTO or ITO) and aluminum-doped zinc oxide (AZO), carbon nanotubes or metal films.

The rylene derivatives I may be fixed easily and durably on the metal oxide film. The binding is effected by means of the anhydride function (x1) or the carboxyl groups —COOH or —COO— formed in situ, or by means of the acid groups A present in the imide or condensate radicals ((x2) or (x3)).

The dicarboxylic acid salt of the rylene derivatives I can advantageously be obtained from the anhydride form (x1) by dissolving the anhydride in tetrahydrofuran, alkalizing with an aqueous tetraalkylammonium hydroxide or alkali metal carbonate solution, boiling under reflux for about 1 h, taking up in a mixture of methylene chloride and water, removing the organic phase from the aqueous phase and removing the methylene chloride under reduced pressure.

Owing to the strong absorption of the rylene derivatives I, even thin metal oxide films are sufficient to take up the required amount of rylene derivative. Thin metal oxide films have the advantage that the probability of undesired recombination processes and the internal resistance of the cell are reduced. They are therefore particularly suitable for the production of solid dye solar cells.

The rylene derivatives I can be fixed on the metal oxide films in a simple manner, by contacting the metal oxide films in the freshly sintered (still warm) state, over a sufficient period (from about 0.5 to 24 h) with a solution of the particular rylene derivative I in a suitable organic solvent. This can be done, for example, by immersing the substrate coated with the metal oxide into the solution of the rylene derivative. This simple procedure is suitable owing to its excellent solubility, especially for the rylene derivatives I substituted by (het) aryloxy or -thio radicals R. When combinations of different rylene derivatives I are to be used, they may be applied from one solution comprising all rylene derivatives or successively from different solutions. The most appropriate method can be determined easily in the individual case.

As already described, the rylene derivatives I have a functionality which ensures their fixing on the n-semiconductor film. At the other end of the molecule, they preferably comprise electron donors Y which ease the regeneration of the rylene derivative after the electron is released to the n-semiconductor and also prevent the recombination with electrons already released to the semiconductor.

Preferred electron-donating groups Y are not only the (thio)ether radicals (y2) but in particular also the amino radicals (y1) or imide or condensate radicals (y3) or (y4) which bear (thio)ether groups or amino groups as substituents. Particular preference is given to the imide radicals (y3) substituted by amino groups —$NR^7R^8$ and very particular preference to the amino radicals (y1).

These substituents additionally bring about a bathochromic shift of the absorption and thus extend the spectral region utilizable by the rylene derivatives.

Finally, the rylene derivatives I can be regenerated either with liquid electrolytes or with solid p-conductors.

Examples of liquid electrolytes include redox systems such as iodine/iodide, bromine/bromide and hydroquinone/quinone, and also transition metal complexes which may be dissolved in a polar organic solvent, or present in an ionic liquid or in a gel matrix.

Liquid or liquid-crystalline p-conductors such as triphenylamine derivatives may also be used as p-conductors.

Examples of solid p-semiconductors are inorganic solids such as copper(I) iodide and copper(I) thiocyanate, and in particular organic p-semiconductors based on polymers such as polythiophene and polyarylamines, or on amorphous, reversibly oxidizable, nonpolymeric organic compounds, such as the spirobifluorenes mentioned at the outset or other p-conducting molecules.

Solid p-semiconductors may also be used in the inventive dye-sensitized solar cells without increasing the cell resistance, since the rylene derivatives I absorb strongly and therefore require only thin n-semiconductor layers.

Every compound I has different electronic properties, and the other components of the dye solar cell (n- and p-conductors, additives, etc.) therefore have to be adjusted to each compound.

The inventive dye-sensitized solar cells are otherwise of customary construction, such that further explanations are not required here.

The inventive dye-sensitized solar cells can be used advantageously as an energy source for a series of applications. One example of a particularly interesting possible use is that of obtaining hydrogen and oxygen by electrolytic splitting of water.

Use of combinations of the inventive compounds having different absorption properties allows tandem cells to be produced.

The inventive dye-sensitized solar cells are otherwise constructed as usual, so that further explanations here are not required.

The inventive dye-sensitized solar cells may be used advantageously as an energy source for a series of applications. One example of a possible use which is of particular interest is the generation of hydrogen and oxygen by electrolytic cleavage of water.

EXAMPLES

I. Preparation of Rylene Derivatives I

Example 1

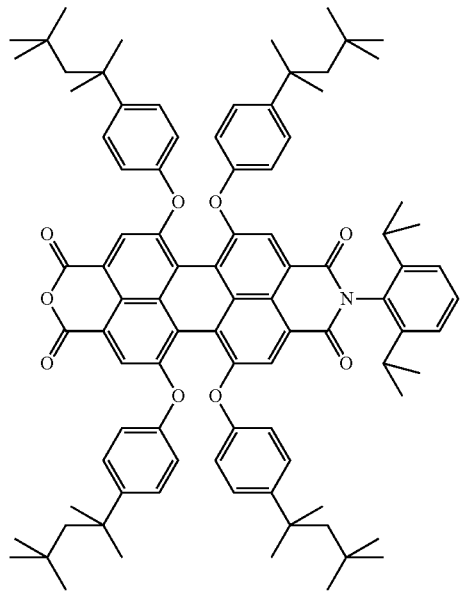

A mixture of 50.0 g (0.033 mol) of N-(2,6-diisopropylphenyl)-1,6,7,12-tetra[(4-tert-octyl)phenoxy]perylene-3-,4:9,10-tetracarboximide and 800 ml of 2-methyl-2-butanol was heated to 60° C. After 0.5 h, 55.2 g (0.98 mol) of potassium hydroxide and 56.9 g (0.98 mol) of potassium fluoride were added. The mixture was then heated to gentle reflux (about 80° C.) and stirred at this temperature for 72 h. The thin layer chromatography analysis of a sample with toluene showed only a trace of reactant.

After cooling to 50° C., acidification with 50% by weight acetic acid and further stirring at 80° C. for two hours, the reaction product was precipitated in water, filtered off, washed with hot water, dried at 70° C. under reduced pressure and then subjected to column chromatography on silica gel with a methylene chloride/hexane mixture (1:1) as the eluent.

19.4 g of I1 were obtained in the form of a red solid, which corresponds to a yield of 49%.

Analytical Data of I1:
$^1$H NMR (500 MHz, CD$_2$Cl$_2$, 25° C.): δ=8.21 (d, 4H); 7.48-7.41 (m, 1H); 7.39-7.27 (m, 10H); 6.90 (d, 8H); 2.70-2.61 (m, 2H); 1.76 (s, 4H); 1.74 (s, 4H); 1.40 (s, 12H); 1.38 (s, 12H); 1.10 (d, 12H); 0.77 (s, 18H); 0.70 (s, 18H) ppm;

UV-Vis (CHCl$_3$): λ$_{max}$ (ε)=584 (47 200), 544 (27 800), 450 (18 600) (M$^{-1}$ cm$^{-1}$);

MS (FD): m/z (rel. int.)=1367.7 (100%) [M$^+$].

Also obtained were 12.2 g (27%) of the analogously substituted perylene-3,4:9,10-tetracarboxylic dianhydride which had the following analytical data:

$^1$H NMR (500 MHz, CDCl$_3$, 25° C.): δ=8.11 (s, 4H); 7.62 (d, 8H); 6.77 (d, 8H); 1.75 (s, 8H); 1.38 (s, 24H); 0.78 (s, 36H) ppm;

UV-Vis (CHCl$_3$): λ$_{max}$ (ε)=584 (42 500), 542 (25 000), 450 (19 000) (M$^{-1}$ cm$^{-1}$);

MS (FD): m/z (rel. int.)=1208.5 (100%) [M$^+$].

Example 2

A mixture of 50.0 g (0.046 mol) of N-(2,6-diisopropylphenyl)-1,6,7,12-tetraphenoxyperylene-3,4:9,10-tetracarboximide and 800 ml of 2-methyl-2-butanol was heated to 60° C. After 0.5 h, 55.2 g (0.98 mol) of potassium hydroxide and 56.9 g (0.98 mol) of potassium fluoride were added. The mixture was then heated to gentle reflux (about 80° C.) and stirred at this temperature for 72 h. The thin layer chromatography analysis of a sample with toluene showed only a trace of reactant.

After cooling to 50° C., acidification with 50% by weight acetic acid and further stirring at 80° C. for two hours, the reaction product was precipitated in water, filtered off, washed with hot water, dried at 70° C. under reduced pressure and then subjected to column chromatography on silica gel with methylene chloride as the eluent.

16.0 g of I2 were obtained in the form of a red solid, which corresponds to a yield of 38%.

Analytical Data of I2:
$^1$H NMR (250 MHz, CD$_2$Cl$_2$, 25° C.): δ=8.17 (s, 2H); 8.16 (s, 2H); 7.46 (t, 1H); 7.35 (d, 2H); 7.33-7.28 (m, 8H); 7.21-7.13 (m, 4H); 7.03-6.97 (m, 8H); 2.73-2.62 (sept, 2H); 1.08 (d, 12H) ppm;

UV-Vis (CHCl$_3$):=611 nm;

MS (FD): m/z (rel. int.)=920 (100%) [M$^+$].

Example 3

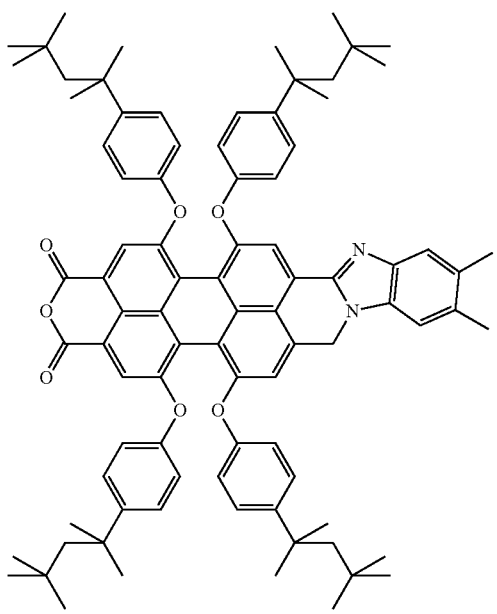

A solution of 0.72 g (0.60 mmol) of N-(2,6-diisopropylphenyl)-1,6,7,12-tetra[(4-tert-octyl)phenoxy]perylene-3-,4:9,10-tetracarboxylic dianhydride in 75 ml of quinoline was initially charged under nitrogen in a 250 ml Schlenk tube, then, likewise under nitrogen, 0.074 g (0.54 mmol) of 4,5-dimethylphenylene-1,2-diamine and 0.28 g (1.5 mmol) of anhydrous zinc acetate were added in succession. The mixture was then heated to 215° C. under nitrogen and kept at this temperature for 40 min under with removal of the water formed. During the reaction, a color change from deep red to dark green was observed.

After cooling to room temperature, the reaction mixture was introduced into 300 ml of 10% by weight hydrochloric acid and stirred for approx. 12 h. The product precipitated in this way was filtered off, washed first with hot water, then with a water/methanol mixture (1:1) and finally with methanol until the runnings were clear, and then subjected to a column filtration on silica gel with chloroform and then with ethanol as the eluent.

0.295 g of I3 were obtained in the form of a blue solid, which corresponds to a yield of 38%.

Analytical Data of I3:
UV-Vis (CHCl$_3$): $\lambda_{max}$ ($\epsilon$)=614 (49 700) nm (M$^{-1}$ cm$^{-1}$);
MS (FD): m/z (rel. int.) 1308.6 (100%) [M$^+$].

Example 4

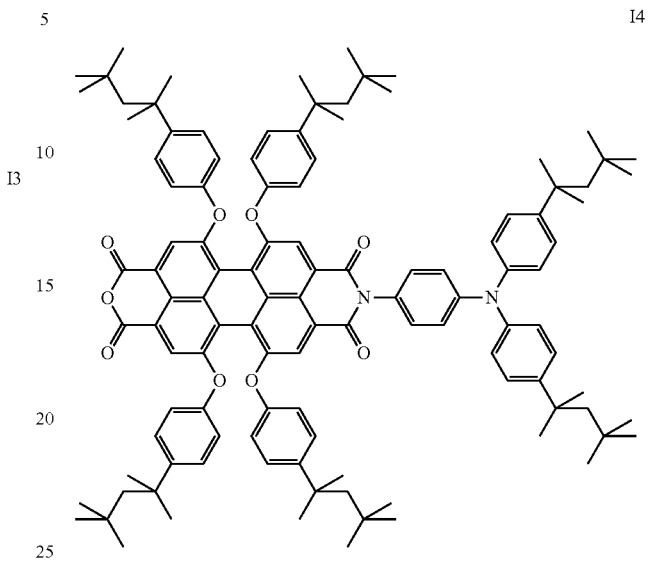

The 4-[bis(4'-tert-octylphenyl)amino]aniline used in the preparation of the rylene derivative I4 was prepared in a two-stage reaction starting from bis(4-tert-octylphenyl) amine as follows:

1) bis(4-tert-Octylphenyl)(4-nitrophenyl)amine

A mixture of 0.70 g (1.0 mol) of tris(dibenzylideneacetone)dipalladium(0), 0.70 g (0.8 mmol) of bis(diphenylphosphino)ferrocene and 7.0 g (70 mmol) of sodium tert-butoxide was stirred at room temperature. After 15 min, 41.0 g (0.2 mol) of 4-bromonitrobenzene and, after a further 15 min, 20 g (50 mmol) of bis(4-tert-octylphenyl)amine were added. The mixture was then heated to 90° C. and stirred at this temperature for 16 h.

The reaction mixture cooled to room temperature was added to 500 ml of water. The organic phase removed by extraction with toluene was washed with water, then the solvent was removed under reduced pressure. The crude product was subjected to column chromatography on silica gel with a methylene chloride/hexane mixture (3:1) as the eluent. The product obtained was recrystallized in methanol.

11.7 g of bis(4-tert-octyldiphenyl)(4-nitrophenyl)amine were obtained in the form of a yellow solid, which corresponds to a yield of 45%

Analytical Data:
$^1$H NMR (500 MHz, CD$_2$Cl$_2$, 25° C.): δ=7.97 (d, 2H); 7.19 (d, 4H); 7.10 (d, 4H); 6.82 (d, 2H); 1.75 (s, 4H); 1.38 (s, 12H); 0.76 (s, 18H) ppm;
MS (FD): m/z (rel. int.)=515 (100%) [M$^+$].

2) 4-[bis(4'-tert-octylphenyl)amino]aniline

A mixture of 5 g (10 mmol) of bis(4-tert-octyldiphenyl)(4-nitrophenyl)amine, 10 g (0.15 mol) of zinc dust and 50 ml of ethanol was cooled to 5° C. with an ice bath. 15 g of glacial acetic acid were then added slowly while maintaining a temperature of 5° C. The mixture was subsequently stirred at room temperature for 5 h.

The zinc dust was filtered off and washed with ethanol. After the ethanol had been removed under reduced pressure, the product was taken up in methylene chloride, and the methylene chloride phase was washed repeatedly with water. After the methylene chloride had been removed under reduced pressure, the product was subjected to a column filtration on silica gel with a toluene/hexane mixture (1:1) as the eluent.

3.6 g of 4-[bis(4'-tert-octylphenyl)amino]aniline were obtained in the form of a yellow-brown oil, which corresponds to a yield of 75%.

Analytical Data:

$^1$H NMR (500 MHz, CD$_2$Cl$_2$, 25° C.): δ=7.21 (d, 4H); 6.89 (m, 6H); 6.62 (d, 2H); 6.82 (d, 2H), 1.72 (s, 4H); 1.38 (s, 12H); 0.76 (s, 18H) ppm;

MS (FD): m/z (rel. int.)=484.5 (100%) [M$^+$].

A solution of 0.70 g (0.56 mmol) of N-(2,6-diisopropylphenyl)-1,6,7,12-tetra[(4-tert-octyl)phenoxy]perylene-3-,4: 9,10-tetracarboxylic dianhydride (obtained according to example 1) in 75 ml of anhydrous N-methylpyrrolidone was initially charged under nitrogen in a 250 ml Schlenk tube, then, likewise under nitrogen, 0.816 g (1.35 mol) of 4-[bis(4'-tert-octylphenyl)amino]aniline and 0.103 g (0.56 mmol) of anhydrous zinc acetate were added in succession. The mixture was then heated to 130° C. under nitrogen and kept at this temperature for 24 h.

After cooling to room temperature, the product was precipitated by slightly acidifying the reaction mixture with 10% by weight hydrochloric acid. The mixture was heated under reflux for 0.5 h. The crude product was filtered off, washed with hot water and then subjected to a column filtration on silica gel with a methylene chloride/hexane mixture (1:1) as the eluent.

0.250 g of I4 were obtained in the form of a red solid, which corresponds to a yield of 27%.

Analytical Data of I4:

$^1$H NMR (500 MHz, CDCl$_3$, 25° C.): δ=8.20 (s, 2H); 8.09 (s, 2H); 7.30-7.25 (m, 8H); 7.23-7.20 (d, 4H); 7.10-7.00 (m, 8H); 6.91 (d, 4H); 6.84 (d, 4H); 1.71-1.67 (m, 12H); 1.33-1.30 (m, 36H); 0.76 (d, 54H) ppm;

UV-Vis (CHCl$_3$): λ$_{max}$=577, 537, 444 nm;

MS (FD): m/z (rel. int.)=1674.2 (100%) [M$^+$].

Example 5

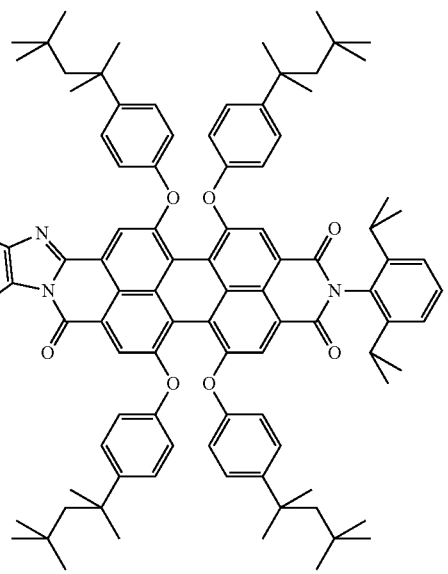

The rylene derivative I5 is a mixture of two isomers with the carboxyl group in the 3- and 4-position on the phenylene ring.

A solution of 0.50 g (0.37 mmol) of N-(2,6-diisopropylphenyl)-1,6,7,12-tetra[(4-tert-octyl)phenoxy]perylene-3,4: 9,10-tetracarboxylic monoimide monoanhydride (obtained according to example 1) in 25 ml of quinoline was initially charged under nitrogen in a 50 ml Schlenk tube, then, likewise under nitrogen, 0.172 g (1.10 mmol) of 3,4-diaminobenzoic acid and 0.20 g (1.10 mmol) of anhydrous zinc acetate were added in succession. The mixture was then heated to 215° C. under nitrogen and, with removal of the water formed, kept at this temperature for 3 h. During the reaction, a color change from deep red to dark blue was observed.

After cooling to room temperature, the reaction mixture was introduced into a mixture of 300 ml of 10% by weight hydrochloric acid and 25 ml of ethanol, and stirred for approx. 12 h. The product precipitated in this way was filtered off, washed first with hot water and then with a water/methanol mixture (95:5), dried at 70° C. under reduced pressure and then subjected to a column filtration on silica gel with chloroform and then with ethanol as the eluent.

0.080 g of I5 were obtained in the form of a blue solid, which corresponds to a yield of 15%.

Analytical Data of the Isomer Mixture I5:

UV-Vis (CHCl$_3$): λmax (ε)=612 (52 000) nm (M$^{-1}$ cm$^{-1}$);

MS (FD): m/z (rel. int.)=1483.7 (100%) [M$^+$].

Example 6

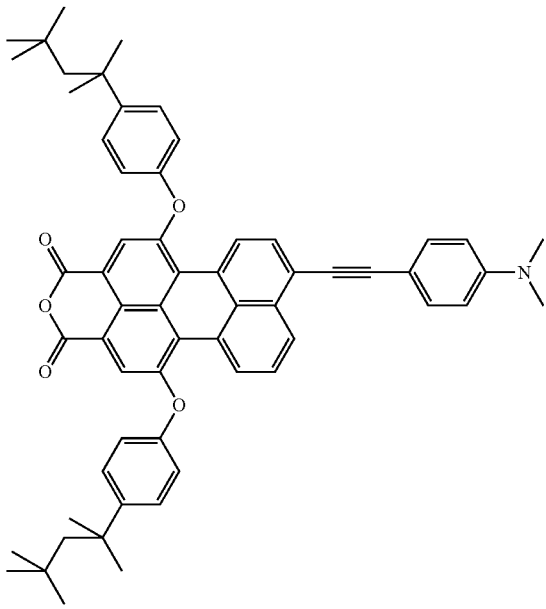

16

The rylene derivative 16 was prepared starting from N-(2,6-diisopropylphenyl)-9-bromo-1,6-bis[(4-tert-octyl)phenoxy]perylene-3,4-dicarboximide which was first reacted under bromine exchange with (4-ethynylphenyl)dimethylamine to give the amino-substituted dicarboximide (step a), which was subsequently hydrolyzed under alkaline conditions to the dicarboxylic anhydride 16 (step b).

Step a):

First 34.7 mg (0.03 mmol) of tetrakis(triphenylphosphine)palladium(0) and 14.6 mg (0.024 mmol) of copper(I) iodide and then 0.09 g (0.62 mmol) of (4-ethynylphenyl)dimethylamine were added to a mixture, stirred under argon, of 0.3 g (0.31 mmol) of N-(2,6-diisopropylphenyl)-9-bromo-1,6-bis[(4-tert-octyl)phenoxy]perylene-3,4-dicarboximide, 25 ml of triethylamine and 25 ml of dry tetrahydrofuran. The mixture was then heated to 60° C. and stirred at this temperature for 12 h.

The reaction mixture, cooled to room temperature, was added to 100 ml of water. The organic phase was removed by extraction with methylene chloride, then the organic solvent was removed by evaporation. The crude product was subjected to column chromatography on silica gel with a methylene chloride/pentane mixture (2:3) as the eluent.

100 mg of N-(2,6-diisopropylphenyl)-9-(4-dimethylaminophenyl)ethynyl-1,6-bis[(4-tert-octyl)phenoxy]perylene-3,4-dicarboximide were obtained in the form of a violet solid, which corresponds to a yield of 31%.

Analytical Data:

$^1$H NMR (250 MHz, CD$_2$Cl$_2$, 25° C.): δ=9.35 (d, J=8 Hz, 1H); 9.26 (d, J=7 Hz, 1H); 8.53 (d, J=8 Hz, 1H); 8.13 (s, 2H); 7.71 (m, 2H); 7.47 (d, J=8 Hz, 2H); 7.36 (m, 5H); 7.23 (d, J=7 Hz, 2H); 7.02 (d, J=8 Hz, 4H); 6.66 (d, J=8 Hz, 2H); 2.94 (m, 6H); 2.60 (m, 2H); 1.65 (s, 4H); 1.30 (s, 12H); 1.02 (d, J=6 Hz, 12H); 0.65 (s, 18H) ppm;

MS (FD): m/z (rel. int.)=1033.2 (100%) [M$^+$].

Step b):

A mixture of 250 mg (0.25 mmol) of N-(2,6-diisopropylphenyl)-9-(4-dimethylaminophenyl)ethynyl-1,6-bis[(4-tert-octyl)phenoxy]perylene-3,4-dicarboximide, 2 g (0.036 mmol) of potassium hydroxide and 500 ml of isopropanol were heated to reflux temperature (about 82° C.) for 2 d.

After cooling to room temperature, the reaction mixture was added to 1 l of water, neutralized with 25% by weight hydrochloric acid, heated to 100° C. and stirred at this temperature for 0.5 h. The product precipitated in this way was filtered off, washed to neutrality with water, dried and subjected to column chromatography on silica gel with a methylene chloride/pentane mixture (1:1) as the eluent.

100 mg of I6 were obtained in the form of a violet solid, which corresponds to a yield of 50%.

Analytical Data of I6:

$^1$H NMR (250 MHz, CD$_2$Cl$_2$, 25° C.): δ=9.29 (d, J=8 Hz, 1H); 9.14 (d, J=8 Hz, 1H); 8.39 (d, J=8 Hz, 1H); 8.00 (s, 1H); 7.98 (s, 1H); 7.54 (m, 2H); 7.40 (d, J=9 Hz, 2H); 7.35 (d, J=9 Hz, 2H); 7.02 (d, J=9 Hz, 4H); 6.60 (d, J=9 Hz, 4H); 2.94 (s, 6H); 2.60 (m, 2H); 1.69 (s, 4H); 1.32 (s, 12H); 0.69 (s, 18H) ppm;

UV-Vis (CH$_2$Cl$_2$): λ$_{max}$ (ε)=570 (35 000) nm (M$^{-1}$ cm$^{-1}$);

MS (FD): m/z (rel. int.)=874.5 (100%) [M$^+$].

Example 7

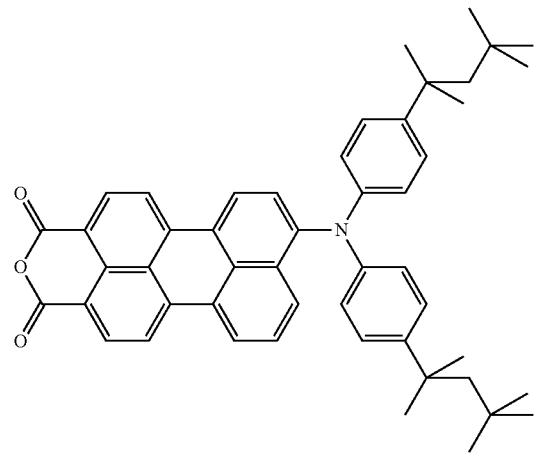

17

The rylene derivative 17 was prepared starting from N-(2,6-diisopropylphenyl)-9-bromoperylene-3,4-dicarboximide which was first reacted under bromine exchange with bis[(4-tert-octyl)phenyl]amine to give the amino-substituted dicarboximide (step a) which was subsequently hydrolyzed under alkaline conditions to give the dicarboxylic anhydride 17 (step b).

Step a):

A mixture of 0.5 g (0.89 mmol) of N-(2,6-diisopropylphenyl)-9-bromoperylene-3,4-dicarboximide, 0.39 g (0.99 mmol) of bis[(4-tert-octyl)phenyl]amine, 40 mg (0.043 mmol) of tris(dibenzylideneacetone)dipalladium(0), 32 mg (0.15 mmol) of tris(tert-butyl)phosphine, 130 mg (0.13 mmol) of sodium tert-butoxide and 100 ml of dry toluene were heated to 80° C. under argon and stirred at this temperature for 1 d.

After the solvent had been distilled off, the crude product was subjected to column chromatography on silica gel with a methylene chloride/pentane mixture (1:2) as the eluent.

0.59 g of N-(2,6-diisopropylphenyl)-9-[bis(4-tert-octyl) phenyl]aminoperylene-3,4-di-carboximide was obtained in the form of a blue solid, which corresponds to a yield of 77%.

Analytical Data:

$^1$H NMR (250 MHz, CD$_2$Cl$_2$, 25° C.): δ=8.55 (m, 2H); 8.42 (m, 4H); 7.97 (d, J=8 Hz, 1H); 7.45 (m, 2H); 7.28 (d, J=7 Hz, 3H); 7.20 (d, J=8 Hz, 4H); 6.92 (d, J=8 Hz, 2H); 2.70 (m, 2H); 1.63 (s, 4H); 1.27 (s, 12H); 1.06 (d, J=6 Hz, 12H); 0.67 (s, 18H) ppm;

MS (FD): m/z (rel. int.)=873.8 (100%) [M$^+$].

Step b):

A mixture of 250 mg (0.29 mmol) of N-(2,6-diisopropylphenyl)-9-[bis(4-tert-octyl)phenyl]aminoperylene-3,4-dicarboximide, 2 g (0.036 mol) of potassium hydroxide and 500 ml of isopropanol was heated to reflux temperature (about 82° C.) for 2 d.

After cooling to room temperature, the reaction mixture was added to 1 l of water, neutralized with 25% by weight hydrochloric acid, heated to 100° C. and stirred at this temperature for 0.5 h. The product precipitated in this way was filtered off, washed to neutrality with water, dried and subjected to column chromatography on silica gel with a methylene chloride/pentane mixture (1:1) as the eluent.

40 mg of I7 were obtained in the form of a blue solid, which corresponds to a yield of 18%.

Analytical Data of I7:

$^1$H NMR (250 MHz, CD$_2$Cl$_2$, 25° C.): δ=8.50 (m, 2H); 8.37 (m, 4H); 7.99 (d, J=9 Hz, 1H); 7.34 (m, 2H); 7.21 (d, J=9 Hz, 4H); 6.91 (d, J=9 Hz, 4H); 1.63 (s, 4H); 1.27 (s, 12H); 0.67 (s, 18H) ppm;

UV-Vis (CH$_2$Cl$_2$): $\lambda_{max}$ (ε)=605 (21 000) nm (M$^{-1}$ cm$^{-1}$);

MS (FD): m/z (rel. int.)=714.0 (100%) [M$^+$].

Example 8

I8

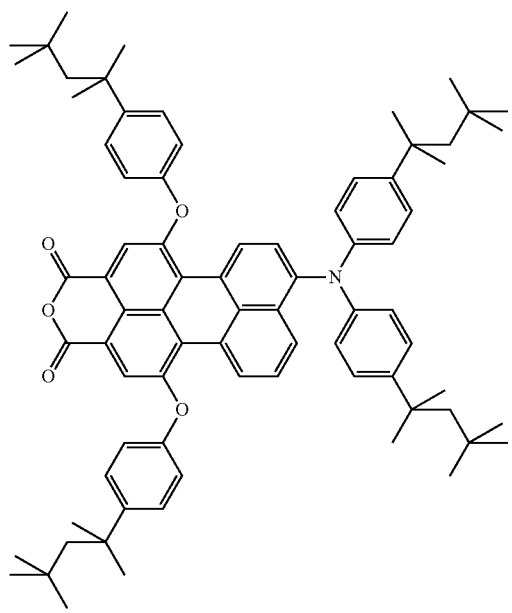

The rylene derivative 18 was prepared starting from N-(2,6-diisopropylphenyl)-1,6-bis[(4-tert-octyl)phenoxy]-9-bromoperylene-3,4-dicarboximide which was first reacted under bromine exchange with bis[(4-tert-octyl)phenyl]amine to give the amino-substituted dicarboximide (step a) which was subsequently hydrolyzed under alkaline conditions to the dicarboxylic anhydride 18 (step b).

Step a):

A mixture of 0.86 g (0.89 mmol) of N-(2,6-diisopropylphenyl)-1,6-bis[(4-tert-octyl)phenoxy]-9-bromoperylene-3,4-dicarboximide, 0.39 g (0.99 mmol) of bis(4-tert-octylphenyl) amine, 130 mg (0.13 mmol) of tris(dibenzylideneacetone) dipalladium(0), 32 mg (0.15 mmol) of tris(tert-butyl) phosphine, 130 mg (0.13 mmol) of sodium tert-butoxide and 100 ml of dry toluene was heated to 80° C. under argon and stirred at this temperature for 1 d.

After the solvent had been distilled off, the crude product was subjected to column chromatography on silica gel with a methylene chloride/pentane mixture (1:2) as the eluent.

1 g of N-(2,6-diisopropylphenyl)-1,6-bis[(4-tert-octyl) phenoxy]-9-[bis(4-tertoct-yl)phenyl]aminoperylene-3,4-dicarboximide was obtained in the form of a blue solid, which corresponds to a yield of 88%.

Analytical Data:

$^1$H NMR (250 MHz, CD$_2$Cl$_2$, 25° C.): δ=9.34 (m, 2H); 8.21 (s, 2H); 8.09 (d, J=8 Hz, 1H); 7.44 (m, 5H); 7.33 (m, 8H); 7.08 (m, 4H); 6.97 (d, J=8 Hz, 4H); 2.72 (m, 2H); 1.75 (d, J=9 Hz, 8H); 1.39 (d, J=10 Hz, 24H); 1.13 (d, J=7 Hz, 12H); 0.74 (s, 36H) ppm;

MS (FD): m/z (rel. int.)=1291.3 (100%) [M$^+$].

Step b):

A mixture of 250 mg (0.20 mmol) of N-(2,6-diisopropylphenyl)-1,6-bis[(4-tertoctyl)phenoxy]-9-[bis(4-tert-oct-yl) phenyl]aminoperylene-3,4-dicarboximide, 2 g (0.036 mol) of potassium hydroxide and 500 ml of isopropanol was heated to reflux temperature (about 82° C.) for 2 d.

After cooling to room temperature, the reaction mixture was added to 1 l of water, neutralized with 25% by weight hydrochloric acid, heated to 100° C. and stirred at this temperature for 0.5 h. The product precipitated in this way was filtered off, washed to neutrality with water, dried and subjected to column chromatography on silica gel with a methylene chloride/pentane mixture (1:1) as the eluent. 100 mg of 18 were obtained in the form of a blue solid, which corresponds to a yield of 40%.

Analytical Data of 18:

$^1$H NMR (250 MHz, CD$_2$Cl$_2$, 25° C.): δ=9.33 (m, 2H); 8.14 (s, 2H); 8.09 (d, J=8 Hz, 1H); 7.44 (m, 4H); 7.22 (m, 6H); 7.08 (m, 4H); 6.95 (d, J=8 Hz, 4H); 1.76 (d, J=16 Hz, 8H); 1.39 (d, J=16 Hz, 24H); 0.73 (m, 36H) ppm;

UV-Vis (CH$_2$Cl$_2$): $\lambda_{max}$ (ε)=600 (32 000) nm (M$^{-1}$ cm$^{-1}$);

MS (FD): m/z (rel. int.)=1122.4 (100%) [M$^+$].

Example 9

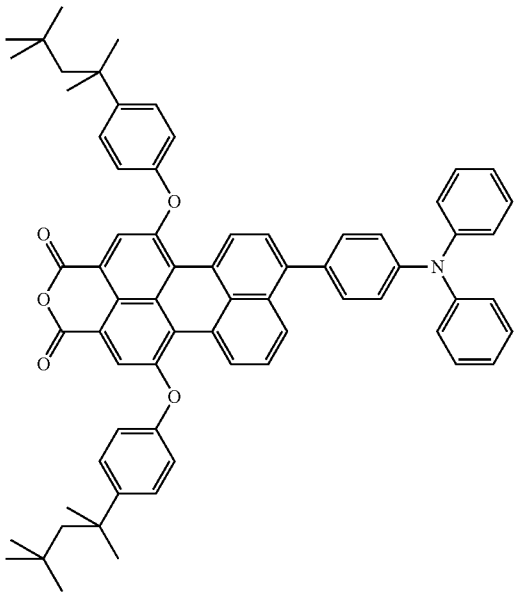

The rylene derivative I9 was prepared starting from N-(2,6-diisopropylphenyl)-1,6-bis[(4-tert-octyl)phenoxy]-9-(4,4,5,5-tetra-methyl-1,3,2-dioxaboran-2-yl)-perylene-3,4-dicarboximide which was first subjected to a Suzuki coupling with N,N-diphenyl-4-bromoaniline to give the aminophenyl-substituted dicarboximide (step a) which was then hydrolyzed under alkaline conditions to the dicarboxylic anhydride I9 (step b).

Step a):

A mixture of 400 mg (0.4 mmol) of N-(2,6-diisopropylphenyl)-1,6-bis[(4-tert-octyl)phenoxy]-9-(4,4,5,5-tetra-methyl-1,3,2-dioxaboran-2-yl)perylene-3,4-dicarboximide, 193 mg (0.6 mmol) of N,N-diphenyl-4-bromoaniline and 70 ml of dry toluene was initially charged under argon in a 250 ml Schlenk tube, then, likewise under argon, 15 ml of a 1 M aqueous potassium carbonate solution and 80 mg (0.07 mmol) of tetrakis(triphenylphosphine)palladium(0) were added. The mixture was then heated to 90° C. under argon and kept at this temperature for 16 h.

After cooling to room temperature, the organic phase was removed, then the solvent was removed under reduced pressure. The resulting crude product was subjected to column chromatography on silica gel with methylene chloride as the eluent.

200 mg of N-(2,6-diisopropylphenyl)-1,6-bis[(4-tert-octyl)phenoxy]-9-[(4-diphenylamino)phenyl]perylene-3,4-dicarboximide were obtained in the form of a violet solid, which corresponds to a yield of 45%.

Analytical Data:

$^1$H NMR (250 MHz, CD$_2$Cl$_2$, 25° C.): δ=9.37 (m, 2H); 8.23 (s, 2H); 8.14 (d, J=8 Hz, 1H); 7.59 (m, 2H); 7.44 (m, 7H); 7.34 (m, 6H); 7.20 (d, J=8 Hz, 6H); 7.08 (m, 6H); 2.70 (m, 2H); 1.73 (s, 4H); 1.37 (s, 12H); 1.11 (d, J=7 Hz, 12H); 0.72 (s, 18H) ppm;

MS (FD): m/z (rel. int.)=1133.1 (100%) [M$^+$].

Step b):

A mixture of 200 mg (0.18 mmol) of N-(2,6-diisopropylphenyl)-1,6-bis[(4-tertoctyl)phenoxy]-9-[(4-di-phenylamino)phenyl]perylene-3,4-dicarboximide, 2 g (0.036 mol) of potassium hydroxide, 1 g (0.017 mol) of potassium fluoride and 500 ml of isopropanol was heated to reflux temperature (about 82° C.) for 1 d.

After cooling to room temperature, the reaction mixture was added to 1 l of water, neutralized with 25% by weight hydrochloric acid, heated to 100° C. and stirred at this temperature for 0.5 h. The product precipitated in this way was filtered off, washed to neutrality with water, dried and subjected to column chromatography on silica gel with a methylene chloride/pentane mixture (1:1) as the eluent.

100 mg of I9 were obtained in the form of a blue solid, which corresponds to a yield of 61%.

Analytical Data of I9:

$^1$H NMR (500 MHz, CD$_2$Cl$_2$, 25° C.): δ=9.36 (m, 2H); 8.15 (d, J=8 Hz, 1H); 8.08 (s, 2H); 7.60 (m, 2H); 7.42 (m, 6H); 7.31 (m, 4H); 7.20 (d, J=8 Hz, 6H); 7.04 (m, 6H); 1.76 (s, 4H); 1.40 (s, 12H); 0.77 (s, 18H) ppm;

UV-Vis (CH$_2$Cl$_2$): λ$_{max}$ (ε)=541 (35 000) nm (M$^{-1}$ cm$^{-1}$);

MS (FD): m/z (rel. int.)=974.8 (100%) [M$^+$].

Example 10

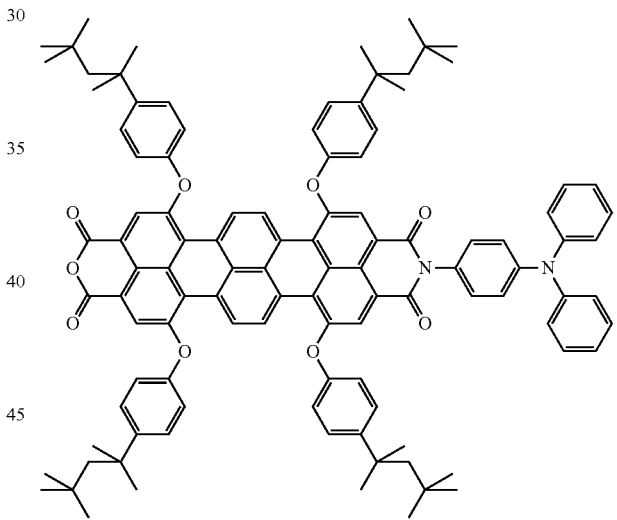

0.028 g (0.15 mmol) of anhydrous zinc acetate and 0.039 g (0.15 mmol) of 4-diphenylaminoaniline were added under nitrogen to a mixture of 0.250 g (0.19 mmol) of 1,6,9,14-tetra [(4-tert-octyl)phenoxy]-terrylene-3,4:11,12-tetracarboxylic dianhydride and 25 ml of anhydrous N-methylpyrrolidone. The mixture was then heated to 130° C. under nitrogen and stirred at this temperature for 24 h.

After cooling to room temperature, the product was precipitated by adding 10% by weight hydrochloric acid, filtered off, washed first with 10% by weight hydrochloric acid and then with hot water, and then subjected to column chromatography on silica gel with toluene as the eluent.

0.03 g of I10 was obtained in the form of a blue-green solid, which corresponds to a yield of 10%.

Analytical Data of I10:

$^1$H NMR (400 MHz, CDCl$_3$, 25° C.): δ=9.51 (s, 4H); 8.27 (s, 2H); 8.15 (s, 2H); 7.49-7.40 (m, 8H); 7.29-7.21 (m, 6H);

2.70 (m, 2H); 1.79 (d, 8H, J=15.0 Hz); 1.40 (d, 24H, J=11.0 Hz); 1.02 (d, 12H, J=6.8 Hz); 0.75 (d, 36H, J=24.0 Hz) ppm;
UV-Vis (toluene): $\lambda_{max}$=670, 616 nm;
MS (FD): m/z (rel. int.)=1575.7 (100%) [M$^+$].

Example 11

I11

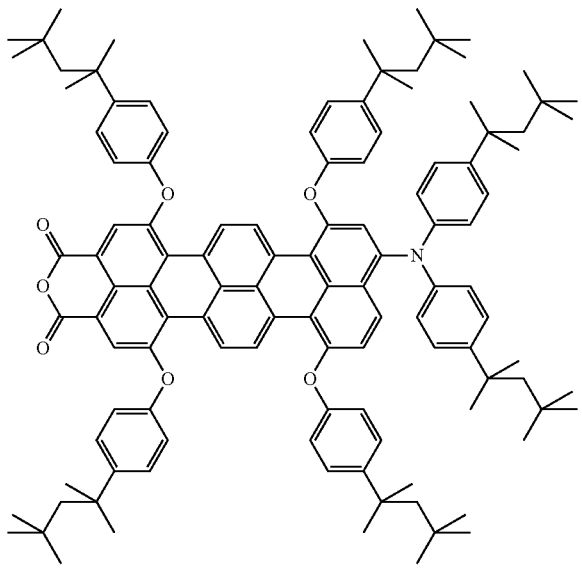

The rylene derivative I11 was prepared starting from N-(2,6-diisopropylphenyl)-1,6,9,14-tetra[(4-tert-octyl)phenoxy]-11-bromot-errylene-3,4-dicarboximide which was first reacted under bromine exchange with bis[(4-tert-octyl)phenyl]amine to give the amino-substituted dicarboximide (step a) which was subsequently hydrolyzed under alkaline conditions to the dicarboxylic anhydride I11 (step b).

Step a):

A mixture of 0.39 g (0.26 mmol) of N-(2,6-diisopropylphenyl)-1,6,9,14-tetra[(4-tert-octyl)phenoxy]-11-bromot-errylene-3,4-dicarboximide, 0.119 g (0.28 mmol) of bis(4-tert-octylphenyl)amine, 0.01 g (0.012 mmol) of tris(dibenzylideneacetone)dipalladium(0), 0.1 g (0.11 mmol) of tris(tert-butyl)phosphine, 0.01 g (0.05 mmol) of sodium tert-butoxide and 20 ml of dry toluene was heated to 80° C. under argon and stirred at this temperature for 16 h.

After the solvent had been distilled off, the crude product was subjected to column chromatography on silica gel with a hexane/ethyl acetate mixture (10:1) as the eluent.

0.29 g of N-(2,6-diisopropylphenyl)-1,6,9,14-tetra[(4-tert-octyl)phenoxy]-9-[bis(4-tert-octyl)phenyl]aminoterrylene-3,4-dicarboximide was obtained in the form of a blue solid, which corresponds to a yield of 61%.

Analytical Data:
MS (FD): m/z (rel. int.)=1653.9 (100%) [M$^+$].

Step b):

A mixture of 0.30 g (0.17 mmol) of N-(2,6-diisopropylphenyl)-1,6,9,14-tetra[(4-tert-octyl)phenoxy]-9-[bis(4-tert-octyl)phenyl]aminoterrylene-3,4-dicarboximide and 30 ml of 2-methyl-2-butanol was heated to 60° C. After 0.5 h, 0.28 g (5 mmol) of potassium hydroxide and 0.29 g (5 mmol) of potassium fluoride were added. The mixture was then heated to gentle reflux (about 118° C.) and stirred at this temperature for 16 h.

After cooling to 50° C., acidification with 50% by weight acetic acid and further stirring at 80° C. for 2 hours, the reaction product was precipitated in water, filtered off, washed with hot water, dried at 70° C. under reduced pressure and then subjected to column chromatography on silica gel with an ethyl acetate/hexane mixture (1:19) as the eluent.

0.16 g of I11 was obtained in the form of a blue-green solid, which corresponds to a yield of 59%.

Analytical Data of I11:
$^1$H NMR (500 MHz, CD$_2$Cl$_2$, 25° C.): δ=9.41-9.38 (m, 4H); 9.09 (dd, 2H); 8.10 (s, 2H); 7.83 (d, 1H); 7.42 (d, 4H); 7.38 (d, 2H); 7.27 (d, 2H); 7.20 (d, 4H); 7.06 (d, 4H); 7.00-6.97 (m, 3H); 6.95-6.87 (m, 7H); 1.75-1.69 (m, 12H); 1.40-1.30 (m, 36H); 0.75-0.65 (m, 54H) ppm;
UV-Vis (CH$_2$Cl$_2$): $\lambda_{max}$=692 nm;
MS (FD): m/z (rel. int.)=1653.9 (100%) [M$^+$].

Example 12

I12

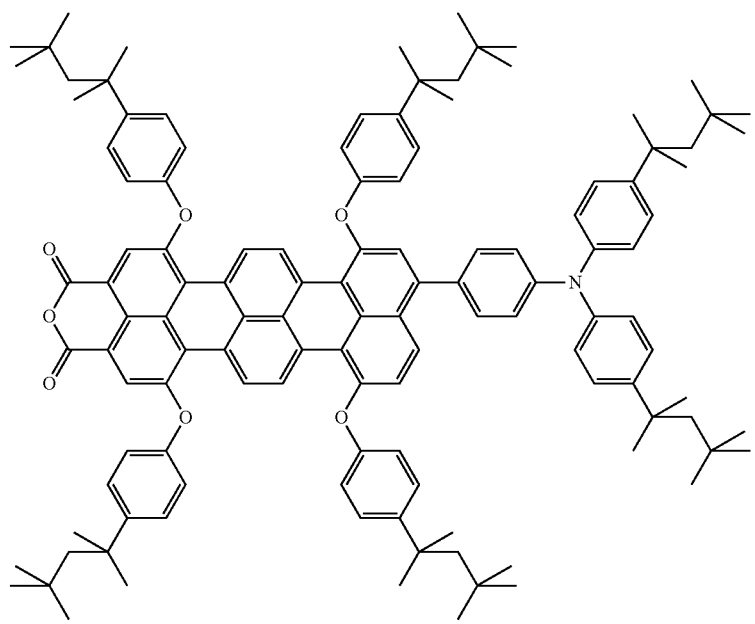

The rylene derivative I12 was prepared starting from N-(2,6-diisopropylphenyl)-1,6,9,14-tetra[(4-tert-octyl)phenoxy]-11-bromot-errylene-3,4-dicarboximide which was first subjected to a Suzuki coupling with N,N-bis[(4-tert-octyl)phenyl]-4-(4,4,5,5-tetramethyl-1,3,2-dioxabora-n-2-yl)aniline to give the aminophenyl-substituted dicarboximide (step a) which was subsequently hydrolyzed under alkaline conditions to the dicarboxylic anhydride I12 (step b).

The N,N-bis[(4-tert-octyl)phenyl]-4-(4,4,5,5-tetramethyl-1,3,2-diox-aboran-2-yl)aniline used as a reactant in step a) was prepared in a two-stage reaction starting from bis(4-tert-octylphenyl)amine as follows:

1) bis(4-tert-octylphenyl)(4-bromophenyl)amine

A mixture of 12 g (30 mmol) of bis(4-tert-octylphenyl)amine, 9.4 g (0.04 mmol) of 1,4-dibromobenzene and 20 ml of anhydrous toluene was stirred at room temperature. After 10 min, 0.14 g (0.16 mmol) of tris(dibenzylideneacetone)dipalladium(0), 0.15 g (0.24 mmol) of BINAP and 1.2 g (12 mmol) of sodium tert-butoxide were added. The mixture was then heated to 90° C. and stirred at this temperature for 72 h.

The reaction mixture, cooled to room temperature, was added to 100 ml of water. The organic phase removed by extraction with toluene was washed with water, then the solvent was removed under reduced pressure. The crude product was subjected to column chromatography on silica gel with hexane as the eluent.

5.9 g of a white solid were obtained, which corresponds to a yield of 36%.
Analytical Data:
$^1$H NMR (500 MHz, CDCl$_3$, 25° C.): δ=7.29-7.27 (m, 6H); 6.95 (d, 4H); 6.85 (d, 2H); 6.82 (d, 2H); 1.75 (s, 4H); 1.38 (s, 12H); 0.76 (s, 18H) ppm;
MS (FD): m/z (rel. int.)=322 (100%) [M$^+$].

2) N,N-bis[(4-tert-octyl)phenyl]-4-(4,4,5,5-tetramethyl-1,3,2-dioxaboran-2-yl)aniline A mixture of 3 g (5 mmol) of bis(4-tert-octylphenyl)(4-bromophenyl)amine, 1.3 g (14 mmol) of potassium acetate, 3.7 g (15 mmol) of bis(pinacolato)diborane and 0.2 g (0.3 mmol) of [1,1'-bis(diphenylphosphino)ferrocene]palladium(II) chloride and 45 ml of dioxane was heated to 70° C. under nitrogen and stirred at this temperature for 16 h.

After cooling to room temperature, the solvent was removed under reduced pressure. The crude product was subjected to column chromatography on silica gel with a methylene chloride/hexane mixture (1:1) as the eluent.

1.6 g of N,N-bis[(4-tert-octyl)phenyl]-4-(4,4,5,5-tetramethyl-1,3,2-dioxaboran-2-y-l)aniline were obtained in the form of a white solid, which corresponds to a yield of 54%.
Analytical Data:
$^1$H NMR (500 MHz, CDCl$_3$, 25° C.): δ=7.57 (d, 2H); 7.28 (d, 4H); 7.00 (d, 4H); 6.92 (d, 2H); 1.74 (s, 4H); 1.38 (s, 12H); 0.76 (s, 18H) ppm;
MS (FD): m/z (rel. int.)=596.4 (100%) [M$^+$].

Step a):
0.021 g (0.01 mmol) of tetrakis(triphenylphosphine)palladium(0) and 0.1 g (0.072 mol) of potassium carbonate, dissolved in 1 ml of a water/ethanol mixture (10:1), were added under nitrogen to a mixture of 0.3 g (0.20 mmol) of N-(2,6-diisopropylphenyl)-1,6,9,14-tetra[(4-tert-octyl)phenoxy]-11-bromot-errylene-3,4-dicarboximide, 0.525 g (0.88 mmol) of N,N-bis[(4-tert-octyl)phenyl]-4-(4,4,5,5-tetramethyl-1,3,2-dioxaboran-2-y-l)aniline and 25 ml of dry toluene. The mixture was then heated to 80° C. under nitrogen and kept at this temperature for 16 h.

After cooling to room temperature, the solvent was removed under reduced pressure. The resulting crude product was subjected to column chromatography on silica gel with a methylene chloride/hexane mixture (1:1) as the eluent.

0.22 g of N-(2,6-diisopropylphenyl)-1,6,9,14-tetra[(4-tert-octyl)phenoxy]-11-[4-(N,N-bis(4-tert-octylphenyl)amino)phenyl]terrylene-3,4-dicarboximide was obtained in the form of a blue solid, which corresponds to a yield of 58%.
Analytical Data:
$^1$H NMR (500 MHz, CDCl$_3$, 25° C.): δ=9.42-9.38 (m, 2H); 9.18-9.12 (m, 2H); 8.27 (s, 2H); 7.95-7.91 (m, 1H); 7.43-7.40 (m, 1H); 7.40-7.32 (m, 8H); 7.30-7.32 (m, 9H); 7.10-7.00 (m, 15H); 2.72-2.68 (m, 2H); 1.75-1.69 (m, 12H); 1.40-1.25 (m, 36H); 0.80-0.70 (m, 54H) ppm;
MS (FD): m/z (rel. int.)=1889.2 (100%) [M$^+$].

Step b):
A mixture of 0.10 g (0.053 mmol) of N-(2,6-diisopropylphenyl)-1,6,9,14-tetra[(4-tert-octyl)phenoxy]-11-[4-(N,—N-bis(4-tert-octylphenyl)amino)phenyl]terrylene-3,4-dicarboximide and 18 ml of 2-methyl-2-butanol was heated to 60° C. After 0.5 h, 0.089 g (1.59 mmol) of potassium hydroxide and 0.093 g (1.59 mmol) of potassium fluoride were added. The mixture was then heated to gentle reflux (about 118° C.) and stirred at this temperature for 21 h.

After cooling to 50° C., the reaction mixture was slightly acidified with 50% by weight acetic acid and stirred at this temperature for 1 h. The product was precipitated in 250 ml of water, filtered off, washed to neutrality with water, dried at 70° C. under reduced pressure and then subjected to column chromatography on silica gel with a chloroform/ethanol mixture (19:1) as the eluent.

0.8 g of I12 was obtained in the form of a blue-green solid, which corresponds to a yield of 87%.
Analytical Data of I12:
UV-Vis (CH$_2$Cl$_2$): λ$_{max}$=676 nm;
MS (FD): m/z (rel. int.)=1730.0 (100%) [M$^+$].

Example 13

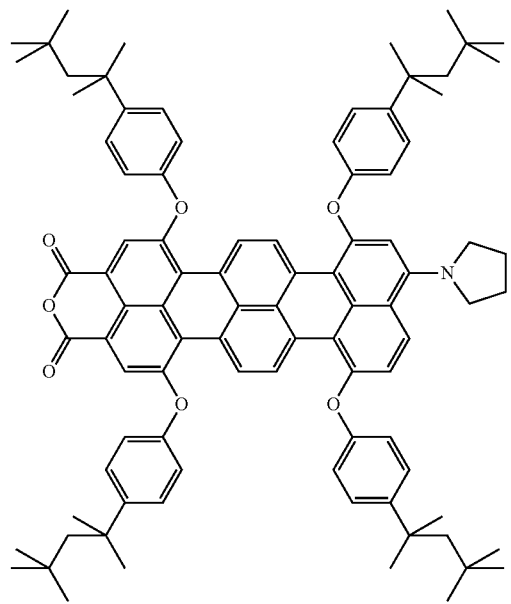

I13

The rylene derivative I13 was prepared starting from N-(2,6-diisopropylphenyl)-1,6,9,14-tetra[(4-tert-octyl)phenoxy]-11-bromot-errylene-3,4-dicarboximide which was first reacted under bromine exchange with pyrrolidine to give the pyrrolidyl-substituted dicarboximide (step a) which was subsequently hydrolyzed under alkaline conditions to the dicarboxylic anhydride I13 (step b).

Step a):

0.51 ml (6 mmol) of pyrrolidine was added under nitrogen to a solution of 0.10 g (0.07 mmol) of N-(2,6-diisopropylphenyl)-1,6,9,14-tetra[(4-tert-octyl)phenoxy]-11-bromot-errylene-3,4-dicarboximide in 10 ml of dimethylformamide, then the mixture was heated to 90° C. under nitrogen. After 3 h, a color change from blue to green was observed.

After cooling to room temperature, the solvent was distilled off under reduced pressure. The crude product was subjected to column chromatography on silica gel with chloroform as the eluent.

0.065 g of N-(2,6-diisopropylphenyl)-1,6,9,14-tetra[(4-tert-octyl)phenoxy]-9-pyrroli-dylterrylene-3,4-dicarboximide was obtained in the form of a blue solid, which corresponds to a yield of 65%.

Analytical Data:
UV-Vis (CHCl$_3$): $\lambda_{max}$ ($\epsilon$)=706 (83 000) nm (M$^{-1}$ cm$^{-1}$);
MS (FD): m/z (rel. int.)=1490.7 (100%) [M$^+$].

Step b):

A mixture of 0.30 g (0.17 mmol) of N-(2,6-diisopropylphenyl)-1,6,9,14-tetra[(4-tert-octyl)phenoxy]-9-[bis(4-tert-octyl)phenyl]aminoterrylene-3,4-dicarboximide and 30 ml of 2-methyl-2-butanol was heated to 60° C. After 0.5 h, 0.28 g (5 mmol) of potassium hydroxide and 0.29 g (5 mmol) of potassium fluoride were added. The mixture was then heated to gentle reflux (about 118° C.) and stirred at this temperature for 16 h.

After cooling to 50° C., acidification with 50% by weight acetic acid and further stirring at 80° C. for 2 hours, the reaction product was precipitated in water, filtered off, washed with hot water, dried at 70° C. under reduced pressure and then subjected to column chromatography on silica gel with an ethyl acetate/hexane mixture (1:19) as the eluent.

0.16 g of I13 was obtained in the form of a blue-green solid, which corresponds to a yield of 59%.

Analytical Data of I13:
$^1$H NMR (500 MHz, CD$_2$Cl$_2$, 25° C.): δ=9.41-9.38 (m, 4H); 9.09 (dd, 2H); 8.10 (s, 2H); 7.83 (d, 1H); 7.42 (d, 4H); 7.38 (d, 2H); 7.27 (d, 2H); 7.20 (d, 4H); 7.06 (d, 4H); 7.00-6.97 (m, 3H); 6.95-6.87 (m, 7H); 1.75-1.69 (m, 12H); 1.40-1.30 (m, 36H); 0.75-0.65 (m, 54H) ppm;
MS (FD): m/z (rel. int.)=1653.9 (100%) [M$^+$].

Example 14

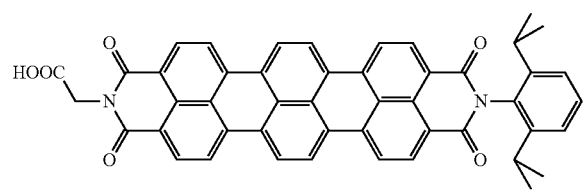

I14

A mixture of 69.9 g (0.71 mol) of sodium tert-butoxide, 68.4 ml of diethylene glycol diethyl ether and 126.5 ml (0.85 mol) of DBU was heated to 60° C. in a Schlenk tube with stirring and under nitrogen. After 20 min, 17.6 g (0.035 mol) of N-(2,6-diisopropylphenyl)perylene-3,4-dicarboximide and, after a further 5 min, 18.0 g (0.071 mol) of N-(2-carboxyethyl)naphthalene-1,8-dicarboximide were added under nitrogen. The mixture was then heated to 120° C. under nitrogen and stirred at this temperature for 6 h.

After cooling to room temperature, the reaction mixture was left to stand under air for about 12 h and then added to 3 l of water. The product precipitated in this way was filtered off, washed with water and dried, then acidified with 13% by weight hydrochloric acid, washed again with water and dried, and finally boiled first in methanol and then in ethanol, filtered off, washed with hot water and dried.

4.34 g of I14 were obtained in the form of a blue solid, which corresponds to a yield of 13%.

Analytical Data of I14:
MS (FD): m/z (rel. int.)=733.2 (100%) [M$^+$].

Example 15

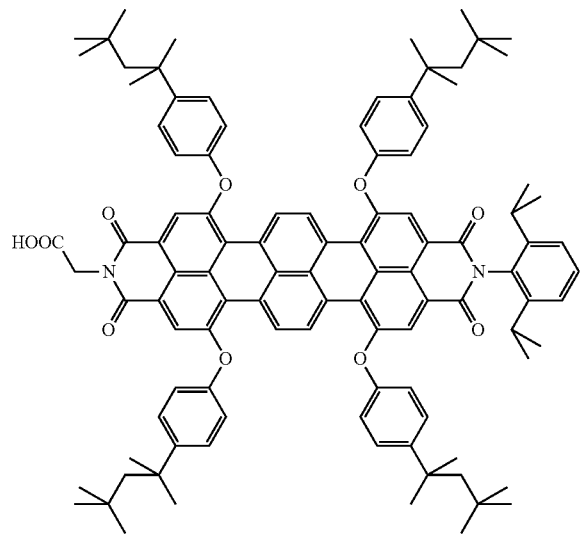

I15

To prepare the rylene derivative I15, the rylene derivative I13 unsubstituted in the rylene skeleton was first converted by reaction with bromine to the tetrabromo derivative (step a) which was then reacted with 4-(tert-octyl)phenol to give the rylene derivative I15 (step b).

Step a):

A mixture of 0.3 g (4 mmol) of I13 in 40 ml of chloroform was heated to 60° C. and stirred at this temperature for 10 min. After cooling to 40° C., first 80 ml of water and then 16.0 g (0.10 mol) of bromine were added. The mixture was then stirred at 40° C. for 10 h. The course of reaction was monitored by thin layer chromatography (eluent: 3:1 methylene chloride/acetone).

After cooling to room temperature and removal of the excess bromine with nitrogen, the reaction mixture was stirred further after addition of an aqueous solution of sodium disulfite and methylene chloride. The organic phase removed was dried with magnesium sulfate, then the solvent was removed under reduced pressure.

3.5 g of 1,6,9,14-tetrabrominated rylene derivative I13 were obtained, which corresponds to a yield of 83%.

Analytical Data:

MS (FD): m/z (rel. int.)=1048.6 (100%) [M$^+$].

Step b):

A mixture of 3.0 g (2.9 mmol) of 1,6,9,14-tetrabrominated rylene derivative I13 and 200 ml of anhydrous N-methylpyrrolidone was purged with nitrogen, then 4.4 g (21.8 mmol) of tert-octylphenol and 2.2 g (16.0 mmol) of potassium carbonate were added. The mixture was then heated to 80° C. and stirred at this temperature for 16 h.

After cooling to room temperature, the product was precipitated by adding 100 ml of dilute hydrochloric acid, filtered off, washed to neutrality with water and dried.

2.0 g of I15 were obtained in the form of a blue solid, which corresponds to a yield of 43%.

Analytical Data of I15:

UV-Vis (ethanol): $\lambda_{max}$=665, 623 nm;

MS (FD): m/z (rel. int.)=1550.3 (100%) [M$^+$].

Example 16

The N-(4-carboxyphenyl)naphthalene-1,8-dicarboximide used in the preparation of the rylene derivative I16 was prepared as follows.

7.34 g (0.04 mmol) of anhydrous zinc acetate and 21.94 g (0.16 mmol) of 4-aminobenzoic acid were added under nitrogen to a mixture, initially charged under nitrogen, of 8.24 g (0.04 mmol) of naphthalene-1,8-dicarboxylic anhydride and 40 ml of anhydrous N-methylpyrrolidone. The mixture was then heated to 160° C. and stirred at this temperature for 15 h.

After cooling to room temperature, the product was precipitated by adding 1 l of 5% by weight hydrochloric acid, filtered off, washed first with 5% by weight hydrochloric acid and then with hot water, and dried.

12.7 g of N-(4-carboxyphenyl)naphthalene-1,8-dicarboximide were obtained in the form of a white solid, which corresponds to a yield of 100%.

Analytical Data:

UV-Vis (CH$_2$Cl$_2$): $\lambda_{max}$=640, 595 nm;

$^1$H NMR (400 MHz, THF, 25° C.): δ=8.58 (d, 2H); 8.39 (d, 2H); 8.17 (d, 2H); 7.91 (t, 2H); 7.07 (d, 2H) ppm.

A mixture of 49.9 g (0.50 mol) of sodium tert-butoxide, 47.4 ml of diethylene glycol diethyl ether and 90.3 ml (0.61 mol) of DBU was heated to 60° C. in a Schlenk tube with stirring and under nitrogen. After 20 min, 12.6 g (0.023 mol) of N-(2,6-diisopropyl-phenyl)perylene-3,4-dicarboximide and, after a further 5 min, 16.0 g (0.050 mol) of N-(4-carboxyphenyl)naphthalene-1,8-dicarboximide were added under nitrogen. The mixture was then heated to 120° C. under nitrogen and stirred at this temperature for 6 h.

After cooling to 60° C. and addition of 150 ml of water, the reaction mixture was left to stand under air for about 12 h and then added to 1 l of water. The product precipitated in this way was filtered off, washed first with water and then with chloroform, and dried, then acidified with 13% by weight hydrochloric acid, washed again with water and dried, and finally purified by a Soxhlett extraction with methanol.

5.1 g of I16 were obtained in the form of a blue solid, which corresponds to a yield of 25%.

Analytical Data of I16:

UV-Vis (CHCl$_3$): $\lambda_{max}$ (ϵ)=658 (89 000), 600 (45 000) nm (M$^{-1}$ cm$^{-1}$);

MS (FD): m/z (rel. int.)=795.2 (100%) [M$^+$].

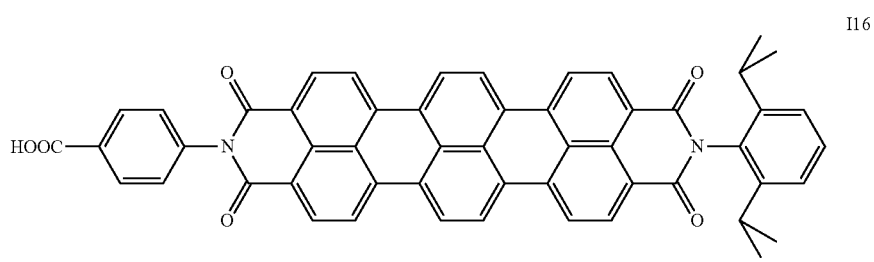 [SMILES: CC(C)c1cccc(C(C)C)c1N1C(=O)c2ccc3c4ccc5c6ccc7c8c(ccc(c9ccc(c%10ccc(c2c3%10)C1=O)c4c59)c86)C(=O)N(c1ccc(C(=O)O)cc1)C7=O]

I16

Example 17

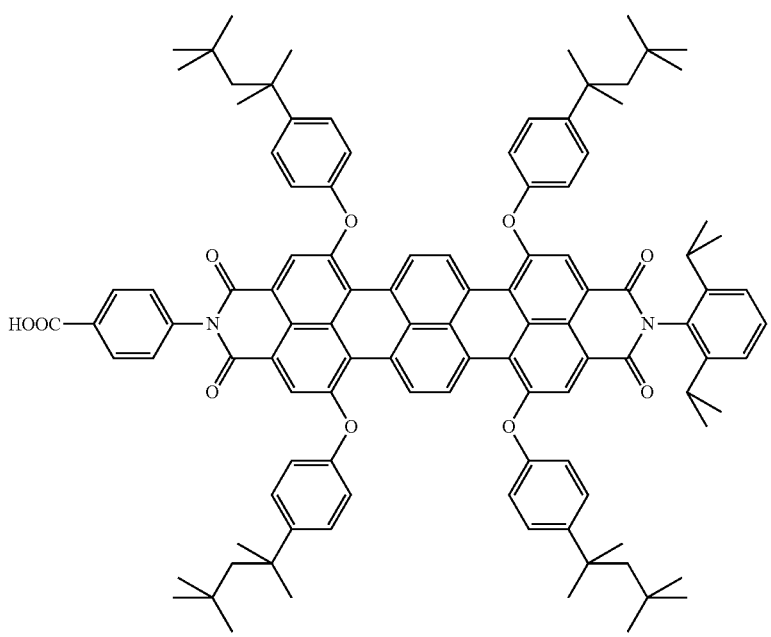

To prepare the rylene derivative I17, the rylene derivative I15 unsubstituted in the rylene skeleton was first converted by reacting with bromine to the tetrabromo derivative (step a) which was then reacted with 4-(tert-octyl)phenol to give the rylene derivative I17 (step b).

Step a):

A mixture of 2.0 g (2.5 mmol) of I15 in 26 ml of chloroform was heated to 60° C. and stirred at this temperature for 10 min. After cooling to 40° C., first 52 ml of water and then 12.8 g (80.0 mmol) of bromine were added. The mixture was then stirred at 40° C. for 10 h. The course of reaction was monitored by thin layer chromatography (eluent: 3:1 methylene chloride/acetone).

After cooling to room temperature and removal of the excess bromine with nitrogen, the reaction mixture was stirred further after addition of an aqueous solution of sodium disulfite and methylene chloride. The organic phase removed was dried with magnesium sulfate, then the solvent was removed under reduced pressure.

2.4 g of 1,6,9,14-tetrabrominated rylene derivative I15 were obtained, which corresponds to a yield of 88%.

Analytical Data:

MS (FD): m/z (rel. int.)=1110.7 (100%) [M$^+$].

Step b):

A mixture of 3.0 g (2.7 mmol) of 1,6,9,14-tetrabrominated rylene derivative I15 and 200 ml of anhydrous N-methylpyrrolidone was purged with nitrogen, then 4.7 g (23.0 mmol) of tert-octylphenol and 2.3 g (17.0 mmol) of potassium carbonate were added. The mixture was then heated to 80° C. and stirred at this temperature for 16 h.

After cooling to room temperature, the product was precipitated by adding 100 ml of dilute hydrochloric acid, filtered off, washed to neutrality with water and dried.

2.0 g of I17 were obtained in the form of a blue solid, which corresponds to a yield of 46%.

Analytical Data of I17:
UV-Vis (C$_2$H$_5$OH): $\lambda_{max}$=670 nm;
MS (FD): m/z (rel. int.)=1612.3 (100%) [M$^+$].

Example 18

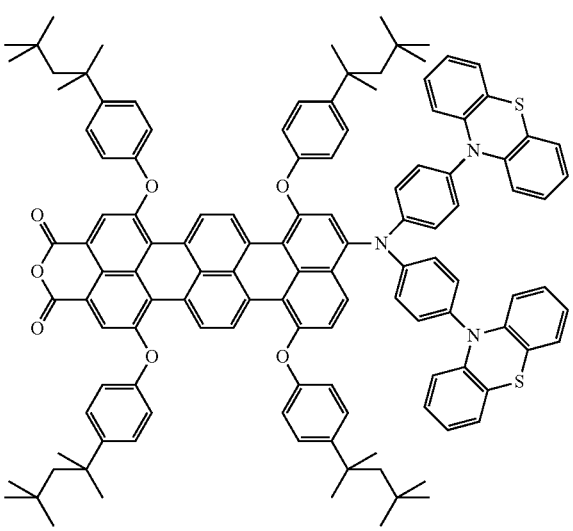

The rylene derivative I18 was prepared proceeding from N-(2,6-diisopropylphenyl)-1,6,9,14-tetra[(4-tert-octyl)phenoxy]-11-bromot-errylene-3,4-dicarboximide, which was first converted, under bromine exchange with bis(4-(phenothiazinyl)phenyl)amine, to the amino-substituted dicarboximide (step a), which was subsequently hydrolyzed under alkaline conditions to the dicarboxylic anhydride I18 (step b).

Step a):

A mixture of 0.20 g (0.13 mmol) of N-(2,6-diisopropylphenyl)-1,6,9,14-tetra[(4-tert-octyl)phenoxy]-11-bromot-errylene-3,4-dicarboximide, 0.147 g (0.26 mmol) of bis(4-(phenothiazinyl)phenyl)amine, 0.007 g (0.007 mmol) of tris(dibenzylideneacetone)dipalladium(0), 0.132 g (0.065 mmol) of tris(tert-butyl)phosphine (10% solution/toluene), 0.016 g (0.13 mmol) of potassium tert-butoxide and 10 ml of dry toluene was heated to 75° C. under nitrogen and stirred at this temperature for 19 h.

After the solvent had been distilled off, the crude product was subjected to column chromatography on silica gel with a hexane/ethyl acetate mixture (10:1) as the eluent. 0.04 g of N-(2,6-diisopropylphenyl)-1,6,9,14-tetra[(4-tert-octyl)phenoxy]-9-[bis(4-(phenothiazinyl)phenyl)aminoterrylene-3,4-dicarboximide was obtained in the form of a blue solid, which corresponds to a yield of 16% (taking only the cleanest fractions).

Analytical Data:

UV-Vis (CH$_2$Cl$_2$): $\lambda_{max}$=654 nm;

MS (FD): m/z (rel. int.)=1982.9 (100%) [M$^+$].

Step b):

A mixture of 0.04 g (0.02 mmol) of N-(2,6-diisopropylphenyl)-1,6,9,14-tetra[(4-tert-octyl)phenoxy]-9-[bis(4-(phenothiazinyl)phenyl)aminoterrylene-3,4-dicarboximide and 8 ml of 2-methyl-2-butanol was heated to 60° C. After 0.5 h, 0.034 g (0.6 mmol) of potassium hydroxide and 0.035 g (0.60 mmol) of potassium fluoride were added. The mixture was then heated to gentle reflux (about 118° C.) and stirred at this temperature for 17 h.

After cooling to 40° C., acidifying with 50% by weight acetic acid and stirring at 40° C. for a further one hour, the reaction product was precipitated in water, filtered off and washed with hot water, and the residue was resuspended in hot water, acidified with 50% acetic acid, boiled at reflux for 2 h, filtered off, washed with hot water and dried. Thereafter, the crude product was subjected to column chromatography on silica gel with dichloromethane as the eluent.

0.033 g of I18 was obtained in the form of a blue-green solid, which corresponds to a yield of 90%.

Analytical Data of I18:

MS (FD): m/z (rel. int.)=1823.7 (100%) [M$^+$].

Example 19

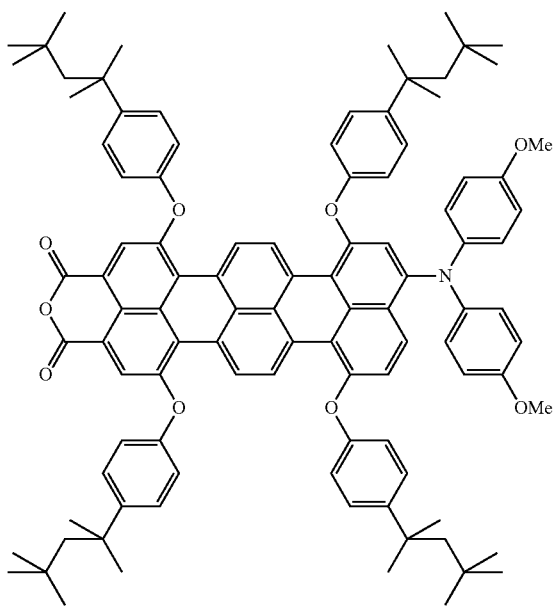

I19

The rylene derivative I19 was prepared proceeding from N-(2,6-diisopropylphenyl)-1,6,9,14-tetra[(4-tert-octyl)phenoxy]-11-bromot-errylene-3,4-dicarboximide, which was first converted, under bromine exchange with bis[(4-methoxy)phenyl]amine, to the amino-substituted dicarboximide (step a), which was subsequently hydrolyzed under alkaline conditions to the dicarboxylic anhydride I19 (step b).

Step a):

A mixture of 0.090 g (0.06 mmol) of N-(2,6-diisopropylphenyl)-1,6,9,14-tetra[(4-tert-octyl)phenoxy]-11-bromot-errylene-3,4-dicarboximide, 0.028 g (0.12 mmol) of bis(4-methoxy)phenylamine, 0.003 g (0.003 mmol) of tris(dibenzylideneacetone)dipalladium(0), 0.06 g (0.03 mmol) of tris(tert-butyl)phosphine (10% solution/toluene), 0.006 g (0.6 mmol) of sodium tert-butoxide and 5 ml of dry toluene was heated to 70° C. under nitrogen and stirred at this temperature for 20 h.

After the solvent had been distilled off, the crude product was subjected to column chromatography on silica gel with a toluene/hexane mixture (2:1) as the eluent.

0.115 g of N-(2,6-diisopropylphenyl)-1,6,9,14-tetra[(4-tert-octyl)phenoxy]-9-[bis(4-(methoxy)phenyl)aminoterrylene-3,4-dicarboximide was obtained in the form of a blue solid, which corresponds to a yield of 16%.

Analytical Data:

UV-Vis (CH$_2$Cl$_2$): $\lambda_{max}$=678 nm;

MS (FD): m/z (rel. int.)=1649.1 (100%) [M$^+$].

Step b):

A mixture of 0.105 g (0.064 mmol) of N-(2,6-diisopropylphenyl)-1,6,9,14-tetra[(4-tert-octyl)phenoxy]-9-[bis(4-(methoxy)phenyl)aminoterrylene-3,4-dicarboximide and 20 ml of 2-methyl-2-butanol was heated to 60° C. After 0.5 h, 0.108 g (1.92 mmol) of potassium hydroxide and 0.112 g (1.92 mmol) of potassium fluoride were added. The mixture was then heated to gentle reflux (about 118° C.) and stirred at this temperature for 17 h.

After cooling to 40° C., acidifying with 50% by weight acetic acid and further stirring at 40° C. for one hour, the reaction product was precipitated in water, filtered off and washed with hot water/methanol, and the residue was resuspended in water, acidified with 50% acetic acid, boiled at reflux for 2 h, filtered off and washed with hot water and dried. Thereafter, the crude product was subjected to column chromatography on silica gel with a toluene/glacial acetic acid mixture (97:3) as the eluent. The product was then neutralized.

0.050 g of I19 was obtained in the form of a blue-green solid, which corresponds to a yield of 90%.

Analytical Data of I19:

UV-Vis (CH$_2$Cl$_2$): $\lambda_{max}$=684 nm;

MS (FD): m/z (rel. int.)=1489.9 (100%) [M$^+$].

Example 20

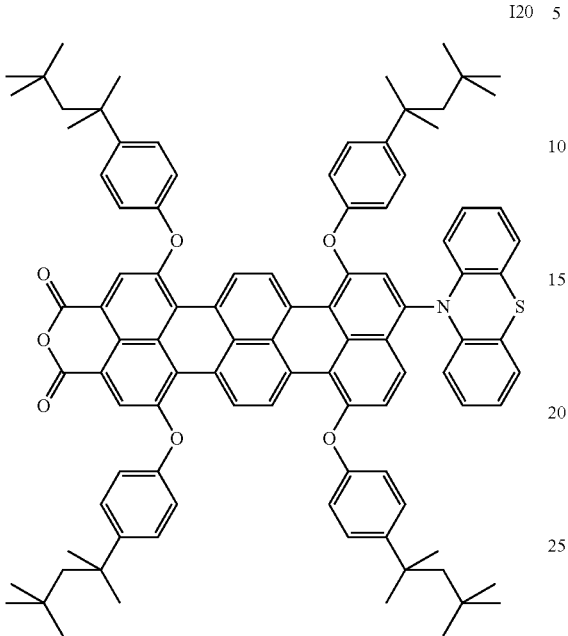 [SMILES: COc1ccc(N(c2ccc(OC)cc2)c2cc(Oc3ccc(C(C)(C)CC(C)(C)C)cc3)c3c4ccc5c6c(Oc7ccc(C(C)(C)CC(C)(C)C)cc7)cc7c8c(cc(Oc9ccc(C(C)(C)CC(C)(C)C)cc9)c(c9ccc(c%10c(Oc%11ccc(C(C)(C)CC(C)(C)C)cc%11)ccc2c%103)c4c95)c86)C(=O)OC7=O)cc1]

The rylene derivative I20 was prepared proceeding from N-(2,6-diisopropylphenyl)-1,6,9,14-tetra[(4-tert-octyl)phenoxy]-11-bromoterrylene-3,4-dicarboximide, which was first converted, under bromine exchange with phenothiazine, to the phenothiazinyl-substituted dicarboximide (step a), which was subsequently hydrolyzed under alkaline conditions to the dicarboxylic anhydride I20 (step b).

Step a):

A mixture of 0.20 g (0.13 mmol) of N-(2,6-diisopropylphenyl)-1,6,9,14-tetra[(4-tert-octyl)phenoxy]-11-bromoterrylene-3,4-dicarboximide, 0.053 g (0.26 mmol) of phenothiazine, 0.007 g (0.007 mmol) of tris(dibenzylideneacetone)dipalladium(0), 0.132 g (0.065 mmol) of tris(tert-butyl)phosphine (10% solution/toluene), 0.016 g (0.13 mmol) of potassium tert-butoxide and 10 ml of dry toluene was heated to 90° C. under nitrogen and stirred at this temperature for 22 h.

After the solvent had been distilled off, the crude product was subjected to column chromatography on silica gel with a hexane/ethyl acetate mixture (15:1) as the eluent.

0.125 g of N-(2,6-diisopropylphenyl)-1,6,9,14-tetra[(4-tert-octyl)phenoxy]-9-phenothiazinylterrylene-3,4-dicarboximide was obtained in the form of a blue solid, which corresponds to a yield of 59%.

Analytical Data:
MS (FD): m/z (rel. int.)=1618.8 (100%) [M+].

Step b):

A mixture of 0.070 g (0.043 mmol) of N-(2,6-diisopropylphenyl)-1,6,9,14-tetra[(4-tert-octyl)phenoxy]-9-[bis(4-(methoxy)phenypaminoterrylene-3,4-dicarboximide and 13 ml of 2-methyl-2-butanol was heated to 60° C. After 0.5 h, 0.075 g (1.29 mmol) of potassium hydroxide and 0.073 g (1.29 mmol) of potassium fluoride were added. The mixture was then heated to gentle reflux (about 118° C.) and stirred at this temperature for 16 h.

After cooling to 40° C., acidifying with 50% by weight acetic acid and stirring at 40° C. for a further hour, the reaction product was precipitated in water, filtered off and washed with water/methanol, and the residue was resuspended in water, acidified with 50% acetic acid, boiled at reflux for 2 h, filtered off, washed with hot water and dried. Thereafter, the crude product was subjected to column chromatography on silica gel with a dichloromethane/hexane/glacial acetic acid mixture (47.5:47.5:5) as the eluent. The product was then neutralized.

0.040 g of I20 was obtained in the form of a blue solid, which corresponds to a yield of 60%.

Analytical Data of I20:
UV-Vis (CH$_2$Cl$_2$): $\lambda_{max}$=646 nm;
MS (FD): m/z (rel. int.)=1459.5 (100%) [M+].

Example 21

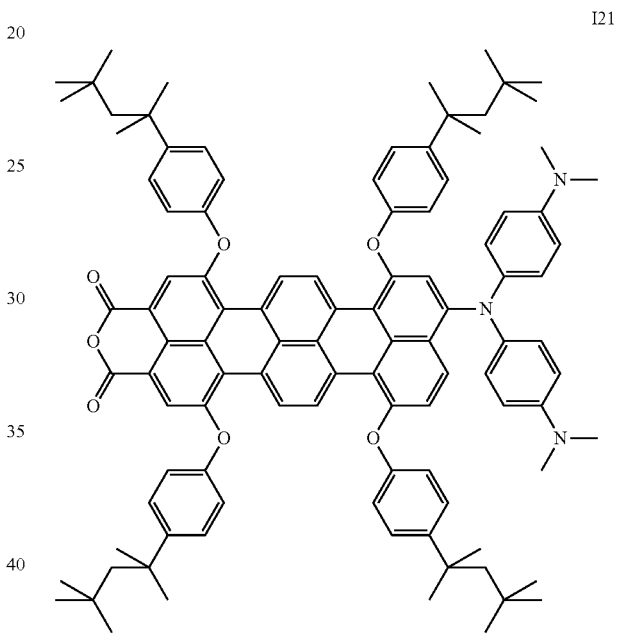

The rylene derivative I21 was prepared proceeding from N-(2,6-diisopropylphenyl)-1,6,9,14-tetra[(4-tert-octyl)phenoxy]-11-bromoterrylene-3,4-dicarboximide, which was converted first, under bromine exchange with bis[(4-dimethylamino)phenyl]amine, to the amino-substituted dicarboximide (step a), which was subsequently hydrolyzed under alkaline conditions to the dicarboxylic anhydride I21 (step b).

Step a):

A mixture of 0.400 g (0.27 mmol) of N-(2,6-diisopropylphenyl)-1,6,9,14-tetra[(4-tert-octyl)phenoxy]-11-bromoterrylene-3,4-dicarboximide, 0.141 g (0.54 mmol) of 1,4-benzenediamine, N'-(4-(dimethylamino)phenyl)-N,N-dimethyl, 0.013 g (0.014 mmol) of tris(dibenzylideneacetone)dipalladium(0), 0.273 g (0.135 mmol) of tris(tert-butyl)phosphine (10% solution/toluene), 0.026 g (0.27 mmol) of sodium tert-butoxide and 20 ml of dry toluene was heated to 80° C. under nitrogen and stirred at this temperature for 13 h.

After the solvent had been distilled off, the crude product was subjected to column chromatography on silica gel with dichloromethane as the eluent.

0.280 g of a blue-green solid was obtained, which corresponds to a yield of 62%.

Analytical Data:

MS (FD): m/z (rel. int.)=1675.0 (100%) [M+].

Step b):

A mixture of 0.195 g (0.12 mmol) of N-(2,6-diisopropylphenyl)-1,6,9,14-tetra[(4-tert-octyl)phenoxy]-9-[bis(4-(methoxy)phenyl)aminoterrylene-3,4-dicarboximide and 36 ml of 2-methyl-2-butanol was heated to 60° C. After 0.5 h, 0.213 g (3.60 mmol) of potassium hydroxide and 0.209 g (3.60 mmol) of potassium fluoride were added. The mixture was then heated to gentle reflux (about 118° C.) and stirred at this temperature for 13 h.

After cooling to 40° C., acidifying with 50% by weight acetic acid and further stirring at 40° C. for one hour, the reaction product was precipitated in water, filtered off and washed with water/methanol, and the residue was resuspended in water, acidified with 50% acetic acid, boiled at reflux for 2 h, filtered off, washed with hot water and dried. Thereafter, the crude product was subjected to column chromatography on silica gel with a dichloromethane/acetic acid mixture (95:5) as the eluent. The product was then neutralized.

0.018 g of I21 was obtained in the form of a green-blue solid, which corresponds to a yield of 10%.

Analytical Data of I21:

UV-Vis (CH$_2$Cl$_2$): $\lambda_{max}$=682 nm;

MS (FD): m/z (rel. int.)=1515.7 (100%) [M+].

Analytical Data of I11:

Example 22

I22

The rylene derivative I22 was prepared proceeding from N-(2,6-diisopropylphenyl)-9-bromoperylene-3,4-dicarboximide, which was converted first, under bromine exchange with bis-[4-(5'-hexyl-[2,2']bithiophenyl-5-yl)phenyl]amine, to the amino-substituted dicarboximide (step a), which was subsequently hydrolyzed under alkaline conditions to the dicarboxylic anhydride I11 (step b).

Step a):

Buchwald Reaction (General)

A mixture of 9-bromoperylene derivative (1 eq.), amine (1.1-1.5 eq.), tris(dibenzylideneacetone)dipalladium(0) (2 mol %), tris(tert-butyl)phosphine (3 mol %) and sodium tert-butoxide (1.5 eq.) in dry toluene was heated to 80° C. under argon and stirred at this temperature for 1 d.

After the solvent had been distilled off, the crude product was subjected to column chromatography on silica gel.

450 mg of the peryleneamine derivative were obtained in the form of a green solid, which corresponds to a yield of 55%.

Step b):

Hydrolysis (General)

A mixture of perylenemonoimide (product of step a), potassium hydroxide (300-500 eq.) and isopropanol was heated to reflux temperature (about 82° C.) for 16 h.

After cooling to room temperature, the reaction mixture was added to acetic acid, heated to 40° C. and stirred at this temperature for 4 h. The acetic acid was distilled off and the product was washed to neutrality with water, dried and subjected to column chromatography on silica gel.

I22 was not subjected to column chromatography, and the product was instead dissolved in THF and precipitated twice in ethanol.

150 mg of I22 were obtained in the form of a blue solid, which corresponds to a yield of 45%.

Analytical Data:

UV-Vis (CH$_2$Cl$_2$): $\lambda_{max}$ ($\epsilon$)=398 (40 400), 602 (14 900) nm (M$^{-1}$ cm$^{-1}$);

MS (FD): m/z (rel. int.)=985.2 (100%) [M+].

Step b):

Example 23

I23

The rylene derivative I23 was prepared proceeding from N-(2,6-diisopropylphenyl)-1,6,9-tribromoperylene-3,4-dicarboximide, which was converted first, under bromine exchange with bis[(4-tert-octyl)phenyl]amine, to the trisamino-substituted dicarboximide (step a), which was subsequently hydrolyzed under alkaline conditions to the dicarboxylic anhydride I23 (step b).

Step a):

A mixture of 0.8 g (1.1 mmol) of N-(2,6-diisopropylphenyl)-1,6,9-tribromoperylene-3,4-dicarboximide, 2.6 g (6.6 mmol) of bis[(4-tert-octyl)phenyl]amine, 160 mg (0.14 mmol) of tris(dibenzylideneacetone)dipalladium(0), 40 mg (0.16 mmol) of tris(tert-butyl)phosphine, 160 mg (0.18 mmol) of sodium tert-butoxide and 100 ml of dry toluene was heated to 80° C. under argon and stirred at this temperature for 2 d.

After the solvent had been distilled off, the crude product was subjected to column chromatography on silica gel with toluene as the eluent.

0.20 mg of the peryleneimide was obtained in the form of a blue solid, which corresponds to a yield of 10%.

Analytical Data:
UV-Vis (CH$_2$Cl$_2$): $\lambda_{max}$ ($\epsilon$)=681 (19 000) nm (M$^{-1}$ cm$^{-1}$);

Step b):
Hydrolysis analogous to example 22 (step b).

20 mg of I23 were obtained in the form of a violet solid, which corresponds to a yield of 10%.

Analytical Data of I23:
UV-Vis (CH$_2$Cl$_2$): $\lambda_{max}$ ($\epsilon$)=698 (13 000) nm (M$^{-1}$ cm$^{-1}$);
MS (FD): m/z (rel. int.)=1494.1 (100%) [M$^+$].

Example 24

I24

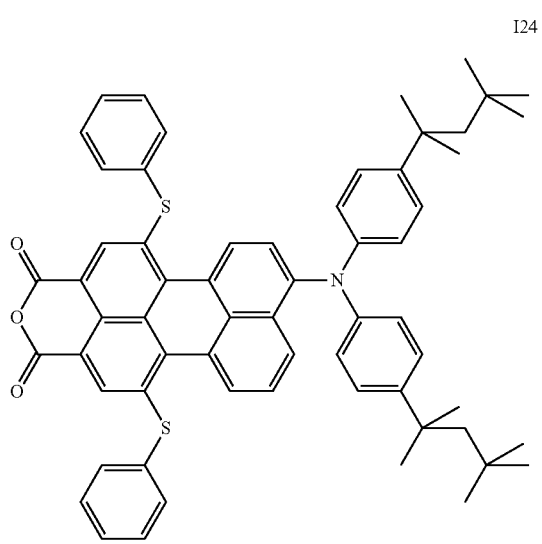 [SMILES: CC(C)(C)CC(C)(C)c1ccc(N(c2ccc(C(C)(C)CC(C)(C)C)cc2)c2ccc3c4c(Sc5ccccc5)cc5c6c(cc(Sc7ccccc7)c(c7cccc2c73)c64)C(=O)OC5=O)cc1]

The rylene derivative I24 was prepared proceeding from N-(2,6-diisopropylphenyl)-1,6,9-tribromoperylene-3,4-dicarboximide, which was first converted, under bromine exchange with thiophenol, to N-(2,6-diisopropylphenyl)-1,6-thiophenyl]-9-bromoperylene-3,4-dicarboximide (step a), which was then subjected to a further bromine exchange with bis[(4-tert-octyl)phenyl]amine to give N-(2,6-diisopropylphenyl)-9-(bis-p-t-octylphenyl)amino-1,6-dithiophenylperylene-3,4-dicarboximide (step b), which was subsequently hydrolyzed under alkaline conditions to the dicarboxylic anhydride I24 (step c).

Step a):
A mixture of 1.0 g (1.99 mmol) of N-(2,6-diisopropylphenyl)-1,6,9-tribromoperylene-3,4-dicarboximide, 0.229 g (1.39 mmol) of thiophenol, and 0.256 g (2.78 mmol) of potassium hydroxide and 80 ml of NMP was heated to 80° C. under argon and stirred at this temperature for 3 h.

After cooling, the product was added to 25% by weight hydrochloric acid. The product precipitated in this way was filtered off, washed with water, dried and subjected to column chromatography on silica gel with a methylene chloride eluent.

600 mg of N-(2,6-diisopropylphenyl)-1,6-thiophenyl]-9-bromoperylene-3,4-dicarboximide were obtained in the form of a red solid, which corresponds to a yield of 56%.

Step b):
Buchwald Analogous to Example 22 (Step a)
After the solvent had been distilled off, the crude product was subjected to column chromatography on silica gel with toluene as the eluent.

350 mg of N-(2,6-diisopropylphenyl)-9-(bis-p-t-octylphenyl)amino-1,6-dithiophenylperylene-3,4-dicarboximide were obtained in the form of a blue solid, which corresponds to a yield of 84%.

Analytical Data:
UV-Vis (CH$_2$Cl$_2$): $\lambda_{max}$ ($\epsilon$)=606 (13 898), 462 (7690) (M$^{-1}$ cm$^{-1}$);
MS (FD): m/z (rel. int.)=929.5

Step c):
Hydrolysis Analogous to Example 22 (Step b)
To a column chromatography on silica gel with a toluene as the eluent was subjected.

150 mg of I24 were obtained in the form of a blue solid, which corresponds to a yield of 59%.

Analytical Data:
UV-Vis (CH$_2$Cl$_2$): $\lambda_{max}$ ($\epsilon$)=620 (22 800), 462 (13 700) nm (M$^{-1}$ cm$^{-1}$);
MS (FD): m/z (rel. int.)=929.5 (100%) [M$^+$].

Example 25

I25

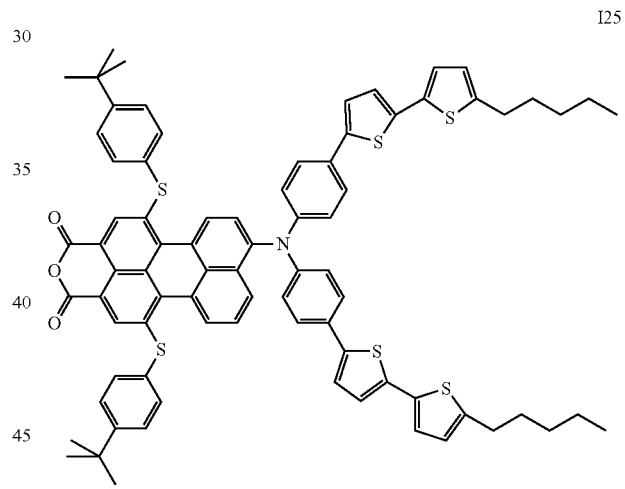

The rylene derivative I25 was prepared proceeding from N-(2,6-diisopropylphenyl)-1,6,9-tribromoperylene-3,4-dicarboximide, which was first converted, under bromine exchange with tert-butylthiophenol, to N-(2,6-diisopropylphenyl)-1,6-p-tert-butylthiophenyl]-9-bromoperylene-3,4-dicarboximide (step a), which was then subjected to a further bromine exchange with bis[4-(5'-hexyl-[2,2']bithiophenyl-5-yl)phenyl]amine N-(2,6-diisopropylphenyl)-1,6-di-p-tert-butylthiophenyl-9-bis[4-(5'-hexyl-[2,2']bithiophenyl-5-yl)phenyl]aminoperylene-3,4-dicarboximide (step b), which was subsequently hydrolyzed under alkaline conditions to the dicarboxylic anhydride I25 (step c).

Step a):
A mixture of 5.0 g (6.96 mmol) of N-(2,6-diisopropylphenyl)-1,6,9-tribromoperylene-3,4-dicarboximide, 1.16 g (6.96 mmol) of tert-butylthiophenol and 0.96 g (6.99 mmol) of potassium hydroxide and 80 ml of NMP was heated to 50° C. and stirred at this temperature for 1.5 h. Thereafter, another 0.58 g (3.48 mmol) of tert-butylthiophenol and 0.48 g (3.48 mmol) of potassium hydroxide were added, and the mixture was stirred at this temperature for a further 1.5 h.

After cooling, the product was added to 25% by weight hydrochloric acid. The product precipitated in this way was filtered off, washed with water, dried and subjected to column chromatography on silica gel with toluene as the eluent. 3.0 g of N-(2,6-diisopropylphenyl)-1,6-p-tert-butylthiophenyl]-9-bromoperylene-3,4-dicarboximide were obtained in the form of a red solid, which corresponds to a yield of 48%.

MS (FD): m/z (rel. int.)=888.6 (100%) [M$^+$].

Step b):

Buchwald Analogous to Example 22 (Step a)

After distilling off the solvent, the crude product was subjected to column chromatography on silica gel with toluene as the eluent.

500 mg of N-(2,6-diisopropylphenyl)-1,6-di-p-tert-butylthiophenyl-9-bis[4-(5'-hexyl-1-[2,2']bithiophenyl-5-yl) phenyl]aminoperylene-3,4-dicarboximide were obtained in the form of a green solid, which corresponds to a yield of 75%.

Step c):

Hydrolysis Analogous to Example 22 (Step b)

To a column chromatography on silica gel with toluene as the eluent was subjected. 200 mg of I25 were obtained in the form of a blue solid, which corresponds to a yield of 57%.

Analytical Data:

UV-Vis (CH$_2$Cl$_2$): $\lambda_{max}$ ($\epsilon$)=602 (19 200) nm (M$^{-1}$ cm$^{-1}$); MS (FD): m/z (rel. int.)=1316.3 (100%) [M$^+$].

Example 26

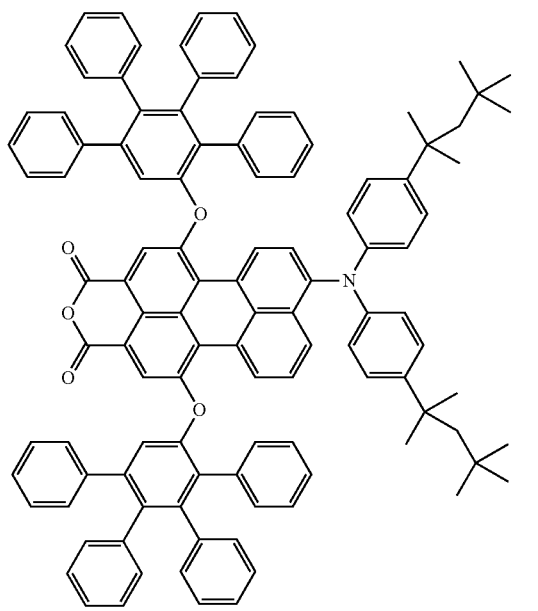

I26

The rylene derivative I26 was prepared proceeding from N-(2,6-diisopropylphenyl)-1,6,9-tribromoperylene-3,4-dicarboximide under similar conditions to those in 125. The description of how the tetraphenylphenyl-substituted perylene derivative is prepared can be found in Qu et al, Chem. Eur. J. 2004, 10, 528-537.

Step a):

Buchwald Analogous to Example 22 (Step a)

After the solvent had been distilled off, the crude product was subjected to column chromatography on silica gel with dichloromethane as the eluent.

500 mg of N-(2,6-diisopropylphenyl)-9-(bis-p-tert-octylphenyl)amino-1,6-di(2,3,4,5-tetraphenylphenoxy) perylene-3,4-dicarboximide were obtained in the form of a blue solid, which corresponds to a yield of 80%.

Analytical Data:

MS (FD): m/z (rel. int.)=1656.5 (100%) [M$^+$].

Step b):

Hydrolysis Analogous to Example 22 (Step b)

To a column chromatography on silica gel with dichloromethane as the eluent was subjected.

120 mg of I26 were obtained in the form of a blue solid, which corresponds to a yield of 66%.

Analytical Data of I26:

UV-Vis (CH$_2$Cl$_2$): $\lambda_{max}$=603, 486 nm.

Example 27

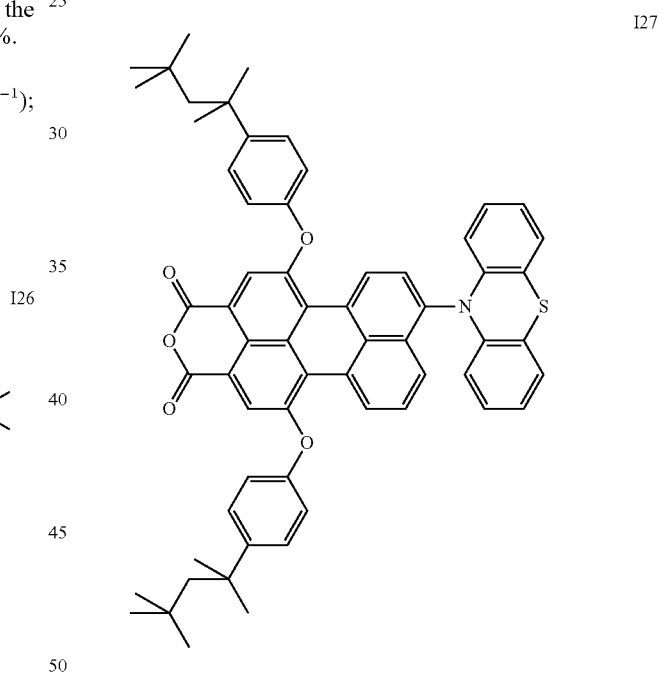

I27

The rylene derivative I27 was prepared proceeding from N-(2,6-diisopropylphenyl)-1,6-bis[(4-tert-octyl)phenoxy]-9-bromoperylene-3,4-dicarboximide, which was first converted, under bromine exchange with phenothiazine, to the substituted dicarboximide (step a), which was subsequently hydrolyzed under alkaline conditions to the dicarboxylic anhydride I27 (step b).

Step a):

Buchwald Analogous to Example 22 (Step a)

After the solvent had been distilled off, the crude product was subjected to column chromatography on silica gel with toluene as the eluent.

330 mg of (2,6-diisopropylphenyl)-9-phenothiazine-1,6-di(p-tert-octylphenoxy)perylene-3,4-dicarboximide were obtained in the form of a brown solid, which corresponds to a yield of 95%.

Analytical Data:

UV-Vis (CH$_2$Cl$_2$): $\lambda_{max}$ ($\epsilon$)=516 (24 000) nm (M$^{-1}$ cm$^{-1}$);

Step b):

Hydrolysis Analogous to Example 22 (Step b)

To a column chromatography on silica gel with toluene as the eluent was subjected.

40 mg of I27 were obtained in the form of a brown solid, which corresponds to a yield of 15%.

Analytical Data:

UV-Vis (CH$_2$Cl$_2$): $\lambda_{max}$ ($\epsilon$)=518 (22 000) nm (M$^{-1}$ cm$^{-1}$);

Example 28

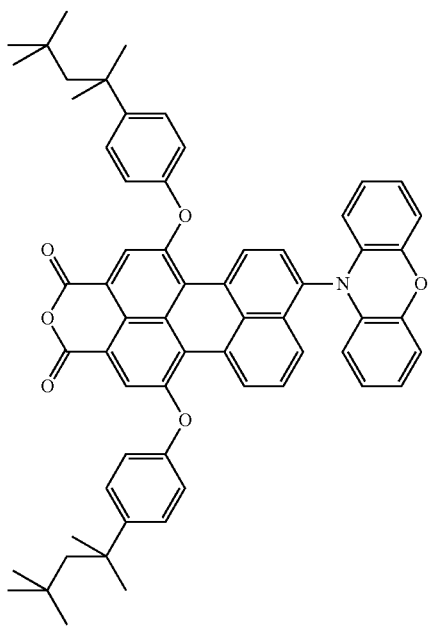

I28

The rylene derivative I28 was prepared proceeding from N-(2,6-diisopropylphenyl)-1,6-bis[(4-tert-octyl)phenoxy]-9-bromoperylene-3,4-dicarboximide, which was converted first, under bromine exchange with phenoxazine, to the substituted dicarboximide (step a), which was subsequently hydrolyzed under alkaline conditions to the dicarboxylic anhydride I28 (step b).

Step a):

Buchwald Analogous to Example 22 (Step a)

After the solvent had been distilled off, the crude product was subjected to column chromatography on silica gel with toluene as the eluent.

300 mg of N-(2,6-diisopropylphenyl)-9-phenoxazine-1,6-di(p-tert-octylphenoxy)perylene-3,4-dicarboximide were obtained in the form of a brown solid, which corresponds to a yield of 90%.

Analytical Data:

UV-Vis (CH$_2$Cl$_2$): $\lambda_{max}$ ($\epsilon$)=513 (24 000) nm (M$^{-1}$ cm$^{-1}$);

Step b):

Hydrolysis Analogous to Example 22 (Step b)

To a column chromatography on silica gel with toluene as the eluent was subjected.

50 mg of I28 were obtained in the form of a brown solid, which corresponds to a yield of 20%.

Analytical Data:

UV-Vis (CH$_2$Cl$_2$): $\lambda_{max}$ ($\epsilon$)=514 (14 000) nm (M$^{-1}$ cm$^{-1}$);

Example 29

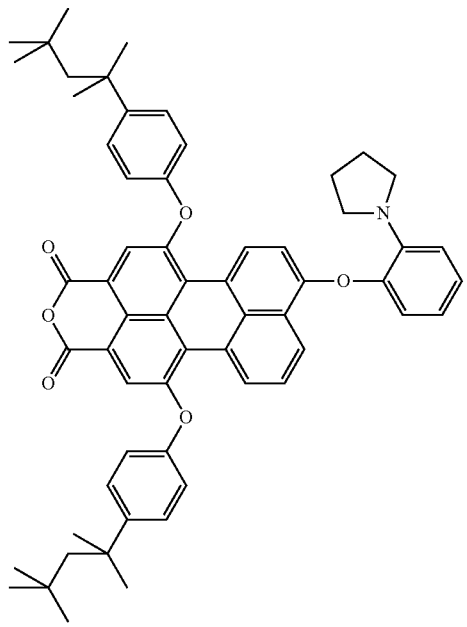

I29

The rylene derivative I29 was prepared proceeding from N-(2,6-diisopropylphenyl)-1,6-bis[(4-tert-octyl)phenoxy]-9-bromoperylene-3,4-dicarboximide, which was converted first, under bromine exchange with o-pyrrolidonophenol, to the substituted dicarboximide (step a), which was subsequently hydrolyzed under alkaline conditions to the dicarboxylic anhydride I29 (step b).

Step a):

A mixture of 0.3 g (0.31 mmol) of N-(2,6-diisopropylphenyl)-1,6,9-tribromoperylene-3,4-dicarboximide, 0.076 g (0.46 mmol) of o-pyrrolidinophenol and 0.043 g (0.31 mmol) of potassium hydroxide and 80 ml of NMP was heated to 80° C. under argon and stirred at this temperature for 12 h.

After cooling, the product was added to 25% by weight hydrochloric acid. The product precipitated in this way was filtered off, washed with water, dried and subjected to column chromatography on silica gel with a methylene chloride/pentane mixture (1:2) as the eluent.

150 mg of N-(2,6-diisopropylphenyl)-1,6-bis[4-(1,1,3,3-tetramethylbutyl)phenoxy]-9-(p-pyrrolidino)phenoxyperylene-3,4-dicarboximide were obtained in the form of a red solid, which corresponds to a yield of 92%.

UV-Vis (CH$_2$Cl$_2$): $\lambda_{max}$=541 nm.

Step b):

Hydrolysis Analogous to Example 22 (Step b)

To a column chromatography on silica gel with a methylene chloride/pentane mixture (1:2) as the eluent was subjected.

35 mg of I29 were obtained in the form of a violet solid, which corresponds to a yield of 20%.

Analytical Data:
UV-Vis (CH$_2$Cl$_2$): $\lambda_{max}$=548;
MS (FD): m/z (rel. int.)=892.4 (100%) [M$^+$].

Example 30

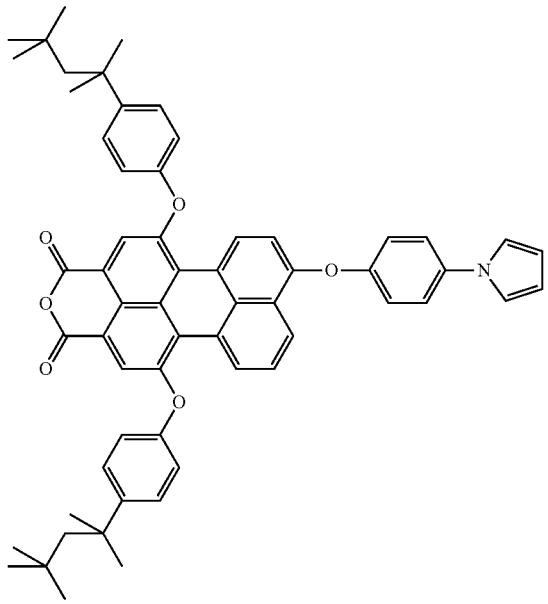

I30

The rylene derivative I30 was prepared proceeding from N-(2,6-diisopropylphenyl)-1,6-bis[(4-tert-octyl)phenoxy]-9-bromoperylene-3,4-dicarboximide, which was first converted, under bromine exchange with p-pyrrolylphenol, to the substituted dicarboximide (step a), which was subsequently hydrolyzed under alkaline conditions to the dicarboxylic anhydride I30 (step b).

Step a):

A mixture of 0.3 g (0.31 mmol) of N-(2,6-diisopropylphenyl)-1,6,9-tribromoperylene-3,4-dicarboximide, 0.074 g (0.46 mmol) of o-pyrrolidinophenol and 0.070 g (0.46 mmol) of potassium hydroxide and 80 ml of NMP was heated to 80° C. under argon and stirred at this temperature for 12 h.

After cooling, the product was added to 25% by weight hydrochloric acid. The product precipitated in this way was filtered off, washed with water, dried and subjected to column chromatography on silica gel with a methylene chloride/pentane mixture (1:2) as the eluent.

300 mg of N-(2,6-diisopropylphenyl)-1,6-bis[4-(1,1,3,3-tetramethylbutyl)phenoxy]-9-(p-pyrrolyl)phenoxyperylene-3,4-dicarboximide were obtained in the form of a red solid, which corresponds to a yield of 92%.

UV-Vis (CH$_2$Cl$_2$): $\lambda_{max}$=536, 415 nm.

Step b):

Hydrolysis Analogous to Example 22 (Step b)

To a column chromatography on silica gel with a methylene chloride/pentane mixture (1:2) as the eluent was subjected.

50 mg of I30 were obtained in the form of a violet solid, which corresponds to a yield of 15%.

Analytical Data:
UV-Vis (CH$_2$Cl$_2$): $\lambda_{max}$=536;
MS (FD): m/z (rel. int.)=866.6 (100%) [M$^+$].

Example 31

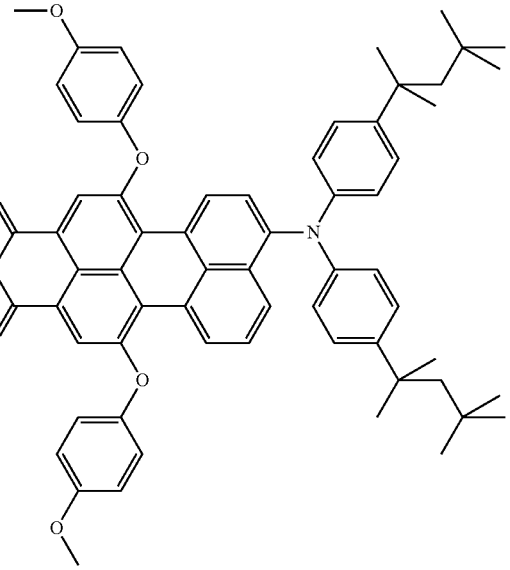

I31

The rylene derivative I31 was prepared proceeding from N-(2,6-diisopropylphenyl)-1,6,9-tribromoperylene-3,4-dicarboximide, which was first converted, under bromine exchange with 4-methoxyphenol, to N-(2,6-diisopropylphenyl)-1,6-bis[phenoxy]-9-bromoperylene-3,4-dicarboximide (step a), which was then converted a further bromine exchange with bis[(4-tert-octyl)phenyl]amine to the amine derivative (step b), which was then hydrolyzed under alkaline conditions to the dicarboxylic anhydride I31 (step c).

Step a):

Phenoxylation Reaction (General)

A mixture of N-(2,6-diisopropylphenyl)-1,6,9-tribromoperylene-3,4-dicarboximide (1 eq.), phenol derivative (1 eq.), potassium hydroxide (1 eq.) was dissolved in NMP, heated to 80° C. and stirred at this temperature for 1.5 h. Thereafter, more phenol derivative (1 eq.) and potassium hydroxide (1 eq.) were added, and the mixture was stirred at this temperature for a further 2 h.

After cooling, the product was added to 25% by weight hydrochloric acid. The product precipitated in this way was filtered off, washed with water, dried and subjected to column chromatography on silica gel.

640 mg of N-(2,6-diisopropylphenyl)-1,6-diphenoxy-9-bromoperylene-3,4-dicarboximide were obtained in the form of a red solid, which corresponds to a yield of 55%.

Step b):

Buchwald Analogous to Example 22 (Step a)

After the solvent had been distilled off, the crude product was subjected to column chromatography on silica gel with toluene as the eluent.

400 mg of N-(2,6-diisopropylphenyl)-9-(bis-p-tert-octylphenyl)amino-1,6-diphenoxyperylene-3,4-dicarboximide were obtained in the form of a blue solid, which corresponds to a yield of 80%.

Step c):

Hydrolysis Analogous to Example 22 (Step b)

To a column chromatography on silica gel with toluene as the eluent was subjected.

200 mg of I31 were obtained in the form of a blue solid, which corresponds to a yield of 60%.

Analytical Data:

UV-Vis (CH$_2$Cl$_2$): $\lambda_{max}$ ($\epsilon$)=602, 487 nm;

MS (FD): m/z (rel. int.)=957.4 (100%) [M$^+$].

Example 32

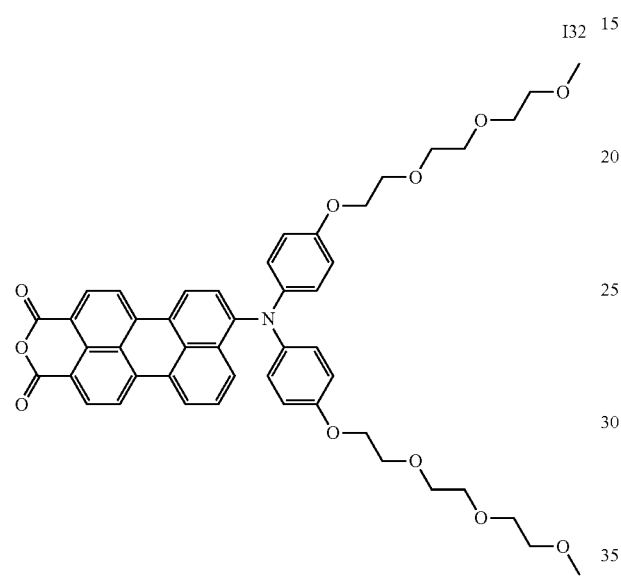

I32

The rylene derivative I32 was prepared proceeding from N-(2,6-diisopropylphenyl)-9-(bis-p-methyloxyphenyl)aminoperylene-3,4-dicarboximide (example 49), which was first converted to N-(2,6-diisopropylphenyl)-9-(bis-p-hydroxyphenyl)aminoperylene-3,4-dicarboximide (step a), which was then reacted with TEG-tosy (step b), which was subsequently hydrolyzed under alkaline conditions to give dicarboxylic anhydride I32 (step c).

Step a):

0.4 ml (4.2 mmol) of BBr$_3$ was added to a solution of N-(2,6-diisopropylphenyl)-9-(bis-p-methyloxyphenyl)aminoperylene-3,4-dicarboximide in 50 ml of dichloromethane at 0° C. After 3 h, 50 ml of water were added and the phases were separated.

After the solvent had been distilled off, N-(2,6-diisopropylphenyl)-9-(bis-p-hydroxyphenyl)aminoperylene-3,4-dicarboximide was isolated as a blue solid (48 mg, 99%).

Step b):

A mixture of 480 mg (0.70 mmol) of N-(2,6-diisopropylphenyl)-9-(bis-p-hydroxyphenyl)aminoperylene-3,4-dicarboximide, 890 mg (2.8 mmol) of TEG-tosy, 400 mg (2.8 mmol) of potassium carbonate and 100 ml of anhydrous toluene 0.45 was heated to 90° C. and kept at this temperature for 1 d.

Potassium hydroxide and 500 ml of tert-butanol were heated to reflux temperature for 16 h.

After the solvent had been distilled off, the crude product was subjected to column chromatography on silica gel with a methylene chloride/acetone mixture (10:1) as the eluent.

440 mg of N-(2,6-diisopropylphenyl)-9-(bis-p-triethyleneglycolphenyl)aminoperylene-3,4-dicarboximide were obtained in the form of a blue solid, which corresponds to a yield of 65%.

Analytical Data:

MS (FD): m/z (rel. int.)=974.4

Step c):

Hydrolysis Analogous to Example 22 (Step c)

To a column chromatography on silica gel to a methylene chloride/acetone mixture (10:1) as the eluent was subjected.

170 mg of I32 were obtained in the form of a blue solid, which corresponds to a yield of 54%.

Analytical Data:

UV-Vis (CH$_2$Cl$_2$): $\lambda_{max}$ ($\epsilon$)=612, 466 nm;

MS (FD): m/z (rel. int.)=813.3 (100%) [M$^+$].

Example 33

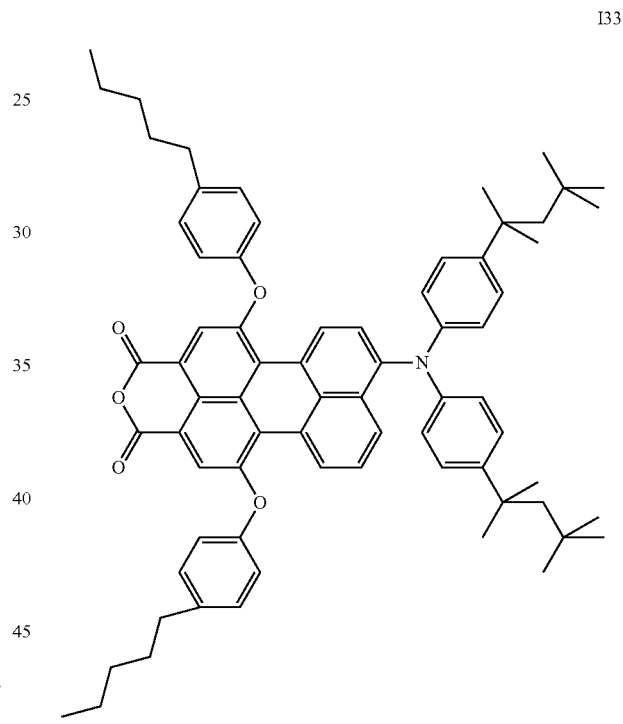

I33

The rylene derivative I33 was prepared proceeding from N-(2,6-diisopropylphenyl)-1,6,9-tribromoperylene-3,4-dicarboximide, which was converted first, under bromine exchange with 4-(n-pentyl)phenol, to N-(2,6-diisopropylphenyl)-1,6-bis[phenoxy]-9-bromoperylene-3,4-dicarboximide (step a), which was then converted a further bromine exchange with bis[(4-tert-octyl)phenyl]amine to the amine derivative (step b), which was then hydrolyzed under alkaline conditions to the dicarboxylic anhydride I33 (step c).

Step a):

Phenoxylation Analogous to Example 31

A column chromatography was subjected on silica gel with a methylene chloride/pentane mixture (1:2) as the eluent.

800 mg of N-(2,6-diisopropylphenyl)-1,6-bis[4-(n-pentyl)phenoxy]-9-bromoperylene-3,4-dicarboximide were obtained in the form of a red solid, which corresponds to a yield of 45%.

Step b):

Buchwald Analogous to Example 22 (Step a)

After the solvent had been distilled off, the crude product was subjected to column chromatography on silica gel with toluene as the eluent.

500 mg of N-(2,6-diisopropylphenyl)-9-(bis-p-tert-octylphenyl)amino-1,6-di(p-n-pentylphenoxy)perylene-3,4-dicarboximide were obtained in the form of a blue solid, which corresponds to a yield of 70%.

Step c):

Hydrolysis Analogous to Example 22 (Step b)

To a column chromatography on silica gel with toluene as the eluent was subjected.

150 mg of I33 were obtained in the form of a blue solid, which corresponds to a yield of 50%.

Analytical Data:

UV-Vis (CH$_2$Cl$_2$): $\lambda_{max}(\epsilon)$=603, 486 nm;

MS (FD): m/z (rel. int.)=1040.5 (100%) [M$^+$].

Example 34

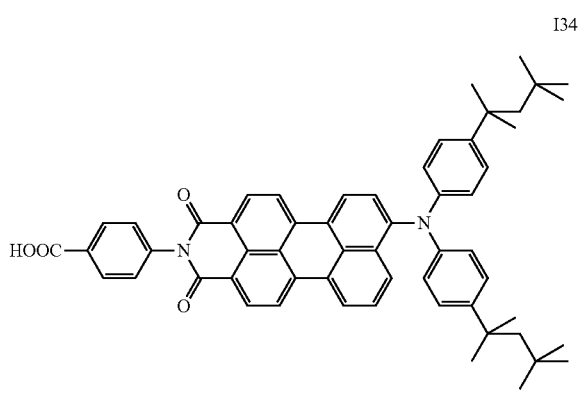 [SMILES: CC(C)(C)CC(C)(C)c1ccc(N(c2ccc(C(C)(C)CC(C)(C)C)cc2)c2ccc3c4ccc5c6c(ccc(c7cccc2c73)c64)C(=O)N(c2ccc(C(=O)O)cc2)C5=O)cc1]

I34

0.05 g (0.28 mmol) of anhydrous zinc acetate and 0.16 g (1.1 mmol) of 4-aminobenzoic acid were added under nitrogen to a mixture, initially charged under nitrogen, of 0.20 g (0.28 mmol) of N-(2,6-diisopropylphenyl)-9-[bis(4-tert-octyl)phenyl]aminoperylene-3,4-dicarboximide (example 7) and 10 ml of anhydrous N-methylpyrrolidone. The mixture was then heated to 160° C. and stirred at this temperature for 48 h.

After cooling to room temperature, the product was added to water, filtered off, washed with water and dried. It was subjected to column chromatography on silica gel with an acetone/methanol mixture (1:1) and then with pure methanol as the eluent.

0.038 g of a blue solid was obtained, which corresponds to a yield of 16%.

Analytical Data of I34:

UV-Vis (CH$_2$Cl$_2$): $\lambda_{max}$ ($\epsilon$)=640, 595 nm.

Example 35

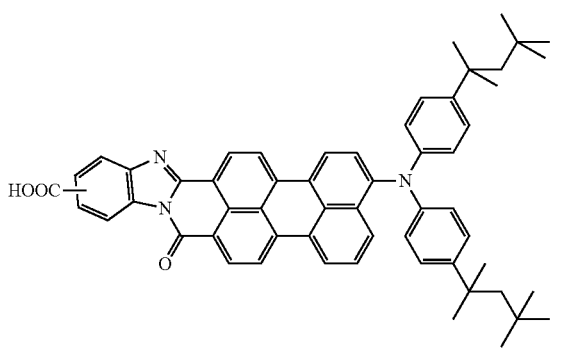

I35

The rylene derivative I35 is a mixture of two isomers with the carboxyl group in the 3 and 4 position on the phenylene ring respectively.

A solution of 0.10 g (0.14 mmol) of N-(2,6-diisopropylphenyl)-9-[bis(4-tert-octyl)phenyl]aminoperylene-3,4-dicarboximide (example 7) in 6 ml of quinoline was initially charged under nitrogen in a 50 ml Schlenk tube, then, likewise under nitrogen, 0.060 g (0.42 mmol) of 3,4-diaminobenzoic acid and 0.02 g of anhydrous zinc acetate were added in succession. The mixture was then heated to 220° C. under nitrogen and kept at this temperature while removing the water formed for 4 h.

After cooling to room temperature, the reaction mixture was added to a mixture of 100 ml of 6% by weight hydrochloric acid and stirred for approx. 12 h. The product precipitated in this way was filtered off, washed with hot water and dried at 70° C. under reduced pressure.

0.11 g of I35 was obtained in the form of a blue solid, which corresponds to a yield of 95%.

Analytical Data of the Isomer Mixture I35:

UV-Vis (CHCl$_3$): $\lambda_{max}$=606 (12 000) nm (M$^{-1}$ cm$^{-1}$);

Example 36

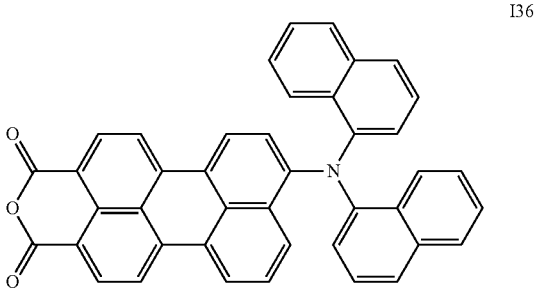 [SMILES: O=C1OC(=O)c2ccc3c4ccc(N(c5cccc6ccccc56)c5cccc6ccccc56)c5cccc(c6ccc1c2c63)c54]

I36

The rylene derivative I36 was prepared proceeding from N-(2,6-diisopropylphenyl)-9-bromoperylene-3,4-dicarboximide, which was converted first, under bromine exchange with N,N-di(naphth-1-yl)amine, to the amino-substituted dicarboximide (step a), which was subsequently hydrolyzed under alkaline conditions to the dicarboxylic anhydride I36 (step b).

Step a):

A mixture of 0.50 g (0.89 mmol) of N-(2,6-diisopropylphenyl)-9-bromoperylene-3,4-dicarboximide, 0.38 g (1.30 mmol) of N,N-di(naphth-1-yl)amine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene was heated to 80° C. under argon and stirred at this temperature for 16 h.

After the solvent had been distilled off, the crude product was subjected to column chromatography on silica gel with a methylene chloride/hexane mixture (10:1) as an eluent.

0.21 g of N-(2,6-diisopropylphenyl)-9-N,N-di(naphth-1-yl)aminoperylene-3,4-dicarboximide was obtained in the form of a violet solid, which corresponds to a yield of 32%.

Analytical Data:
UV-Vis (CH$_2$Cl$_2$): $\lambda_{max}$=523 nm;
MS (FD): m/z (rel. int.)=784.3 (100%) [M$^+$].

Step b):

A mixture of 200 mg (0.27 mmol) of N-(2,6-diisopropylphenyl)-9-N,N-di(naphth-1-yl)aminoperylene-3,4-dicarboximide, 0.45 g (8.0 mmol) of potassium hydroxide and 15 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent.

30 mg of I36 were obtained in the form of a violet solid, which corresponds to a yield of 19%.

Analytical Data of I36:
UV-Vis (CH$_2$Cl$_2$): $\lambda_{max}$ ($\epsilon$)=447 (21 000) nm (M$^{-1}$ cm$^{-1}$);
MS (FD): m/z (rel. int.)=589.1 (100%) [M$^+$].

Example 37

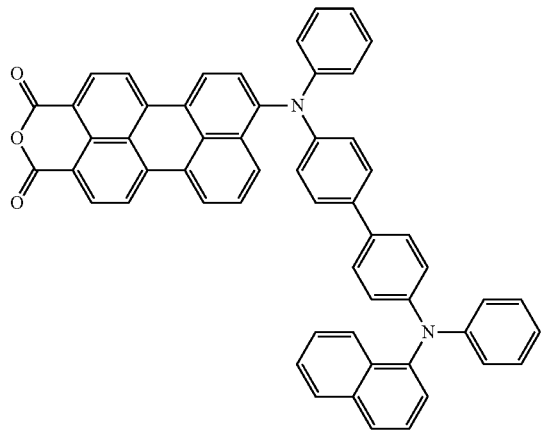

I37

The rylene derivative I37 was prepared proceeding from N-(2,6-diisopropylphenyl)-9-bromoperylene-3,4-dicarboximide, which was converted first, under bromine exchange with N,N-diphenyl-N'-naphth-1-ylbenzidine, to the amino-substituted dicarboximide (step a), which was subsequently hydrolyzed under alkaline conditions to the dicarboxylic anhydride I37 (step b).

Step a):

A mixture of 0.50 g (0.89 mmol) of N-(2,6-diisopropylphenyl)-9-bromoperylene-3,4-dicarboximide, 0.62 g (1.30 mmol) of N,N,N'-triphenyl-p-phenylenediamine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene was heated to 80° C. under nitrogen and stirred at this temperature for 16 h.

After the solvent had been distilled off, the crude product was subjected to column chromatography on silica gel with dichloromethane as the eluent.

0.650 g of the amine-substituted perylene was obtained in the form of a blue solid, which corresponds to a yield of 79%.

Analytical Data:
UV-Vis (CH$_2$Cl$_2$): $\lambda_{max}$=573 nm
MS (FD): m/z (rel. int.)=941.3 (100%) [M$^+$].

Step b):

A mixture of 650 mg of peryleneamine derivative (from step a), 1.2 g (21.0 mmol) of potassium hydroxide and 15 ml of tert-butanol was heated to reflux temperature for 16 h.

After cooling to 40° C., 50% by weight acetic acid was added to the reaction mixture, which was stirred at this temperature for 1 h. The product was extracted by shaking with dichloromethane, concentrated by rotary evaporation, dried and subjected to column chromatography on silica gel with methylene chloride as the eluent.

310 mg of I37 were obtained in the form of a blue solid, which corresponds to a yield of 54%.

Analytical Data of I37:
UV-Vis (CH$_2$Cl$_2$): $\lambda_{max}$($\epsilon$)=593 (24 000) nm;
MS (FD): m/z (rel. int.)=782.0 (100%) [M$^+$].

Example 38

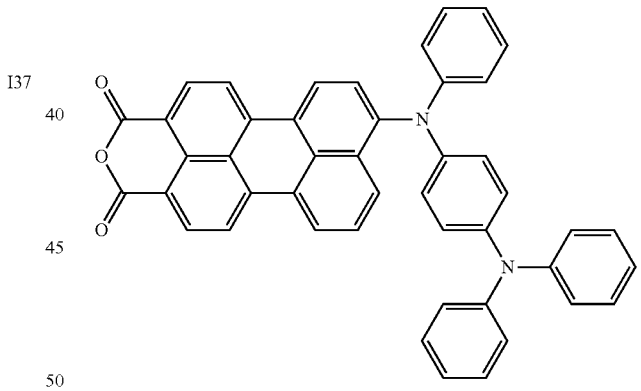

I38

The rylene derivative I38 was prepared proceeding from N-(2,6-diisopropylphenyl)-9-bromoperylene-3,4-dicarboximide, which was converted first, under bromine exchange with N,N,N'-triphenyl-p-phenylenediamine, to the amino-substituted dicarboximide (step a), which was subsequently hydrolyzed under alkaline conditions to the dicarboxylic anhydride I38 (step b).

Step a):

A mixture of 0.50 g (0.89 mmol) of N-(2,6-diisopropylphenyl)-9-bromoperylene-3,4-dicarboximide, 0.46 g (1.30 mmol) of N,N,N'-triphenyl-p-phenylenediamine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene were heated to 80° C. under nitrogen and stirred at this temperature for 16 h.

After the solvent had been distilled off, the crude product was subjected to column chromatography on silica gel with chloroform as the eluent.

0.285 g of the amine-substituted perylene was obtained in the form of a violet solid, which corresponds to a yield of 39%.

Analytical Data:
UV-Vis (CH$_2$Cl$_2$): $\lambda_{max}$=598 nm
MS (FD): m/z (rel. int.)=815.3 (100%) [M$^+$].

Step b):
A mixture of 450 mg (0.55 mmol) of peryleneamine derivative (from step a), 0.93 g (17.0 mol) of potassium hydroxide and 15 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent. 72 mg of I38 were obtained in the form of a blue solid, which corresponds to a yield of 20%.

Analytical Data of I38:
UV-Vis (CH$_2$Cl$_2$): $\lambda_{max}$ ($\epsilon$)=568 nm (25 000)
MS (FD): m/z (rel. int.)=656.1 (100%) [M$^+$].

Example 39

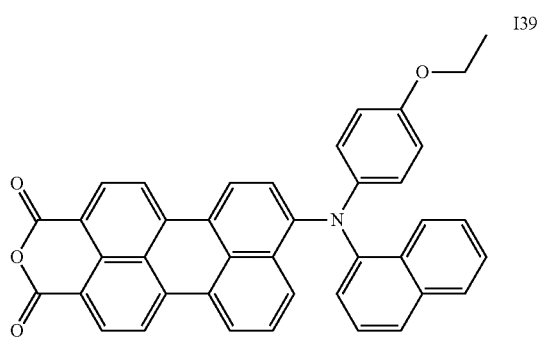 [SMILES: CCOc1ccc(N(c2cccc3ccccc23)c2ccc3c4ccc5c6c(ccc(c7cccc2c73)c64)C(=O)OC5=O)cc1]

The rylene derivative I39 was prepared proceeding from N-(2,6-diisopropylphenyl)-9-bromoperylene-3,4-dicarboximide, which was converted first, under bromine exchange with N-(4-ethoxyphenyl)-1-naphthylamine, to the amino-substituted dicarboximide (step a), which was then hydrolyzed under alkaline conditions to the dicarboxylic anhydride I39 (step b).

Step a):
A mixture of 0.50 g (0.89 mmol) of N-(2,6-diisopropylphenyl)-9-bromoperylene-3,4-dicarboximide, 0.40 g (1.30 mmol) of N-(4-ethoxyphenyl)-1-naphthylamine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene was heated to 80° C. under argon and stirred at this temperature for 5 h.

After the solvent had been distilled off, the crude product was subjected to column chromatography on silica gel with dichloromethane as the eluent.

0.13 g of N-(2,6-diisopropylphenyl)-9-N-(4-ethoxyphenyl)-1-naphthylaminoperylene-3,-4-dicarboximide was obtained in the form of a blue solid, which corresponds to a yield of 20%.

Analytical Data:
UV-Vis (CH$_2$Cl$_2$): $\lambda_{max}$=575 nm;
MS (FD): m/z (rel. int.)=742.3 (100%) [M$^+$].

Step b):
A mixture of 120 mg (0.16 mmol) of N-(2,6-diisopropylphenyl)-9-(N-(4-ethoxyphenyl)-1-naphthylaminoperylene-3-,4-dicarboximide, 0.27 g (4.9 mmol) of potassium hydroxide and 10 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent.

20 mg of I39 were obtained in the form of a blue solid, which corresponds to a yield of 22%.

Analytical Data of I39:
UV-Vis (CH$_2$Cl$_2$): $\lambda_{max}$ ($\epsilon$)=457 (21 000) nm (M$^{-1}$ cm$^{-1}$);
MS (FD): m/z (rel. int.)=583.3 (100%) [M$^+$].

Example 40

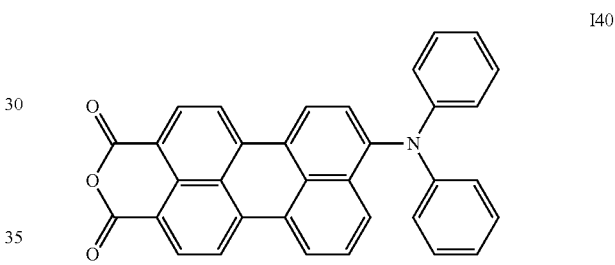

The rylene derivative I40 was prepared proceeding from N-(2,6-diisopropylphenyl)-9-bromoperylene-3,4-dicarboximide, which was converted initially, under bromine exchange with diphenylamine, to the amino-substituted dicarboximide (step a), which was then hydrolyzed under alkaline conditions to the dicarboxylic anhydride I40 (step b).

Step a):
A mixture of 0.50 g (0.89 mmol) of N-(2,6-diisopropylphenyl)-9-bromoperylene-3,4-dicarboximide, 0.20 g (1.30 mmol) of diphenylamine, 20 mg (0.018 mmol) of tris(dibenzylideneacetone)dipalladium(0), 90 mg (0.045 mmol) of tris(tert-butyl)-phosphine, 130 mg (1.3 mmol) of sodium tert-butoxide and 10 ml of dry toluene was heated to 80° C. under argon and stirred at this temperature for 16 h.

After the solvent had been distilled off, the crude product was subjected to column chromatography on silica gel with dichloromethane as the eluent.

0.48 g of the amine-substituted perylene was obtained in the form of a violet solid, which corresponds to a yield of 83%.

Analytical Data:
UV-Vis (CH$_2$Cl$_2$): $\lambda_{max}$=557 nm
MS (FD): m/z (rel. int.)=648.2 (100%) [M$^+$].

Step b):
A mixture of 450 mg (0.70 mmol) of peryleneamine (from step a), 1.2 g (21.0 mmol) of potassium hydroxide and 10 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent.

60 mg of I40 were obtained in the form of a blue solid, which corresponds to a yield of 18%.

Analytical Data of I40:

UV-Vis (CH$_2$Cl$_2$): $\lambda_{max}$ ($\epsilon$)=445 (21 000) nm (M$^{-1}$ cm$^{-1}$);

MS (FD): m/z (rel. int.)=489.0 (100%) [M$^+$].

Example 41

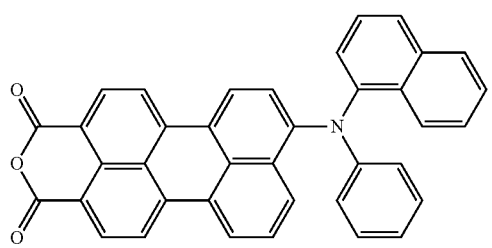

The rylene derivative I41 was prepared proceeding from N-(2,6-diisopropylphenyl)-9-bromoperylene-3,4-dicarboximide, which was converted initially, under bromine exchange with N-phenyl-1-naphthylamine, to the amino-substituted dicarboximide (step a), which was then hydrolyzed under alkaline conditions to the dicarboxylic anhydride I41 (step b).

Step a):

A mixture of 0.50 g (0.89 mmol) of N-(2,6-diisopropylphenyl)-9-bromoperylene-3,4-dicarboximide, 0.30 g (1.30 mmol) of N-phenyl-1-naphthylamine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene was heated to 80° C. under argon and stirred at this temperature for 16 h.

After the solvent had been distilled off, the crude product was subjected to column chromatography on silica gel with dichloromethane as the eluent.

0.39 g of the amine-substituted perylene was obtained in the form of a violet solid, which corresponds to a yield of 62%.

Analytical Data:

MS (FD): m/z (rel. int.)=698.2 (100%) [M$^+$].

Step b):

A mixture of 350 mg (0.50 mmol) of peryleneamine derivative (from step a), 0.84 g (15.0 mol) of potassium hydroxide and 20 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent.

79 mg of I41 were obtained in the form of a blue-violet solid, which corresponds to a yield of 30%.

Analytical Data of I41:

UV-Vis (CH$_2$Cl$_2$): $\lambda_{max}$ ($\epsilon$)=569 (21 000) nm (M$^{-1}$ cm$^{-1}$);

MS (FD): m/z (rel. int.)=539.0 (100%) [M$^+$].

Example 42

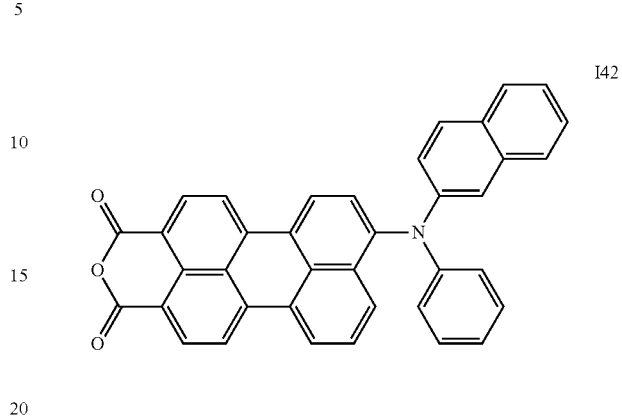

The rylene derivative I42 was prepared proceeding from N-(2,6-diisopropylphenyl)-9-bromoperylene-3,4-dicarboximide, which was converted initially, under bromine exchange with N-phenyl-2-naphthylamine, to the amino-substituted dicarboximide (step a), which was then hydrolyzed under alkaline conditions to the dicarboxylic anhydride I42 (step b).

Step a):

A mixture of 0.50 g (0.89 mmol) of N-(2,6-diisopropylphenyl)-9-bromoperylene-3,4-dicarboximide, 0.30 g (1.30 mmol) of N-phenyl-2-naphthylamine, 20 mg (0.018 mmol) of tris(dibenzylideneacetone)dipalladium(0), 90 mg (0.045 mmol) of tris(tert-butyl)phosphine, 130 mg (1.3 mmol) of sodium tert-butoxide and 10 ml of dry toluene was heated to 80° C. under argon and stirred at this temperature for 16 h.

After the solvent had been distilled off, the crude product was subjected to column chromatography on silica gel with chloroform as the eluent.

0.41 g of the amine-substituted perylene was obtained in the form of a blue-violet solid, which corresponds to a yield of 65%.

Analytical Data:

UV-Vis (CH$_2$Cl$_2$): $\lambda_{max}$=561 nm;

MS (FD): m/z (rel. int.)=698.2 (100%) [M$^+$].

Step b):

A mixture of 350 mg (0.50 mmol) of peryleneamine derivative (from step a), 0.84 g (15.0 mol) of potassium hydroxide and 20 ml of tert-butanol was heated to reflux temperature for 16 h.

After cooling to 40° C., 50% by weight acetic acid was added to the reaction mixture, which was stirred at this temperature for 1 h. The product was precipitated in water, filtered off, washed to neutrality with water, dried and subjected to column chromatography on silica gel with methylene chloride as the eluent.

120 mg of I42 were obtained in the form of a blue-violet solid, which corresponds to a yield of 44%.

Analytical Data of I42:

UV-Vis (CH$_2$Cl$_2$): $\lambda_{max}$ ($\epsilon$)=576 (21 000) nm (M$^{-1}$ cm$^{-1}$);

MS (FD): m/z (rel. int.)=539.1 (100%) [M$^+$].

Example 43

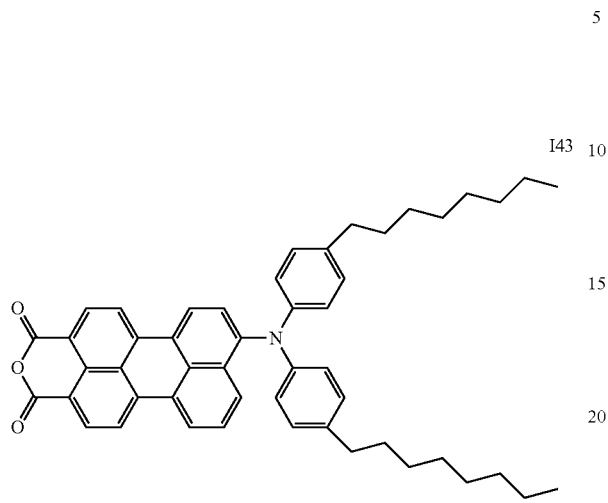

The rylene derivative I43 was prepared proceeding from N-(2,6-diisopropylphenyl)-1,6-bis[(4-tert-octyl)phenoxy]-9-bromoperylene-3,4-dicarboximide, which was converted initially, under bromine exchange with bis[(4-tert-octyl)phenyl]amine, to the substituted dicarboximide (step a), which was then hydrolyzed under alkaline conditions to the dicarboxylic anhydride I43 (step b).

Step a):

Buchwald Analogous to Example 22 (Step a)

After the solvent had been distilled off, the crude product was subjected to column chromatography on silica gel with dichloromethane as the eluent.

700 mg of N-(2,6-diisopropylphenyl)-9-bis(4-octylphenyl)aminoperylene-3,4-dicarboximide were obtained in the form of a violet solid, which corresponds to a yield of 90%.

Analytical Data:
UV-Vis (CH$_2$Cl$_2$): $\lambda_{max}$ ($\epsilon$)=582 (33 200) nm (M$^{-1}$ cm$^{-1}$);
MS (FD): m/z (rel. int.)=873.9 (100%) [M$^+$].

Step b):

Hydrolysis Analogous to Example 22 (Step b)

To a column chromatography on silica gel with toluene as the eluent was subjected.

350 mg of I43 were obtained in the form of a violet solid, which corresponds to a yield of 72%.

Analytical Data:
UV-Vis (CH$_2$Cl$_2$): $\lambda_{max}$ ($\epsilon$)=596 (16 000) nm (M$^{-1}$ cm$^{-1}$);
MS (FD): m/z (rel. int.)=713.4 (100%) [M$^+$].

Example 44

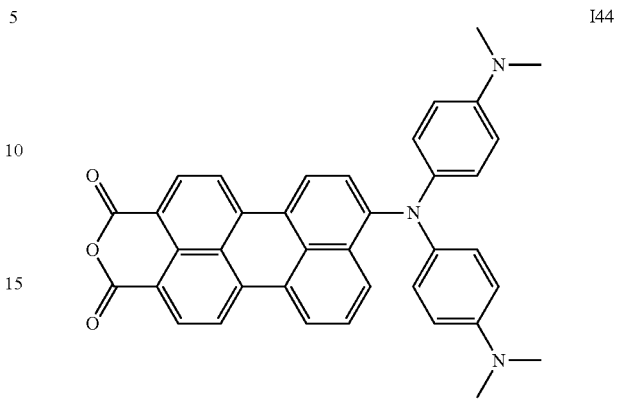

The rylene derivative I44 was prepared proceeding from N-(2,6-diisopropylphenyl)-9-bromoperylene-3,4-dicarboximide, which was converted first, under bromine exchange with Bindschedler's Green, to the amino-substituted dicarboximide (step a), which was subsequently hydrolyzed under alkaline conditions to the dicarboxylic anhydride I44 (step b).

Step a):

A mixture of 0.50 g (0.89 mmol) of N-(2,6-diisopropylphenyl)-9-bromoperylene-3,4-dicarboximide, 0.34 g (1.30 mmol) of Bindschedler's Green, 40 mg (0.045 mmol) of tris(dibenzylideneacetone)dipalladium(0), 0.45 ml (0.45 mmol) of tris(tert-butyl)phosphine, 120 mg (1.3 mmol) of sodium tert-butoxide and 30 ml of dry toluene was heated to 80° C. under argon and stirred at this temperature for 16 h.

After the solvent had been distilled off, the crude product was subjected to column chromatography on silica gel with a methylene chloride/ethanol mixture (50:1) as the eluent.

0.35 g of peryleneamine derivative was obtained in the form of a green solid, which corresponds to a yield of 53%.

Analytical Data:
UV-Vis (CH$_2$Cl$_2$): $\lambda_{max}$=667 nm;
MS (FD): m/z (rel. int.)=734.2 (100%) [M$^+$].

Step b):

N-(2,6-Diisopropylphenyl)-9-[bis(4-tert-octyl)phenyl]aminoperylene-3,4-dicarboximide A mixture of 330 mg (0.45 mmol) of N-(2,6-diisopropylphenyl)-9-[bis(4-bismethylamino)phenyl]aminoperylene-3,-4-dicarboximide, 0.76 g (13.5 mmol) of potassium hydroxide and 50 ml of tert-butanol was heated to reflux temperature for 16 h.

After cooling to 70° C., 50% by weight acetic acid was added to the reaction mixture and the mixture was stirred at this temperature for 1 h. The product was precipitated in water, filtered off, washed to neutrality with water, dried and subjected to column chromatography on silica gel with 50:1 methylene chloride/ethanol as the eluent.

30 mg of I44 were obtained in the form of a blue solid, which corresponds to a yield of 11%.

Analytical Data of I44:
UV-Vis (CH$_2$Cl$_2$): $\lambda_{max}$ ($\epsilon$)=689 (21 000) nm (M$^{-1}$ cm$^{-1}$);
MS (FD): m/z (rel. int.)=575.1 (100%) [M$^+$].

Example 45

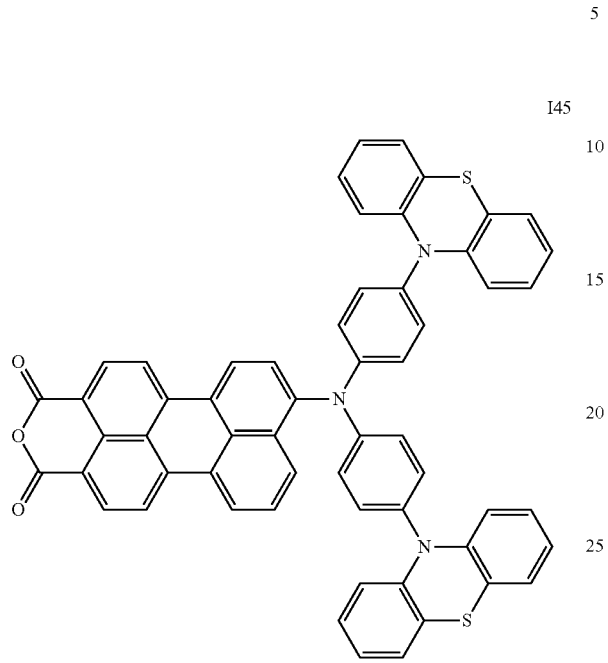

The rylene derivative 145 was prepared proceeding from N-(2,6-diisopropyl-phenyl)-1,6-bis[(4-tert-octyl)phenoxy]-9-bromoperylene-3,4-dicarboximide, which was converted first, under bromine exchange with bis(4-phenothiazinyl)phenyl)amine, to the substituted dicarboximide (step a), which was subsequently hydrolyzed under alkaline conditions to the dicarboxylic anhydride 145 (step b).

Step a):

Buchwald Analogous to Example 22 (Step a)

After the solvent had been distilled off, the crude product was subjected to column chromatography on silica gel with dichloromethane as the eluent.

1.2 g of N-(2,6-diisopropylphenyl)-9-bis-(phenothiazinylphenyl)aminoperylene-3,4-d-icarboximide were obtained in the form of a violet solid, which corresponds to a yield of 81%.

Analytical Data:

UV-Vis (CH$_2$Cl$_2$): $\lambda_{max}$=544 nm;

MS (FD): m/z (rel. int.)=1045.3 (100%) [M$^+$].

Step b):

Hydrolysis Analogous to Example 22 (Step b)

To a column chromatography on silica gel with dichloromethane as the eluent was subjected.

400 mg of I45 were obtained in the form of a violet solid, which corresponds to a yield of 59%.

Analytical Data:

UV-Vis (CH$_2$Cl$_2$): $\lambda_{max}$ ($\epsilon$)=556 (6 000) nm (M$^{-1}$ cm$^{-1}$);

MS (FD): m/z (rel. int.)=884.5 (100%) [M$^+$].

Example 46

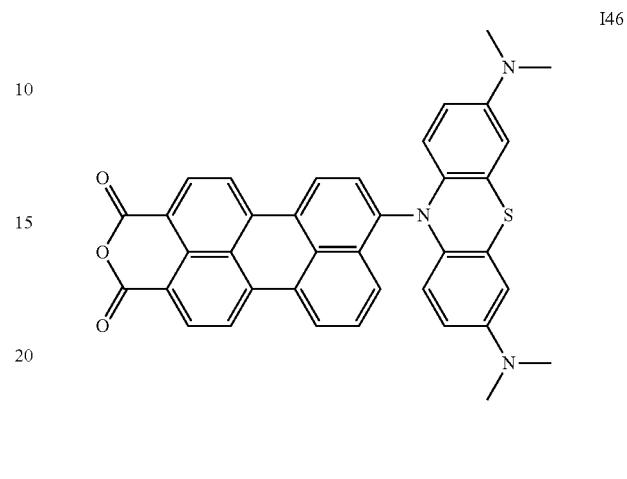

The rylene derivative I46 was prepared proceeding from N-(2,6-diisopropylphenyl)-9-bromoperylene-3,4-dicarboximide which was converted first, under bromine exchange with 3,7-bis(dimethylamino)phenothiazine (first after the deprotection of (3,7-bis(dimethylamino)phenothiazin-10-yl)phenylmethanone) to the phenothiazine-substituted dicarboximide (step a), which was subsequently hydrolyzed under alkaline conditions to the dicarboxylic anhydride I46 (step b).

Step a):

A mixture of (3,7-bis(dimethylamino)phenothiazin-10-yl)phenylmethanone (1.5 g, 3.8 mmol), sodium hydroxide (310 mg, 3.8 mmol), THF (5 ml) and methanol (15 ml) was heated to reflux temperature for 12 h. After starting to cool, the solvent was removed with argon.

A mixture of 1.5 g (3.1 mmol) of N-(2,6-diisopropylphenyl)-9-bromoperylene-3,4-dicarboximide, 0.123 g (0.13 mmol) of tris(dibenzylideneacetone)dipalladium(0), 27 mg (0.13 mmol) of tris(tert-butyl)phosphine, 12 mg (0.13 mmol) of sodium tert-butoxide and 100 ml of dry toluene was added thereto under argon, heated to 80° C. and stirred at this temperature for 16 h.

After the solvent had been distilled off, the crude product was subjected to column chromatography on silica gel with a methylene chloride/methanol mixture (20:1) as the eluent.

0.500 g of N-(2,6-diisopropylphenyl)-9-(3,7-bis(dimethylamino)phenothiazin-10-yl)-pe-rylene-3,4-dicarboximide was obtained in the form of a brown solid, which corresponds to a yield of 17%.

Analytical Data:

UV-Vis (CH$_2$Cl$_2$): $\lambda_{max}$=510, 486 nm

MS (FD): m/z (rel. int.)=765.0 (100%) [M$^+$].

Step b):

Hydrolysis Analogous to Example 22 (Step b)

To a column chromatography on silica gel with a methylene chloride/methanol mixture (20:1) as the eluent was subjected.

200 mg of I46 were obtained in the form of a brown solid, which corresponds to a yield of 72%.

Analytical Data:
MS (FD): m/z (rel. int.)=606.0 (100%) [M⁺].

Example 47

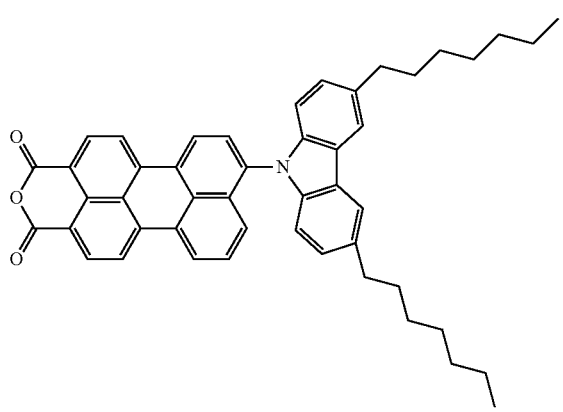 [SMILES: CCCCCCCc1ccc2c(c1)c1cc(CCCCCCC)ccc1n2-c1ccc2c3ccc4c5c(ccc(c6cccc1c62)c53)C(=O)OC4=O]

The rylene derivative I47 was prepared proceeding from N-(2,6-diisopropylphenyl)-1,6-bis[(4-tert-octyl)phenoxy]-9-bromoperylene-3,4-dicarboximide, which was converted first, under bromine exchange with 3,6-bisheptylcarbazole, to the substituted dicarboximide (step a), which was subsequently hydrolyzed under alkaline conditions to the dicarboxylic an hydride I47 (step b).

Step a):
Buchwald Analogous to Example 22 (Step a)
After the solvent had been distilled off, the crude product was subjected to column chromatography on silica gel with dichloromethane as the eluent.

400 mg of N-(2,6-diisopropylphenyl)-9-(3,6-diheptylcarbazol-9-yl)perylene-3,4-dicar-boximide were obtained in the form of a violet solid, which corresponds to a yield of 85%.

Analytical Data:
UV-Vis (CH$_2$Cl$_2$): $\lambda_{max}$=514 nm

Step b):
Hydrolysis Analogous to Example 22 (Step b)
To a column chromatography on silica gel with dichloromethane as the eluent was subjected.

80 mg of I46 were obtained in the form of a violet solid, which corresponds to a yield of 49%.

Analytical Data:
UV-Vis (CH$_2$Cl$_2$): $\lambda_{max}$ (ε)=596 (16 000) nm (M$^{-1}$ cm$^{-1}$);
MS (FD): m/z (rel. int.)=713.4 (100%) [M⁺].

Example 48

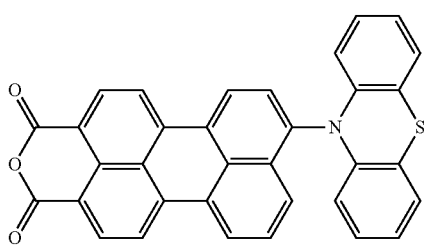

I48

The rylene derivative I48 was prepared proceeding from N-(2,6-diisopropylphenyl)-9-bromoperylene-3,4-dicarboximide, which was converted first, under bromine exchange with phenothiazine, to the amino-substituted dicarboximide (step a), which was subsequently hydrolyzed under alkaline conditions to the dicarboxylic anhydride I48 (step b).

Step a):
A mixture of 0.50 g (0.89 mmol) of N-(2,6-diisopropylphenyl)-9-bromoperylene-3,4-dicarboximide, 0.40 g (1.30 mmol) of phenothiazine, 70 mg (0.08 mmol) of tris(dibenzylideneacetone)dipalladium(0), 65 mg (0.9 mmol) of BINAP, 340 mg (3.6 mmol) of sodium tert-butoxide and 40 ml of dry toluene was heated to 80° C. under nitrogen and stirred at this temperature for 3 d.

After the solvent had been distilled off, the crude product was subjected to column chromatography on silica gel with dichloromethane as the eluent.

0.5 g of the phenothiazinyl-substituted perylene was obtained as red solid, which corresponds to a yield of 41%.

Analytical Data:
MS (FD): m/z (rel. int.)=678.2 (100%) [M⁺].

Step b):
A mixture of 500 mg (0.7 mmol) of perylenephenothiazine derivative, 2.0 g (35.0 mol) of potassium hydroxide and 20 ml of tert-butanol was heated to reflux temperature for 16 h.

After cooling to 40° C., 50% by weight of acetic acid was added to the reaction mixture and the mixture was stirred at this temperature for 1 h. The product was precipitated in water, filtered off, washed to neutrality with water, dried and subjected to column chromatography on silica gel with methylene chloride as the eluent.

90 mg of I48 were obtained in the form of a red solid, which corresponds to a yield of 25%.

Analytical Data of I48:
UV-Vis (CH$_2$Cl$_2$): $\lambda_{max}$ (ε)=432 (21 000) nm (M$^{-1}$ cm$^{-1}$);
MS (FD): m/z (rel. int.)=519.0 (100%) [M⁺].

Example 49

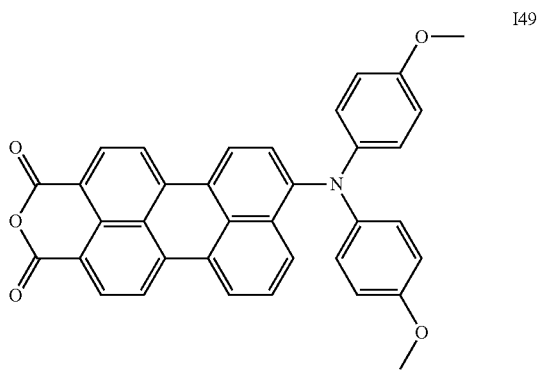 [SMILES: COc1ccc(N(c2ccc(OC)cc2)c2ccc3c4ccc5c6c(ccc(c7cccc2c73)c64)C(=O)OC5=O)cc1]

I49

The rylene derivative I49 was prepared proceeding from N-(2,6-diisopropylphenyl)-9-bromoperylene-3,4-dicarboximide, which was converted first, under bromine exchange with 4,4-dimethoxydiphenylamine, to the amino-substituted dicarboximide (step a), which was then hydrolyzed under alkaline conditions to the dicarboxylic anhydride I49 (step b).

Step a):
A mixture of 1.0 g (1.8 mmol) of N-(2,6-diisopropylphenyl)-9-bromoperylene-3,4-dicarboximide, 0.8 g (3.6 mmol) of 4,4-dimethoxydiphenylamine, 80 mg (0.08 mmol) of tris (dibenzylideneacetone)dipalladium(0), 560 mg (0.9 mmol) of BINAP, 340 mg (3.6 mmol) of sodium tert-butoxide and 40 ml of dry toluene was heated to 80° C. under nitrogen and stirred at this temperature for 16 h.

After the solvent had been distilled off, the crude product was subjected to column chromatography on silica gel with dichloromethane as the eluent.

0.2 g of N-(2,6-diisopropylphenyl)-9-[bis(4-methoxy)phenyl]aminoperylene-3,4-dicarboximide was obtained in the form of a blue solid, which corresponds to a yield of 15%.

Analytical Data:
UV-Vis ($CH_2Cl_2$): $\lambda_{max}$=597 nm
MS (FD): m/z (rel. int.)=709.1 (100%) [M$^+$].

Step b):

A mixture of 150 mg (0.2 mmol) of N-(2,6-diisopropylphenyl)-9-[bis(4-methoxy)phenyl]aminoperylene-3,4-dicarboximide, 0.65 g (10.0 mmol) of potassium hydroxide and 10 ml of tert-butanol was heated to reflux temperature for 16 h.

After cooling to 40° C., 50% by weight of acetic acid was added to the reaction mixture, which was stirred at this temperature for 1 h. The product was precipitated in water, filtered off, washed to neutrality with water, dried and subjected to column chromatography on silica gel with methylene chloride as the eluent.

25 mg of I49 were obtained in the form of a blue solid, which corresponds to a yield of 23%.

Analytical Data of I49:
UV-Vis ($CH_2Cl_2$): $\lambda_{max}$ ($\epsilon$)=474 (21 000) nm ($M^{-1}$ $cm^{-1}$);
MS (FD): m/z (rel. int.)=549.1 (100%) [M$^+$].

II. Use of Rylene Derivatives I

In order to test the suitability of the rylene derivatives I as dye sensitizers in solar cells, solar cells were produced as follows.

The base material used was glass plaques coated with fluorine-doped tin oxide (FTO), and of dimensions 12 mm×14 mm×3 mm or 25 mm×15 mm×3 mm (Pilkington TEC 8), which had been treated successively with glass cleaner, acetone and ethanol, in each case in an ultrasound bath for 15 min, then stored in ethanol and, before use, dried in a nitrogen stream.

To produce the counterelectrode, 20 µl of a 5 mm solution of $H_2PtCl_6$ in isopropanol were distributed uniformly on the coated side of an FTO glass plaque with drillholes, and, after brief drying under air, sintered at 380° C. for 30 min and subsequently stored in a dust-free environment.

To prepare the working electrode, the procedure was as follows:

A round hole of diameter 10 mm was punched out of adhesive tape. The adhesive tape was then adhesive-bonded as a template to the coated side of an FTO glass plaque without drillholes. A doctor blade was then used once or more than once to apply a paste consisting predominantly of the particular semiconductor metal oxide.

After removal of the adhesive tape and brief drying at 80° C., the metal oxide-coated glass plaque was sintered at 450° C. for 30 min, then allowed to cool to 80° C., and then placed into a from $5\times10^{-4}$ to $1\times10^{-5}$ M solution of the particular rylene derivative I in an organic solvent for from 1 to 24 h. The glass plaque removed from the solution was rinsed off to the corresponding solvent and dried in a nitrogen stream.

Further details on the production of the working electrode can be taken from the examples.

The glass plaques were subsequently sealed thus with a 50 µm-thick hotmelt adhesive film (Surlyn® 1702; DuPont). The intermediate space between the two electrodes was then filled through the drillholes with the particular electrolyte specified in the examples.

After sealing the drillholes with further hotmelt adhesive film, the contact surfaces of working electrode and counterelectrode were coated with conductive silver lacquer and adhesive-bonded with copper adhesive tape (3 m).

The cells thus produced had an active surface of 0.32 $cm^2$ and 0.502 $cm^2$ respectively.

The quantum efficiency (IPCE=Incident Photon-to-current Conversion Efficiency) was then measured with a 75 watt xenon arc lamp (LOT-Oriel), a ⅛ m monochromator (SpectraPro-2150i; Acton Research Corporation), a transimpedance amplifier (Aescusoft GmbH Automation) and a lock-in amplifier 7265 (signal recovery).

To determine the efficiency .eta., the particular current/voltage characteristic was measured with a source meter model 2400 (Keithley Instruments Inc.) under irradiation with a halogen lamp field (Xenophot® 64629; Osram) (examples 1-3) or with a xenon lamp (300 W Xe Arc Lamp, LSN252, LOT Oriel Group) (examples 4-5) as a sun simulator.

The following rylene derivatives I were tested:
Dye A: Rylene derivative I2 from example 2
Dye B: N-(2,6-diisopropylphenyl)-1,6,9,14-tetra[(4-tert-octyl)phenoxy]terrylene-3,4:11,12-tetracarboxylic monoimide monoanhydride, prepared according to example 1 of the prior German patent application 10 2005 021 362.6
Dye C: N-(2,6-Diisopropylphenyl)-1,6,11,16-tetra[(4-tert-octyl)phenoxy]quaterrylene-3,4:13,14-tetracarboxylic monoimide monoanhydride, prepared according to example 8 of the prior German patent application 10 2005 021 362.6
Dye D: Rylene derivative I6 from example 6
Dye E: Rylene derivative I7 from example 7
Dye F: Rylene derivative I8 from example 8
Dye G: Rylene derivative I9 from example 9
Dye H: Rylene derivative I32 from example 24
Dye I: Rylene derivative I34 from example 34
Dye J: Rylene derivative I35 from example 35
For comparison, the ruthenium complex N-179 (dye V), whose structure is described, for example, in J. Chem. Phys. B 107, p. 13280-13285 (2003), was tested.

Example 1

Dye B was used in a $TiO_2$ solar cell.
Description of the Cell and of the Starting Materials:
FTO-coated glass plaques of dimensions 25 mm×15 mm×3 mm $TiO_2$ paste Ti-Nanoxide HT (Solaronix SA) $TiO_2$ layer thickness after sintering (450° C./30 min): 9 µm 500 mM solution of dye B in toluene (inserted at 80° C.), insertion time 14 h at room temperature Electrolyte: 0.5 M LiI, 0.25 M tetrabutylammonium iodide and 0.05 M $I_2$ in methoxypropionitrile active area: 0.502 $cm^2$ For comparison, dye V was used in a $TiO_2$ solar cell. The parameters agreed, unless stated otherwise, with the above-mentioned parameters.

$TiO_2$ layer thickness after sintering: 17 µm 0.5 mM solution of dye V in ethanol (inserted at 80° C.), insertion time 14 h at room temperature Electrolyte: 0.5 M LiI, 0.6 M tetrabutylammonium iodide, 0.05 M $I_2$ and 0.5 M 4-tert-butylpyridine in acetonitrile Both solar cells were illuminated under 0.1 sun.
The current/voltage curves measured are depicted in FIG. 1.

The efficiencies η determined were 2.25% for dye B and 5.06% for dye V.

Example 2

Figure 2:
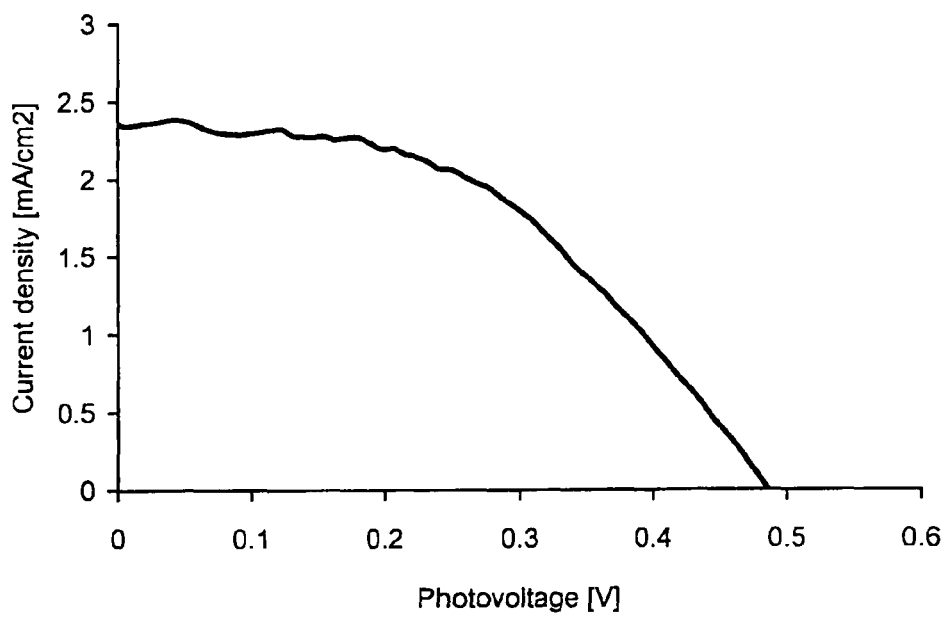
FIG. 2 depicts a current/voltage curve for the solar cell of Example 2.

Dye B was used in a ZnO solar cell.
Description of the Cell and of the Starting Materials:
FTO-coated glass plaques of dimensions 12 mm×14 mm×3 mm ZnO paste, prepared according to the recipe described in J. Phys. Chem. B 105, p. 5585-5587 (2001) ZnO layer thickness after sintering (350° C./30 min): 0.9 μm 0.5 mM solution of dye B in N-methylpyrrolidone, insertion time 14 h at 50° C. Electrolyte: 0.6 M tetrabutylammonium iodide and 0.05 M $I_2$ in methoxypropionitrile active area: 0.32 cm$^2$ The solar cell was illuminated under 1 sun.
The current/voltage curve measured is depicted in FIG. 2.
The efficiency η determined was 0.54%.

Example 3

Dyes A, B and C were each used in a $TiO_2$ solar cell.
Description of the Cell and of the Starting Materials:
FTO-coated glass plaques of dimensions 25 mm×15 mm×3 mm $TiO_2$ paste with a $TiO_2$ particle size of 25 nm (ECN) $TiO_2$ layer thickness after sintering (450° C./30 min): 4 μm 0.5 mM solution of the particular dye in toluene (inserted at 80° C.), insertion time 14 h at room temperature Electrolyte: 0.5 M LiI, 0.05 M $I_2$ and 0.5 M 4-tert-butylpyridine in methoxypropionitrile active area: 0.502 cm$^2$ For comparison, the dye V was used in a $TiO_2$ solar cell. The parameters agreed, unless stated otherwise, with the abovementioned parameters.

Figure 3:
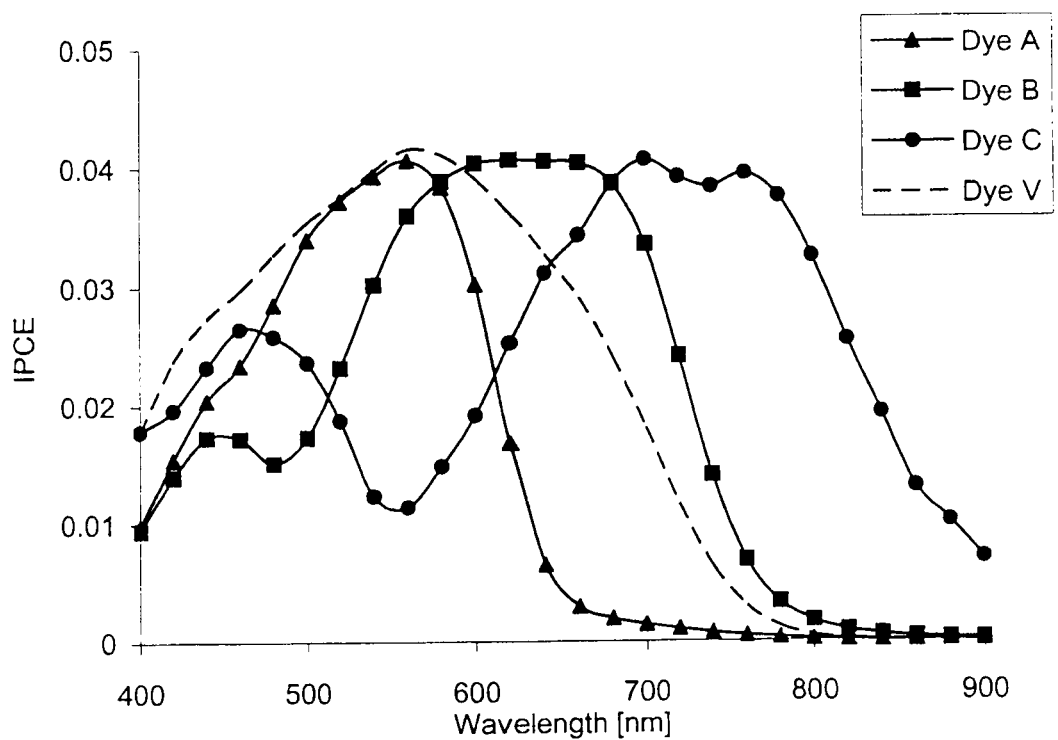
FIG. 3 depicts current/voltage curves for the solar cells of Example 3.

$TiO_2$ layer thickness after sintering: 17 μm 0.5 mM solution of dye V in ethanol (inserted at 80° C.), insertion time 14 h at room temperature Electrolyte: 0.5 M LiI, 0.6 M tetrabutylammonium iodide, 0.05 M $I_2$ and 0.5 M 4-tert-butylpyridine in acetonitrile All solar cells were illuminated under 0.1 sun.
The IPCE curves measured in each case are depicted in FIG. 3. The curve obtained for dye C was fitted to the curves of the other dyes.
The efficiencies ηα determined were 1.6% for dye A, 2.2% for dye B, 0.6% for dye C and 5% for dye V.

Example 4

Dyes D, E, F, G and H were used in $TiO_2$ solar cells.
Description of the Cell and of the Starting Materials:
FTO-coated glass plaques of dimensions 25 mm×15 mm×3 mm $TiO_2$ paste Ti-Nanoxide HT (Solaronix SA) $TiO_2$ layer thickness after sintering (450° C./30 min): 9-10 μm 0.5 mM solution of the dye in dichloromethane (inserted at 80° C.), insertion time 14 h at room temperature Electrolyte: 0.1 M LiI, 0.6 M tetrabutylammonium iodide, 0.05 M $I_2$ and 0.5 M 4-tert-butylpyridine in acetonitrile active area: 0.502 cm$^2$ For comparison, the dye V was used in a $TiO_2$ solar cell. The parameters corresponded, unless stated otherwise, to the abovementioned parameters.

Figure 4:
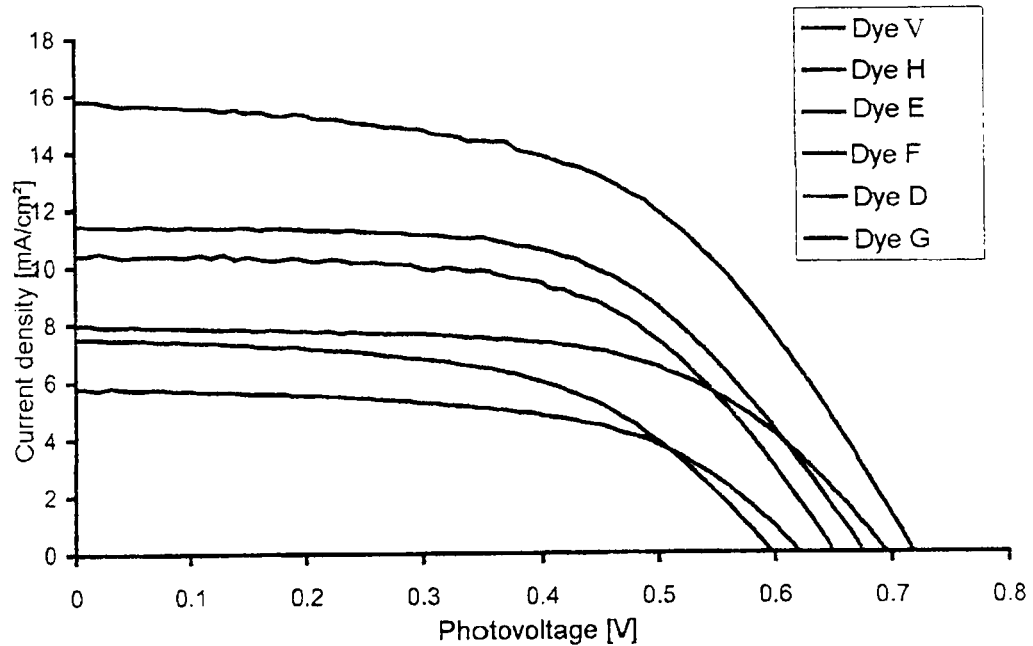
FIG. 4 depicts a current/voltage curve for the solar cell of Example 4.

$TiO_2$ layer thickness after sintering: 9-10 μm 0.5 mM solution of dye V in ethanol (inserted at 80° C.), insertion time 14 h at room temperature Electrolyte: 0.1 M LiI, 0.6 M 2,3-dimethyl-1-propylimidazolium iodide, 0.05 M $I_2$ and 0.5 M 4-tert-butylpyridine in acetonitrile The two solar cells were illuminated under 1.0 sun.
The current/voltage curves measured are depicted in FIG. 4.

The efficiencies η determined were 6.0% for dye V, 4.4% for dye H, 3.9% for dye E, 3.2% for dye F, 2.4% for dye D and 2.0% for dye G.

Example 5

Figure 5:
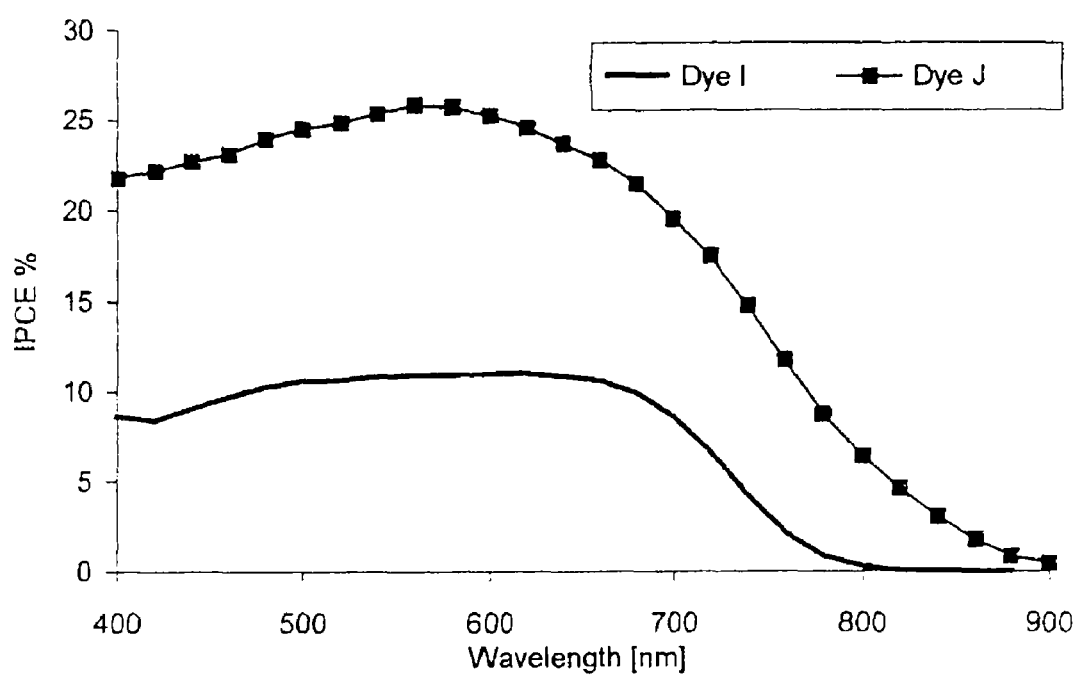
FIG. 5 depicts IPCE curves for the solar cells of Example 5.

Dyes I and J were each used in a $TiO_2$ solar cell.
Description of the Cell and of the Starting Materials:
FTO-coated glass plaques of dimensions 25 mm×15 mm×3 mm $TiO_2$ paste with a $TiO_2$ particle size of 25 nm (ECN) $TiO_2$ layer thickness after sintering (450° C./30 min): 9-10 μm 0.5 mM solution of the particular dye in (dye I) or in dichloromethane (dye J) (inserted at 80° C.), insertion time 14 h at room temperature Electrolyte: 0.5 M LiI, 0.25 M tetrabutylammonium iodide and 0.05 M $I_2$ in 3-methoxypropionitrile active area: 0.502 cm$^2$ The two solar cells were illuminated under 0.1 sun.
The IPCE curves measured in each case are depicted in FIG. 5.
The efficiencies η determined were 1.0% for dye 1 and 0.7% for dye J.

What is claimed is:
1. A solar cell comprising a rylene compound represented by general formula I

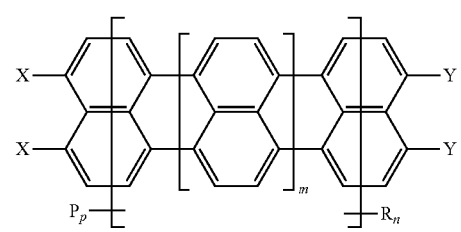

in which the variables are each defined as follows:
X are joined to one another with formation of a six-membered ring to give a radical represented by formula (x1), (x2) or (x3)

or both are a —COOM radical;

Y one of the two radicals is a radical represented by formula (y1)

 (y1)

or a radical represented by formula (y2)

 (y2)

and the other radical in each case is hydrogen;
or both are hydrogen;
each R group is an:
aryloxy, arylthio, hetaryloxy or hetarylthio, to each of which may be fused saturated or unsaturated 5- to 7-membered rings having a carbon skeleton that may be interrupted by one or more of —O—, —S—, —NR$^4$—, —N═CR$^4$—, —CO—, —SO— and —SO$_2$— moieties, where the entire ring system may be mono- or polysubstituted by at least one of the following (i), (ii), (iii), (iv) and (v) radicals:
(i) a C$_1$-C$_{30}$-alkyl having a carbon chain that may be interrupted by one or more —O—, —S—, —NR$^4$—, —N═CR$^4$—, —C≡C—, —CR$^4$═CR$^4$—, —CO—, —SO— and —SO$_2$— moieties and which may be mono- or polysubstituted by at least one of: C$_1$-C$_{12}$-alkoxy, C$_1$-C$_6$-alkylthio, —C≡CR$^4$, —CR$^4$═CR$^4{}_2$, hydroxyl, mercapto, halogen, cyano, nitro, —NR$^9$R$^{10}$, —NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl, and a saturated or unsaturated C$_4$-C$_7$-cycloalkyl having a carbon skeleton that may be interrupted by one or more —O—, —S—, NR4, N═CR$^4$—, —CR$^4$═CR$^4$—, —CO—, —SO— and —SO$_2$— moieties, where the (het)aryl and cycloalkyl radicals may each be mono- or polysubstituted by at least one of a C$_1$-C$_{18}$-alkyl and the above radicals specified as substituents for alkyl;
(ii) a C$_3$-C$_5$-cycloalkyl having a carbon skeleton that may be interrupted by one or more —O—, —S—, —NR$^4$—, —N═CR$^4$—, —CR$^4$═CR$^4$—, —CO—, —SO— and —SO$_2$— moieties and to which may be fused further saturated or unsaturated 5- to 7-membered rings having a carbon skeleton that may be interrupted by one or more —O—, —S—, —NR$^4$—, —N═CR$^4$—, —CR$^4$═CR$^4$—, —CO—, —SO— and —SO$^2$— moieties, where the entire ring system may be mono- or polysubstituted by at least one of: C$_1$-C$_{18}$-alkyl, C$_1$-C$_{12}$-alkoxy, C$_1$-C$_6$-alkylthio, —C≡CR$^4$, —CR$^4$═CR$^4{}_2$, hydroxyl, mercapto, halogen, cyano, nitro, —NR$^9$R$^{10}$NR$^5$COR$^6$, —CONR$^5$R$^6$, —SO$_2$NR$^5$R$^6$, —COOR$^7$, —SO$_3$R$^7$, —PR$^7{}_2$ and —POR$^7$R$^7$ moieties;
(iii) an aryl or hetaryl to which may be fused further with saturated or unsaturated 5- to 7-membered rings having a carbon skeleton that may be interrupted by one or more —O—, —S—, —NR$^4$—, —N═CR$^4$—, —CR$^4$═CR$^4$—, —CO—, —SO— and —SO$_2$— moieties, where the entire ring system may be mono- or polysubstituted by at least one of: C$_1$-C$_{18}$-alkyl, C$_1$-C$_{12}$-alkoxy, C$_1$-C$_6$-alkylthio, —C≡CR$^4$, —CR$^4$═CR$^4{}_2$, hydroxyl, mercapto, halogen, cyano, nitro, —NR$^9$R$^{10}$NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$, (het)aryl, (het)aryloxy and (het)arylthio, where the (het)aryl radicals may each be mono- or polysubstituted by C$_1$-C$_{18}$-alkyl, C$_1$-C$_{12}$-alkoxy, C$_1$-C$_6$-alkylthio, hydroxyl, mercapto, halogen, cyano, nitro, —NR$^9$R$^{10}$NR$^5$COR$^6$, —CONR$^5$R$^6$, —SO$_2$NR$^5$R$^6$, —COOR$^7$, —SO$_3$R$^7$, —PR$^7{}_2$, and —POR$^7$R$^7$;
(iv) a —U-aryl radical which may be mono- or polysubstituted by the above radicals specified as substituents for the aryl radicals (iii), where U is a —O—, —S—, —NR$^4$—, —CO—, —SO— or —SO$_2$— moiety;
(v) a C$_1$-C$_{12}$-alkoxy, C$_1$-C$_6$-alkylthio, —C≡CR$^4$, —CR$^4$═CR$^4{}_2$, hydroxyl, mercapto, halogen, cyano, nitro, —NR$^9$R NR$^5$COR$^6$, —CONR$^5$R$^6$, —SO$_2$NR$^5$R$^6$, —COOR$^7$, —SO$_3$R$^7$, —PR$^7{}_2$, —POR$^7$R$^7$ moiety, or a combination thereof;
P is an amino radical —NR$^1$R$^2$;
B is C$_1$-C$_6$-alkylene, phenylene or a combination of these bridging members, where the phenylene radicals may be mono- or polysubstituted by at least one of a C$_1$-C$_{12}$-alkyl, nitro, cyano and halogen;
A is —COOM, —SO$_3$M or —PO$_3$M$_2$;
D is phenylene, naphthylene or pyridylene, each of which may be mono- or polysubstituted by at least one of C$_1$-C$_{12}$-alkyl, C$_1$-C$_{12}$-alkoxy, hydroxyl, nitro, and halogen;
M is hydrogen, a monovalent or divalent metal cation, an ammonium salt of a cyclic amine, a guanidinium salt or [NR$^5$]$_4{}^+$;
L is a chemical bond or an arylene or hetarylene radical, bonded to the rylene skeleton directly or via ethenylene or ethynylene, of the formulae

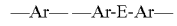

in which the (het)arylene radicals Ar may be the same or different, may comprise heteroatoms as ring atoms, may have fused saturated or unsaturated 5- to 7-membered rings which may likewise comprise heteroatoms or a combination thereof, where the entire ring system may be mono- or polysubstituted by at least one of phenyl, C$_1$-C$_{12}$-alkyl, C$_1$-C$_{12}$-alkoxy, C$_1$-C$_{12}$-alkylthio, and —NR$^5$R$^6$;
E is a chemical bond or an —O—, —S—, —NR$^4$—, —C≡, —CR$^4$═CR$^4$— or C$_1$-C$_6$— alkylene moiety;
R$^1$, R$^2$ are each independently one of the alkyl radicals (i), cycloalkyl radicals (ii) or (het)aryl radicals (iii) specified as substituents for the R radicals;
joined together to form a saturated or unsaturated, 5- to 7-membered ring which comprises the nitrogen atom and whose carbon chain may be interrupted by one or more —O—, —S— and —NR$^4$— moieties, to which may be fused one or two unsaturated or saturated 4- to 8-membered rings whose carbon chain may likewise be interrupted by these moieties or a —N═, where the entire ring system may be mono- or polysubstituted by at least one of: C$_1$-C$_{24}$-alkyl which may be substituted by at least one of C$_1$-C$_{18}$-alkoxy, C$_1$-C$_{18}$-alkylthio and —NR$^5$R$^6$, (het)aryl which may be mono- or polysubstituted by C$_1$-C$_{18}$-alkyl and the aforementioned radicals as substituents for alkyl, C$_1$-C$_{18}$-alkoxy, C$_1$-C$_{18}$-alkylthio, and —NR$^5$R$^6$;
Z is —O— or —S—;
R$^3$ is one of the alkyl radicals (i) or (het)aryl radicals (iii) specified as substituents for the R radicals;
R$^4$ is hydrogen or C$_1$-C$_{18}$-alkyl, where the R$^4$ radicals may be the same or different when they occur more than once;

$R^5$, $R^6$ are each independently:
hydrogen;
a $C_1$-$C_{18}$-alkyl having a carbon chain that may be interrupted by one or more —O—, —S—, —CO—, —SO— and —SO$_2$— moieties and which may be mono- or poly-substituted by at least one of $C_1$-$C_{12}$-alkoxy, $C_1$-$C_6$-alkylthio, hydroxyl, mercapto, halogen, cyano, nitro and —COOR$^S$;
an aryl or hetaryl to each of which may be fused further saturated or unsaturated 5- to 7-membered rings having a carbon skeleton that may be interrupted by one or more —O—, —S—, —CO— and —SO$_2$— moieties, where the entire ring system may be mono- or polysubstituted by at least one of $C_1$-$C_{12}$-alkyl and the above radicals specified as substituents for alkyl, where the $R^5$ radicals may be the same or different when they occur more than once;
$R^7$ is a $C_1$-$C_{18}$-alkyl having a carbon chain that may be interrupted by one or more —O—, —S—, —CO—, —SO— and —SO$_2$— moieties and which may be mono- or polysubstituted by at least one of $C_1$-$C_{12}$-alkoxy, $C_1$-$C_6$-alkylthio, hydroxyl, mercapto, halogen, cyano, nitro and —COOR$^S$ moiety;
an aryl or hetaryl to each of which may be fused further saturated or unsaturated 5- to 7-membered rings whose carbon skeleton may be interrupted by one or more of —O—, —S—, —CO— and —SO$_2$— moieties, where the entire ring system may be mono- or polysubstituted by $C_1$-$C_{12}$-alkyl and/or the above radicals specified as substituents for alkyl, where the $R^7$ radicals may be the same or different when they occur more than once;
$R^8$ is a $C_1$-$C_{18}$-alkyl;
$R^9$, $R^{10}$ are each a $C_1$-$C_{30}$-alkyl having a carbon chain that may be interrupted by one or more —O—, —S—, —NR$^4$—, —N=CR$^4$—, —C≡C—, —CR$^4$=CR$^4$—, —CO—, —SO— and —SO$_2$— moieties and which may be mono- or polysubstituted by at least one of: $C_1$-$C_{12}$-alkoxy, $C_1$-$C_6$-alkylthio, —CR$^4$=CR$^4{}_2$, hydroxyl, —NR$^5$R$^6$, —NR$^5$COR$^6$, (het)aryl and saturated or unsaturated $C_4$-$C_7$-cycloalkyl having a carbon skeleton that may be interrupted by one or more —O—, —S—, —NR$^4$—, —N=CR$^4$— and —CR$^4$=CR$^4$— moieties, where the (het)aryl and cycloalkyl radicals may each be mono- or polysubstituted by at least one of $C_1$-$C_{18}$-alkyl and the above radicals specified as substituents for alkyl;
an aryl or hetaryl to which may be fused further saturated or unsaturated 5- to 7-membered rings having a carbon skeleton that may be interrupted fry one or more —O—, —S—, —NR$^4$—, —N=CR$^4$—, —CR$^4$=CR$^4$—, —CO—, —SO— and —SO$_2$— moieties, where the entire ring system may be mono- or polysubstituted by at least one of: $C_1$-$C_{18}$-alkyl, $C_1$-$C_{12}$-alkoxy, $C_1$-$C_6$-alkylthio, —C≡CR$^4$, —CR$^4$=CR$^4{}_2$, hydroxyl, —NR$^5$R$^6$, —NR$^5$COR$^6$, (het)aryl, (het)aryloxy, and (het)arylthio, where the (het)aryl radicals may in each case be mono- or polysubstituted by at least one of $C_1$-$C_{18}$-alkyl, $C_1$-$C_{12}$-alkoxy, hydroxyl, —NR$^5$R$^6$ and —NR$^5$COR$^6$;
joined to the nitrogen atom to form a saturated or unsaturated, 5- to 7-membered ring having a carbon chain that may be interrupted by one or more —O—, —S— and —NR$^4$-moieties, to which may be fused one or two unsaturated or saturated 4- to 8-membered rings having a carbon chain that may be interrupted by these moieties or —N=, where the entire ring system may be mono- or polysubstituted by at least one of $C_1$-$C_{24}$-alkyl which may be substituted by $C_1$-$C_{18}$-alkoxy, $C_1$-$C_{18}$-alkylthio and —NR$^5$R$^6$, (het)aryl which may be mono- or polysubstituted by at least one of $C_1$-$C_{18}$-alkyl and the above radicals specified as substituents for alkyl, $C_1$-$C_{18}$-alkoxy, $C_1$-$C_{18}$-alkylthio, and —NR$^5$R$^6$;
m is 1 or 2;
n is 0, 2 or 4 when m=1;
is 0, 4 or 6 when m=2;
p is 0, 2 or 4 when m=1, where n+p=0, 2 or 4;
is 0, 4 or 6 when m=2, where n+p=0, 4 or 6.

2. A solar cell according to claim 1, wherein X are joined to one another with formation of a six-membered ring to give a radical represented by formula (x1)

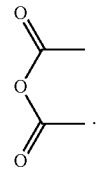

(x1)

3. A solar cell according to claim 1, wherein X are joined to one another with formation of a six-membered ring to give a radical represented by formula (x2)

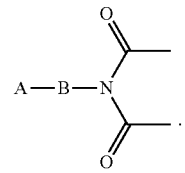

(x2)

4. A solar cell according to claim 1, wherein X are joined to one another with formation of a six-membered ring to give a radical represented by formula (x3)

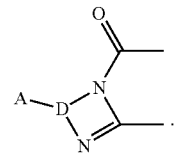

(x3)

5. A solar cell according to claim 1, wherein one Y radical is a radical represented by formula (y1)

-L-NR$^1$R$^2$         (y1)

and one Y radical is a hydrogen radical.

6. A solar cell according to claim 1, wherein one Y radical is a radical represented by formula (y2)

-L-Z—R$^3$         (y2)

and one Y radical is a hydrogen radical.

7. A solar cell according to claim 1, wherein
B is an alkylenephenylene radical, a phenylenealkylene radical, or an alkylenephenylenealkylene radical, optionally substituted at least one of a $C_1$-$C_{12}$-alkyl group, a nitro group, a cyano group, and a halogen group.

8. A solar cell according to claim 1, wherein

B is an unsubstituted alkylenephenylene radical, an unsubstituted phenylenealkylene radical, or an unsubstituted alkylenephenylenealkylene radical.

9. A solar cell according to claim 1, wherein

A is a —COOM group.

10. A solar cell according to claim 1, wherein

A is a —$SO_3M$ group.

11. A solar cell according to claim 1, wherein

A is a —$PO_3M_2$ group.

12. A solar cell according to claim 1, wherein

L is selected from the group consisting of a chemical bond; 1,4-phenylene; 1,3-phenylene; 1,2-phenylene; 1,4-naphthylene; 1,8-naphthylene; 1,4-pyrrylene; 2,3-pyrrylene; 2,5-thienylene; 2,4-thienylene; 2,3-thienylene; 2,5-furanylene; 2,4-furanylene; 2,3-furanylene; 2,3-pyridinylene; 2,4-pyridinylene; 2,5-pyridinylene; 2,6-pyridinylene; 3,4-pyridinylene; 3,5-pyridinylene; 2,3-quinolinylene; 2,5-quinolinylene; 2,6-quinolinylene; 3,7-quinolinylene; 4,8-quinolinylene; 5,8-quinolinylene; 6,7-quinolinylene; 2,7-isoquinolinylene; 3,6-isoquinolinylene; 4,5-isoquinolinylene; 2,6-isoquinolinylene; 3,7-isoquinolinylene; 4,7-isoquinolinylene; 4,8-isoquinolinylene; 4,4'-biphenylene; 3,3'-biphenylene; 2,2'-biphenylene; 3,3'-bithienylene; 2,2'-bithienylene; 1,4-[2,5-di(tert-butyl)]phenylene; 1,4-(2,5-dihexyl)phenylene; 1,4-[2,5-di(tert-octyl)]phenylene; 1,4-(2,5-didodecyl)phenylene; 1,4-[2,5-di(2-dodecyl)]-phenylene; 4,4'-di(2,2',6,6'-tetramethyl)phenylene; 4,4'-di(2,2',6,6'-tetraethyl)phenylene; 4,4'-di(2,2',6,6'-tetraisopropyl)phenylene; 4,4'-di(2,2',6,6'-tetrahexyl)phenylene; 4,4'-di[2,2',6,6'-tetra(2-hexyl)]phenylene; 4,4'-di[2,2',6,6'-tetra(tert-octyl)]phenylene; 4,4'-di(2,2',6,6'-tetradodecyl)phenylene; 4,4'-di[2,2',6,6'-tetra(2-dodecyl)]phenylene; and

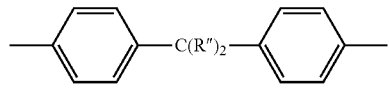

wherein each R″ represents hydrogen, a methyl group, an ethyl group, or a phenyl group.

13. A solar cell according to claim 1, wherein

L is selected from the group consisting of a chemical bond; 1,4-phenylene; 2,3-thienylene; and 4,4'-di(2,2',6,6'-tetramethyl)phenylene.

14. A solar cell according to claim 1, wherein the Y radical represented by formula (y1) is a radical represented by one of the following formulae:

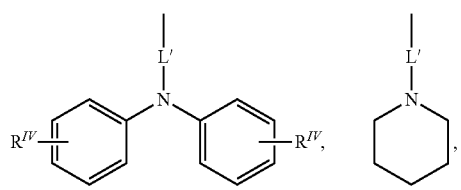

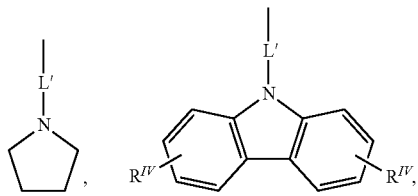

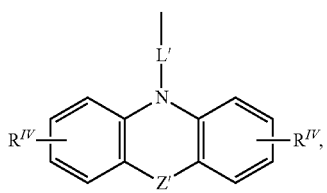

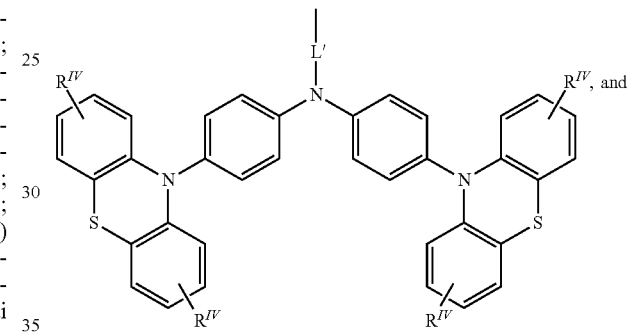

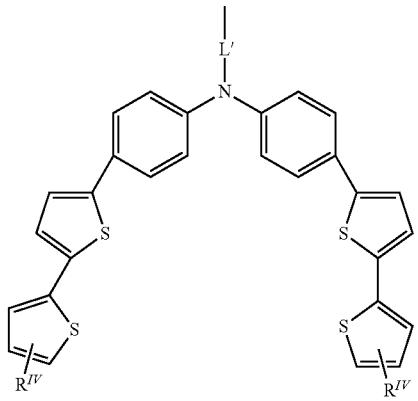

wherein

L' is a chemical bond or 1,4-phenylene;

Z' is —O—, —S—, —$NR^{8'}$— or —$CH_2$—, where $R^{8'}$ is $C_1$-$C_{18}$-alkyl;

$R^{IV}$ is $C_4$-$C_{18}$-alkyl, $C_1$-$C_{18}$-alkoxy, (hetero)aryl or —$NR^5R^6$ and one Y radical is a hydrogen radical.

15. A solar cell according to claim 1, wherein the Y radical represented by formula (y2) is at least one of a phenoxy radical, a phenylthio radical, a naphthyloxy radical, and a naphthylthio radical, each of is optionally substituted with at least one of a $C_4$-$C_{18}$-alkyl group, a $C_1$-$C_{18}$-alkoxy group, and a —$NR^5R^6$.

16. A solar cell according to claim 1, wherein the rylene compound is
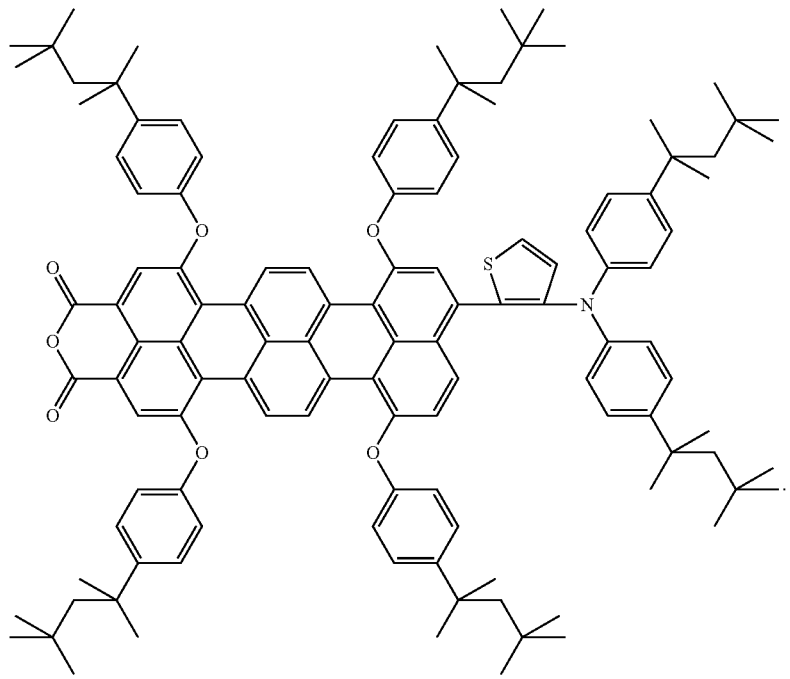 [SMILES: CC(C)(C)CC(C)(C)c1ccc(Oc2ccc3c(-c4sccc4N(c4ccc(C(C)(C)CC(C)(C)C)cc4)c4ccc(C(C)(C)CC(C)(C)C)cc4)cc(Oc4ccc(C(C)(C)CC(C)(C)C)cc4)c4c5ccc6c7c(Oc8ccc(C(C)(C)CC(C)(C)C)cc8)cc8c9c(cc(Oc%10ccc(C(C)(C)CC(C)(C)C)cc%10)c(c%10ccc(c2c34)c5c%106)c97)C(=O)OC8=O)cc1]
17. A solar cell according to claim 1, wherein the rylene compound is
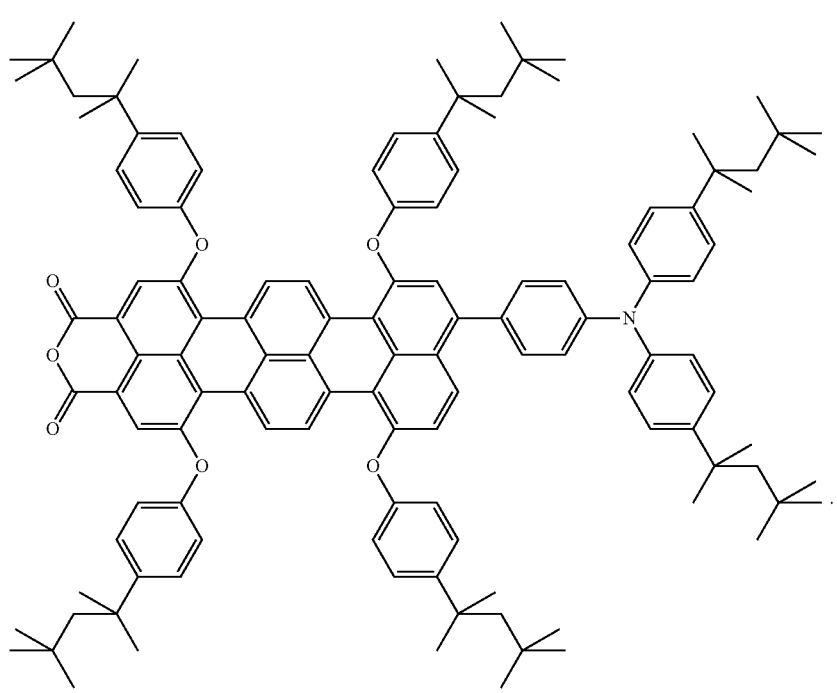 [SMILES: CC(C)(C)CC(C)(C)c1ccc(Oc2ccc3c(-c4ccc(N(c5ccc(C(C)(C)CC(C)(C)C)cc5)c5ccc(C(C)(C)CC(C)(C)C)cc5)cc4)cc(Oc4ccc(C(C)(C)CC(C)(C)C)cc4)c4c5ccc6c7c(Oc8ccc(C(C)(C)CC(C)(C)C)cc8)cc8c9c(cc(Oc%10ccc(C(C)(C)CC(C)(C)C)cc%10)c(c%10ccc(c2c34)c5c%106)c97)C(=O)OC8=O)cc1]

18. A solar cell according to claim 1, wherein the rylene compound is
20. A solar cell according to claim 1, wherein the rylene compound is
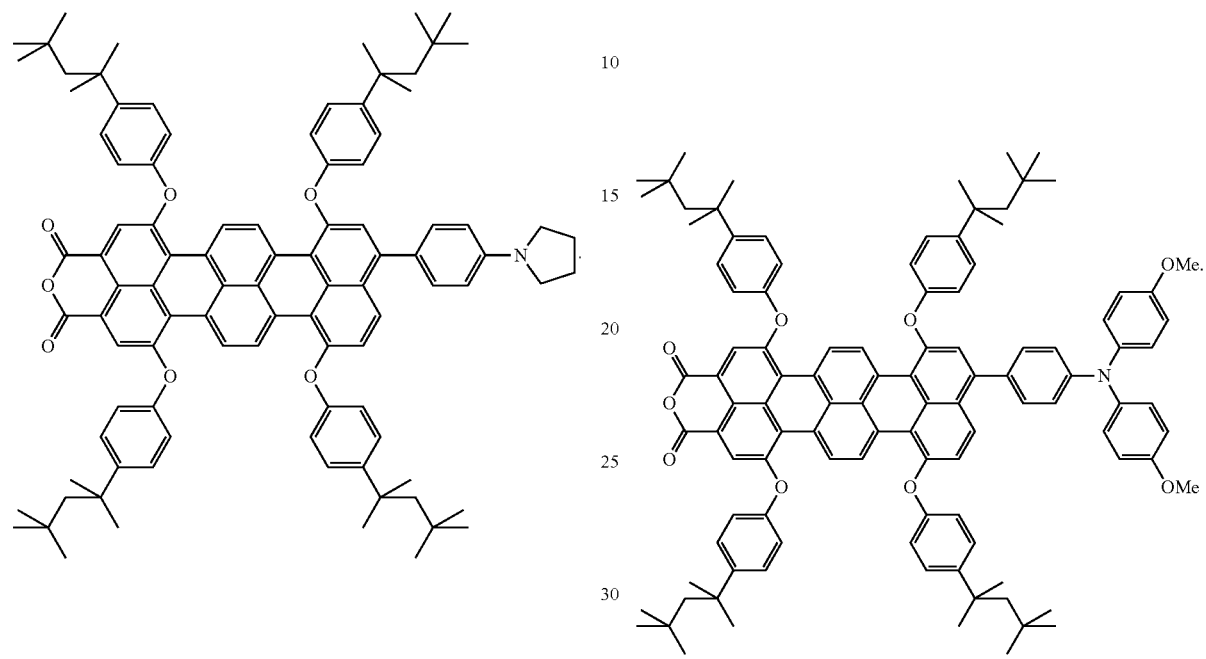
19. A solar cell according to claim 1, wherein the rylene compound is
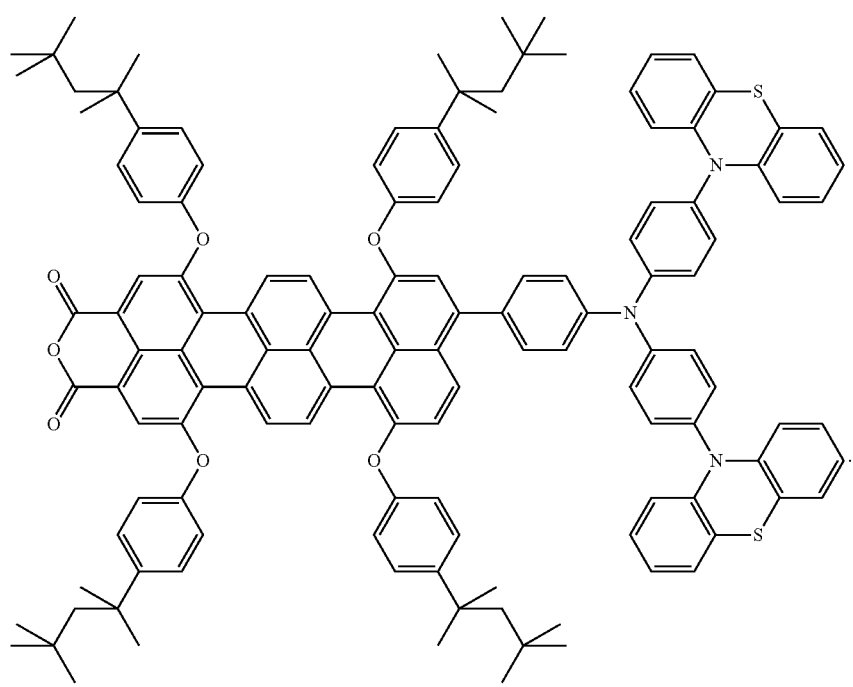 [SMILES: CC(C)(C)CC(C)(C)c1ccc(Oc2ccc3c(-c4ccc(N(c5ccc(N6c7ccccc7Sc7ccccc76)cc5)c5ccc(N6c7ccccc7Sc7ccccc76)cc5)cc4)cc(Oc4ccc(C(C)(C)CC(C)(C)C)cc4)c4c5ccc6c7c(Oc8ccc(C(C)(C)CC(C)(C)C)cc8)cc8c9c(cc(Oc%10ccc(C(C)(C)CC(C)(C)C)cc%10)c(c%10ccc(c2c34)c5c%106)c97)C(=O)OC8=O)cc1]

21. A solar cell according to claim 1, wherein the rylene compound is
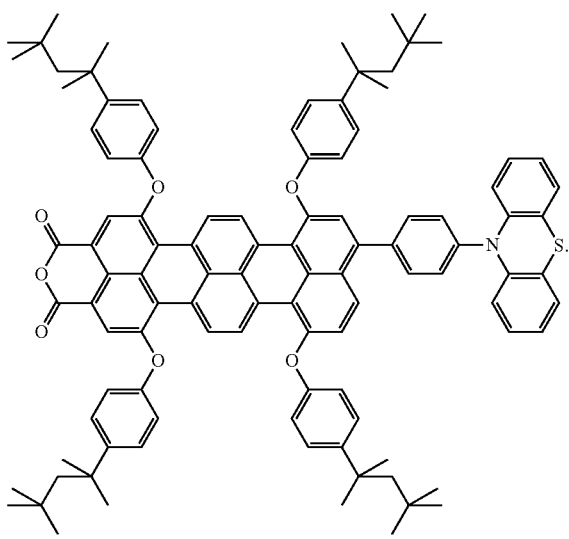 [SMILES: CC(C)(C)CC(C)(C)c1ccc(Oc2ccc3c(-c4ccc(N5c6ccccc6Sc6ccccc65)cc4)cc(Oc4ccc(C(C)(C)CC(C)(C)C)cc4)c4c5ccc6c7c(Oc8ccc(C(C)(C)CC(C)(C)C)cc8)cc8c9c(cc(Oc%10ccc(C(C)(C)CC(C)(C)C)cc%10)c(c%10ccc(c2c34)c5c%106)c97)C(=O)OC8=O)cc1]
22. A solar cell according to claim 1, wherein the rylene compound is
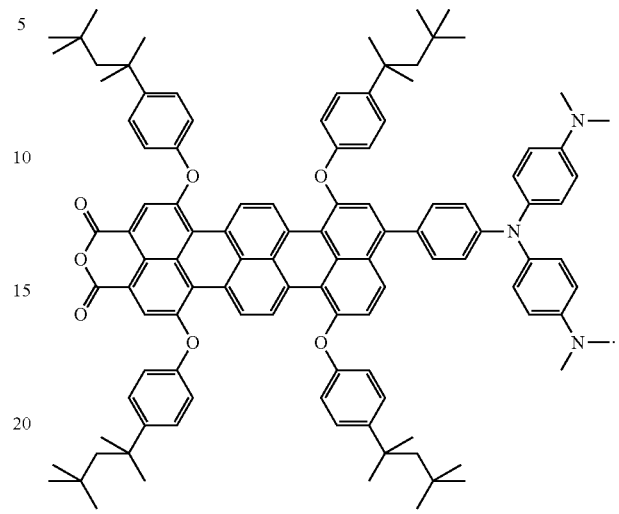
* * * * *